United States Patent
Terefe et al.

(10) Patent No.: US 11,925,385 B2
(45) Date of Patent: Mar. 12, 2024

(54) TROCAR WITH OBLIQUE NEEDLE INSERTION PORT AND PERPENDICULAR SEAL LATCH

(71) Applicant: Cilag GmbH International, Zug (CH)

(72) Inventors: Muluken B. Terefe, Houston, TX (US); Shailendra K. Parihar, Mason, OH (US); Jason L Harris, Lebanon, OH (US); Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 97 days.

(21) Appl. No.: 17/163,817

(22) Filed: Feb. 1, 2021

(65) Prior Publication Data

US 2021/0204974 A1   Jul. 8, 2021

Related U.S. Application Data

(63) Continuation of application No. 15/827,174, filed on Nov. 30, 2017, now Pat. No. 10,939,937, which is a
(Continued)

(51) Int. Cl.
*A61B 17/34* (2006.01)
*A61B 17/00* (2006.01)
(Continued)

(52) U.S. Cl.
CPC ...... *A61B 17/3421* (2013.01); *A61B 17/0057* (2013.01); *A61B 17/3417* (2013.01);
(Continued)

(58) Field of Classification Search
CPC ............ A61B 17/3421; A61B 17/0057; A61B 17/3417; A61B 17/3423; A61B 17/3474;
(Continued)

(56) References Cited

U.S. PATENT DOCUMENTS 3,877,434 A   4/1975   Ferguson et al.
3,995,619 A   12/1976   Glatzer
(Continued)

FOREIGN PATENT DOCUMENTS

CN   101711693 A   5/2010
CN   103370013 A   10/2013
(Continued)

OTHER PUBLICATIONS

Partial European Search Report and Provisional Written Opinion dated Oct. 5, 2018, for Application No. 18180458.4, 16 pages.
(Continued)

*Primary Examiner* — Theodore J Stigell
(74) *Attorney, Agent, or Firm* — Frost Brown Todd LLP

(57) ABSTRACT

A surgical access device includes a cannula and a housing coupled to the cannula. A cannula lumen and a housing interior communicate to define a working channel that extends along a central axis of the device between proximal and distal device ends. A needle entrance port is arranged on a side portion of the housing and opens to the working channel. A needle exit port is arranged distally of the needle entrance port on a side portion of the cannula, and communicates with the needle entrance port to define a suture path extending through the surgical access device at an oblique angle relative to the central axis. The needle ports are configured to guide a suture passer device distally through the surgical access device and first and second tissues of different thicknesses, while maintaining the same tissue bite distance in each of the first and second tissues.

18 Claims, 30 Drawing Sheets

Related U.S. Application Data continuation-in-part of application No. 15/637,683, filed on Jun. 29, 2017, now Pat. No. 10,639,068.

(51) Int. Cl.
*A61B 17/04* (2006.01)
*A61B 17/06* (2006.01)

(52) U.S. Cl.
CPC ...... *A61B 17/3423* (2013.01); *A61B 17/3474* (2013.01); *A61B 17/3496* (2013.01); *A61B 2017/00637* (2013.01); *A61B 2017/00663* (2013.01); *A61B 17/0469* (2013.01); *A61B 17/0482* (2013.01); *A61B 2017/06042* (2013.01); *A61B 2017/3419* (2013.01); *A61B 17/3462* (2013.01); *A61B 2017/3484* (2013.01)

(58) Field of Classification Search
CPC ............ A61B 17/3496; A61B 17/0469; A61B 17/0482; A61B 17/3462; A61B 2017/00637; A61B 2017/00663; A61B 2017/06042; A61B 2017/3419; A61B 2017/3484

See application file for complete search history.

(56) References Cited

U.S. PATENT DOCUMENTS

| | | |
|---|---|---|
| 5,507,758 A | 4/1996 | Thomason et al. |
| 5,792,135 A | 8/1998 | Madhani et al. |
| 5,817,084 A | 10/1998 | Jensen |
| 5,878,193 A | 3/1999 | Wang et al. |
| 6,042,583 A | 3/2000 | Thompson et al. |
| 6,231,565 B1 | 5/2001 | Tovey et al. |
| 6,364,888 B1 | 4/2002 | Niemeyer et al. |
| 6,569,119 B1 * | 5/2003 | Haberland ......... A61B 17/3462 604/167.03 |
| 6,783,524 B2 | 8/2004 | Anderson et al. |
| 7,524,320 B2 | 4/2009 | Tierney |
| 7,585,288 B2 | 9/2009 | Haberland et al. |
| 7,691,098 B2 | 4/2010 | Wallace et al. |
| 7,803,135 B2 | 9/2010 | Franer |
| 7,806,891 B2 | 10/2010 | Nowlin et al. |
| 7,981,092 B2 | 7/2011 | Duke |
| 8,226,553 B2 | 7/2012 | Shelton, IV et al. |
| 8,251,900 B2 | 8/2012 | Ortiz et al. |
| 8,449,460 B2 | 5/2013 | Duke et al. |
| 8,479,969 B2 | 7/2013 | Shelton, IV |
| 8,568,362 B2 | 10/2013 | Moreno et al. |
| 8,573,461 B2 | 11/2013 | Shelton, IV et al. |
| 8,573,465 B2 | 11/2013 | Shelton, IV |
| 8,579,807 B2 | 11/2013 | Moreno et al. |
| 8,602,288 B2 | 12/2013 | Shelton, IV et al. |
| 8,616,431 B2 | 12/2013 | Timm et al. |
| 8,636,686 B2 | 1/2014 | Minnelli et al. |
| 8,668,711 B2 | 3/2014 | Teichtmann et al. |
| 8,690,831 B2 | 4/2014 | Duke |
| 8,783,541 B2 | 7/2014 | Shelton, IV et al. |
| 8,800,838 B2 | 8/2014 | Shelton, IV |
| 8,820,605 B2 | 9/2014 | Shelton, IV |
| 8,844,789 B2 | 9/2014 | Shelton, IV et al. |
| 9,301,759 B2 | 4/2016 | Spivey et al. |
| 9,687,226 B2 | 6/2017 | Hodgkinson et al. |
| 9,700,303 B2 | 7/2017 | Prior et al. |
| 10,485,580 B2 | 11/2019 | Parihar et al. |
| 10,568,619 B2 | 2/2020 | Shelton, IV et al. |
| 10,639,029 B2 | 5/2020 | Parihar et al. |
| 10,639,068 B2 | 5/2020 | Parihar et al. |
| 10,675,018 B2 | 6/2020 | Jast et al. |
| 10,709,440 B2 | 7/2020 | Shelton, IV et al. |
| 10,709,473 B2 | 7/2020 | Shelton, IV et al. |
| 10,869,690 B2 | 12/2020 | Parihar et al. |
| 10,939,937 B2 | 3/2021 | Terefe et al. |
| 11,389,192 B2 | 7/2022 | Shelton, IV et al. |
| 2005/0021055 A1 | 1/2005 | Toubia et al. |
| 2007/0004968 A1 | 1/2007 | Bonadio et al. |
| 2008/0200950 A1 | 8/2008 | Wohlert |
| 2009/0005738 A1 | 1/2009 | Franer |
| 2011/0082475 A1 * | 4/2011 | Smith ................ A61B 17/0482 606/144 |
| 2011/0112557 A1 | 5/2011 | Beeley |
| 2014/0163323 A1 * | 6/2014 | Mohajer-Shojaee ........................ A61B 17/3421 600/204 |
| 2015/0038793 A1 * | 2/2015 | Prior ..................... A61M 5/329 600/204 |
| 2016/0228107 A1 | 8/2016 | Madsen et al. |
| 2017/0079639 A1 | 3/2017 | Reza |
| 2017/0281154 A1 | 10/2017 | Hess et al. |

FOREIGN PATENT DOCUMENTS

| | | |
|---|---|---|
| CN | 204351880 U | 5/2015 |
| CN | 105377151 A | 3/2016 |
| CN | 105636526 A | 6/2016 |
| EP | 2168511 A2 | 3/2010 |
| EP | 3225202 A1 | 10/2017 |
| JP | 2010-158518 A | 7/2010 |
| WO | WO 00/28903 A1 | 5/2000 |
| WO | WO 2010/000033 A1 | 1/2010 |
| WO | WO 2012/034131 A2 | 3/2012 |
| WO | WO 2013/105993 A2 | 7/2013 |
| WO | WO 2014/169215 A2 | 10/2014 |
| WO | WO 2015/114560 A1 | 8/2015 |

OTHER PUBLICATIONS

European Search Report, Extended, and Written Opinion dated Jan. 29, 2019, for Application No. 18180458.4, 14 pages.
European Search Report dated Nov. 29, 2021, for Application No. 21175690.3, 9 pages.
International Search Report and Written Opinion dated Feb. 14, 2019, for Application No. PCT/IB2018/054522, 24 pages.
Chinese Office Action, The First Office Action, and First Search, dated Sep. 5, 2022 for Application No. CN 201880043848.9, 12 pgs.
Japanese Office Action, Notice of Reasons for Refusal, and Search Report by Registered Search Organization, dated May 31, 2022 for Application No. JP 2019-571714, 24 pgs.
Japanese Office Action, Decision to Grant a Patent, dated Dec. 13, 2022 for Application No. JP 2019-571714, 2 pgs.

* cited by examiner

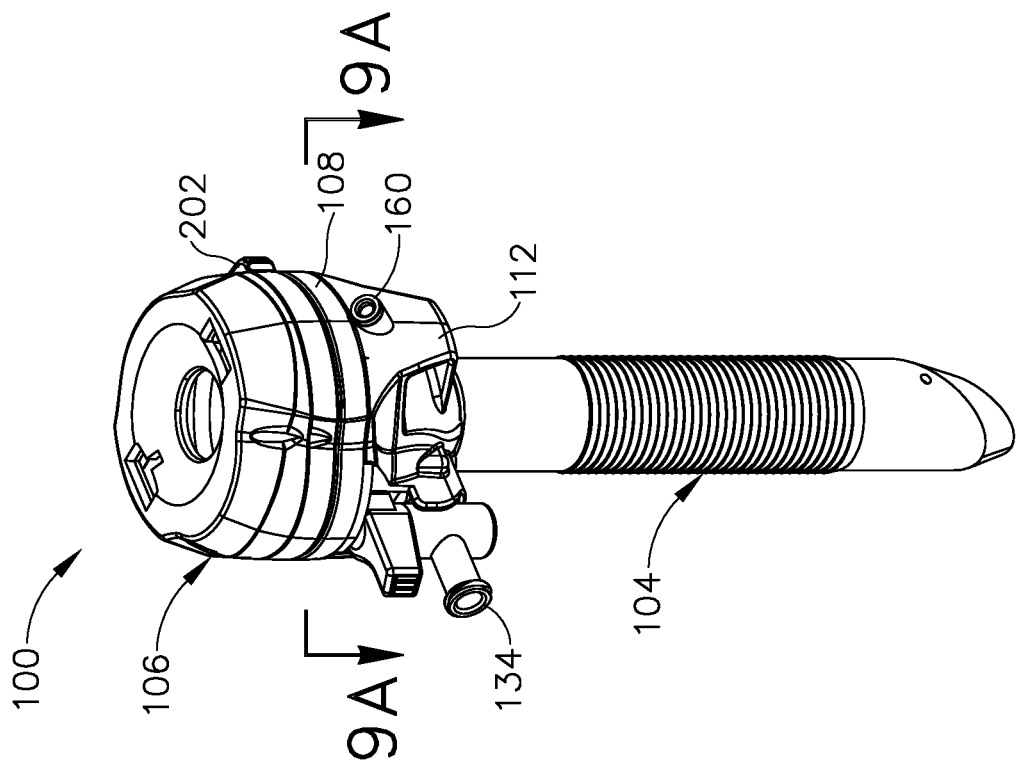
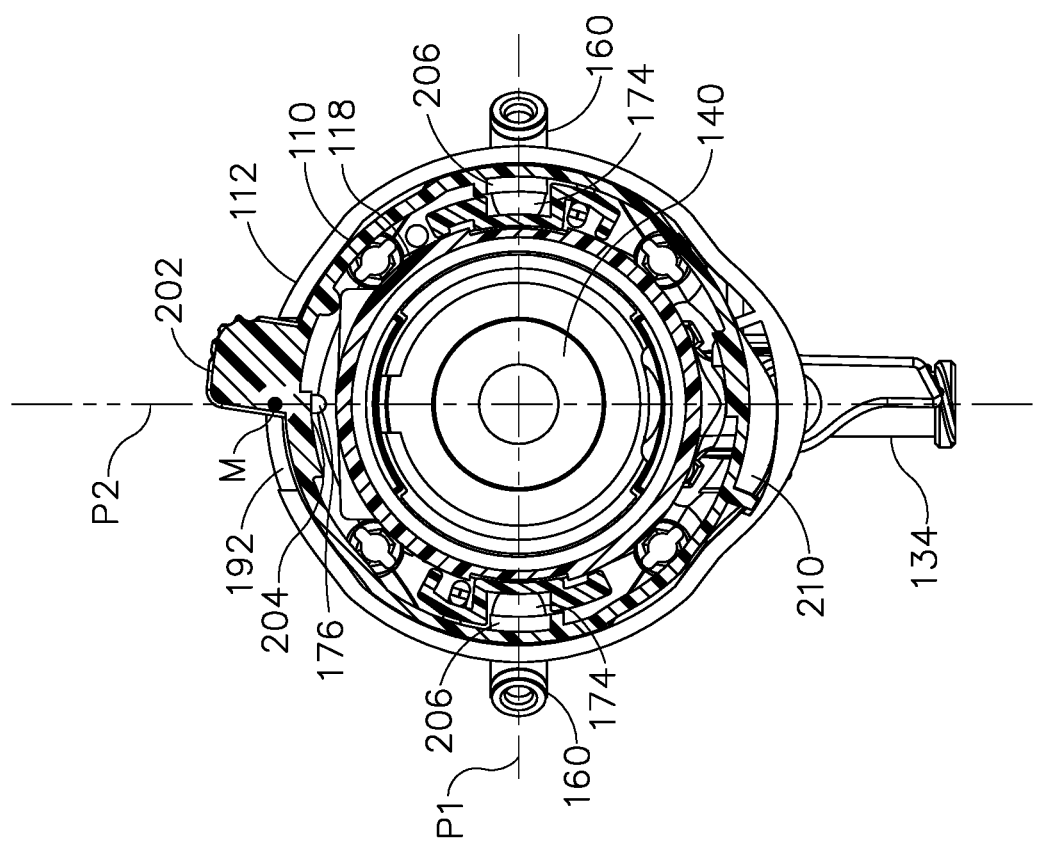

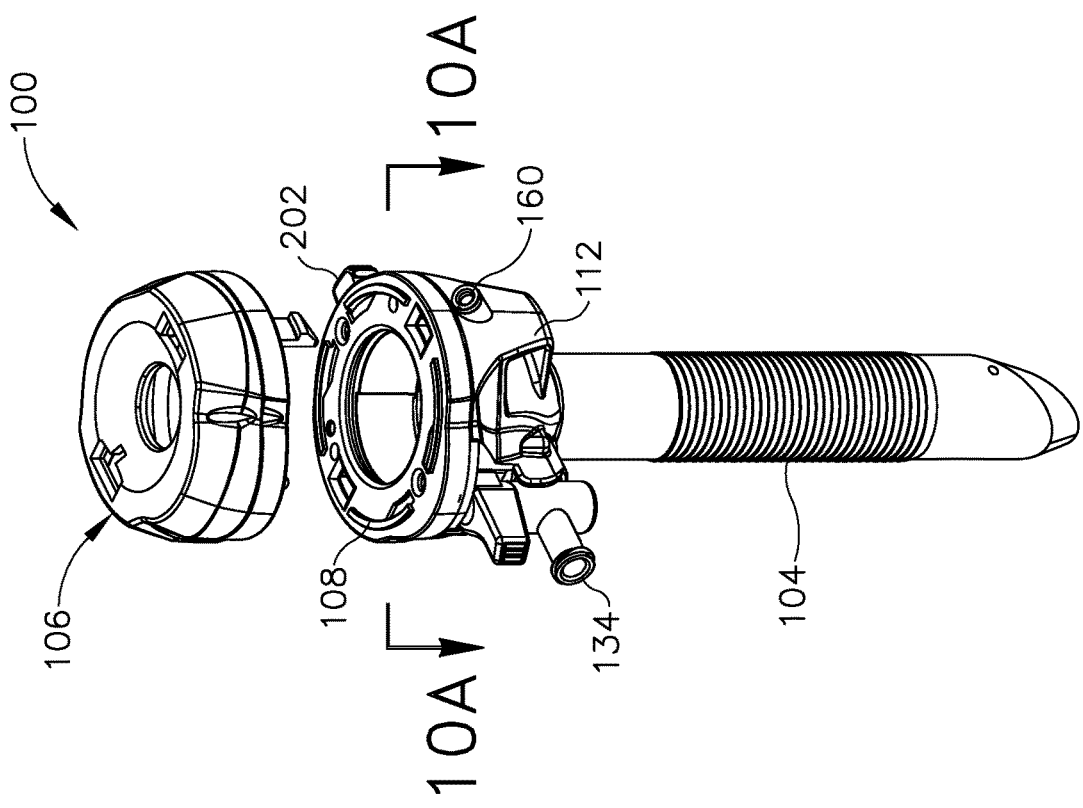
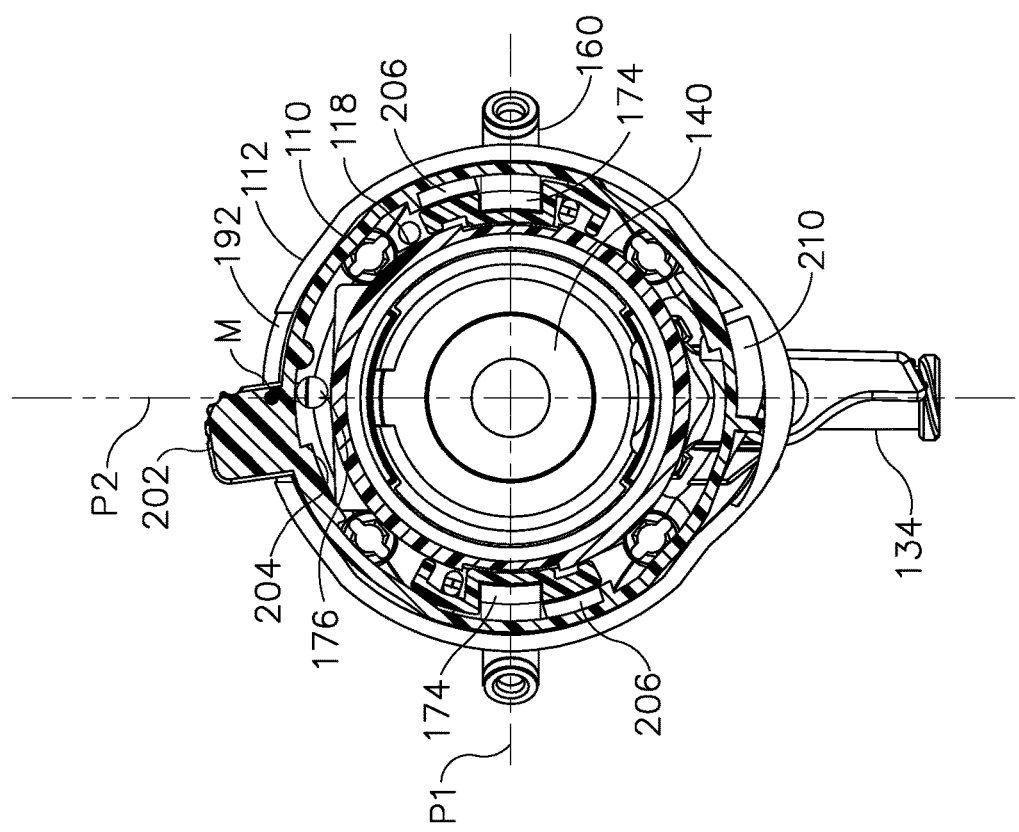
Fig.10B
Fig.10A

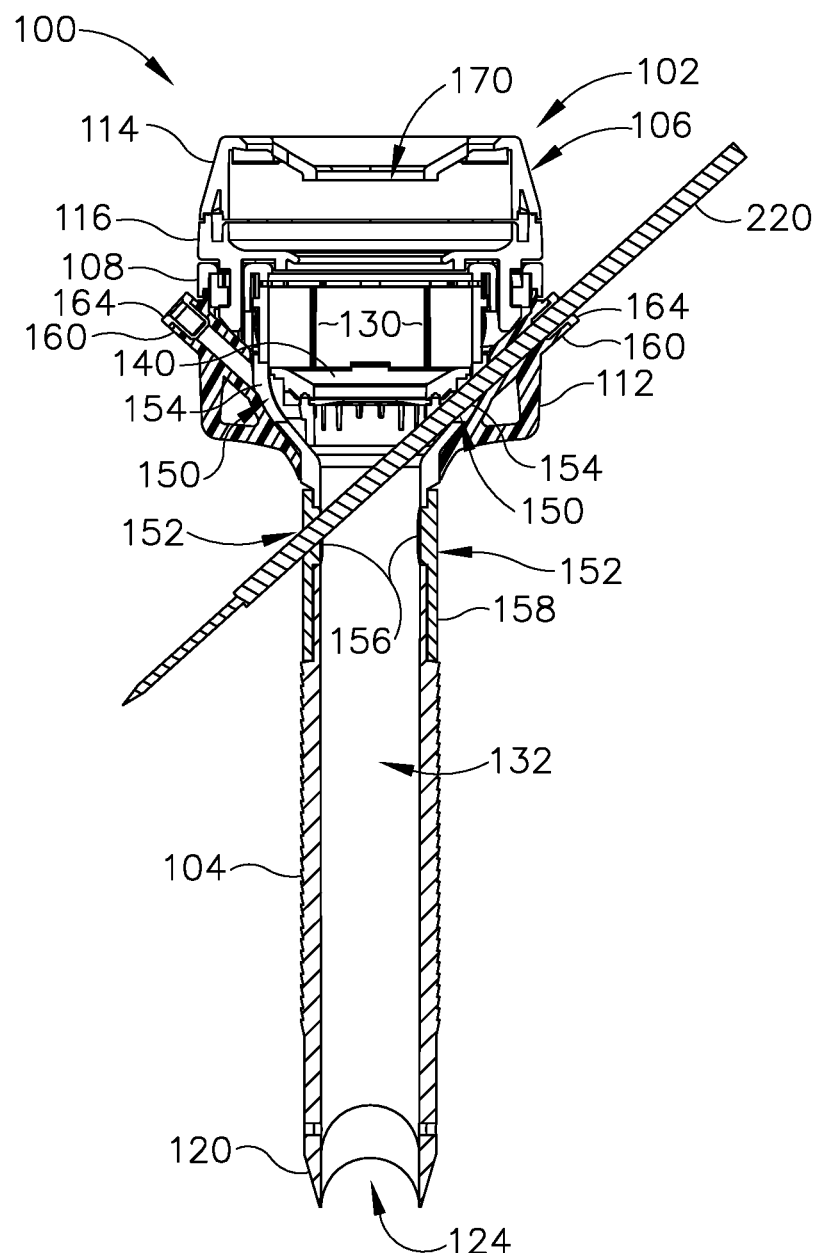
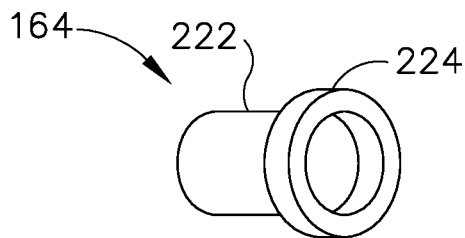
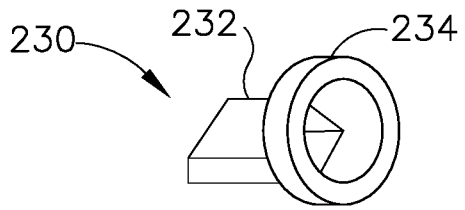

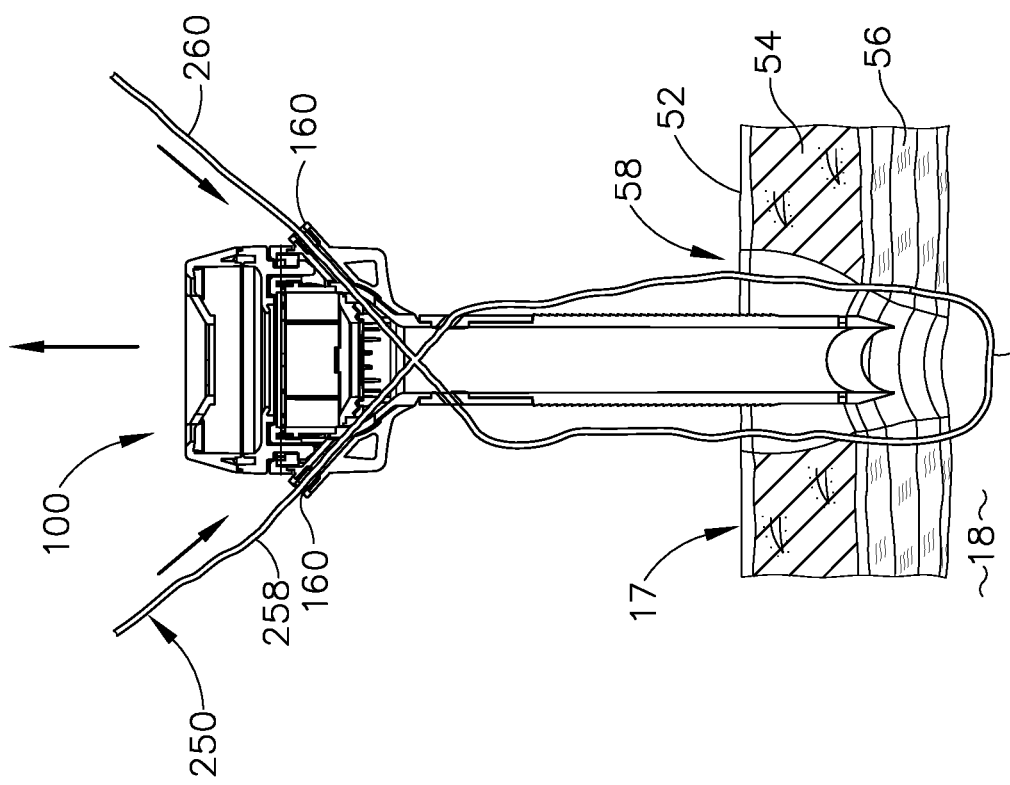
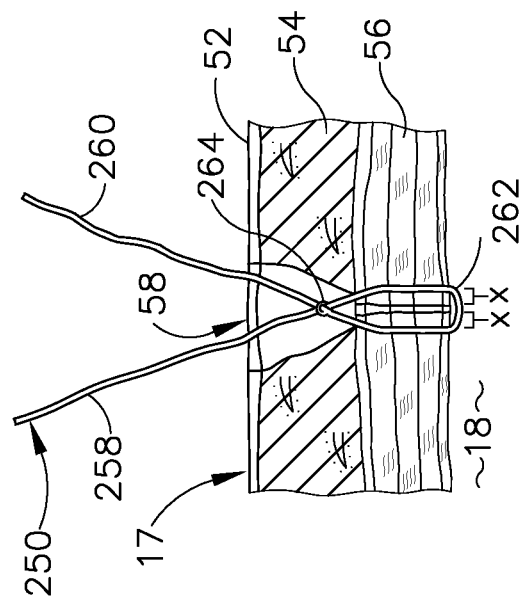
Fig.15D
Fig.15E

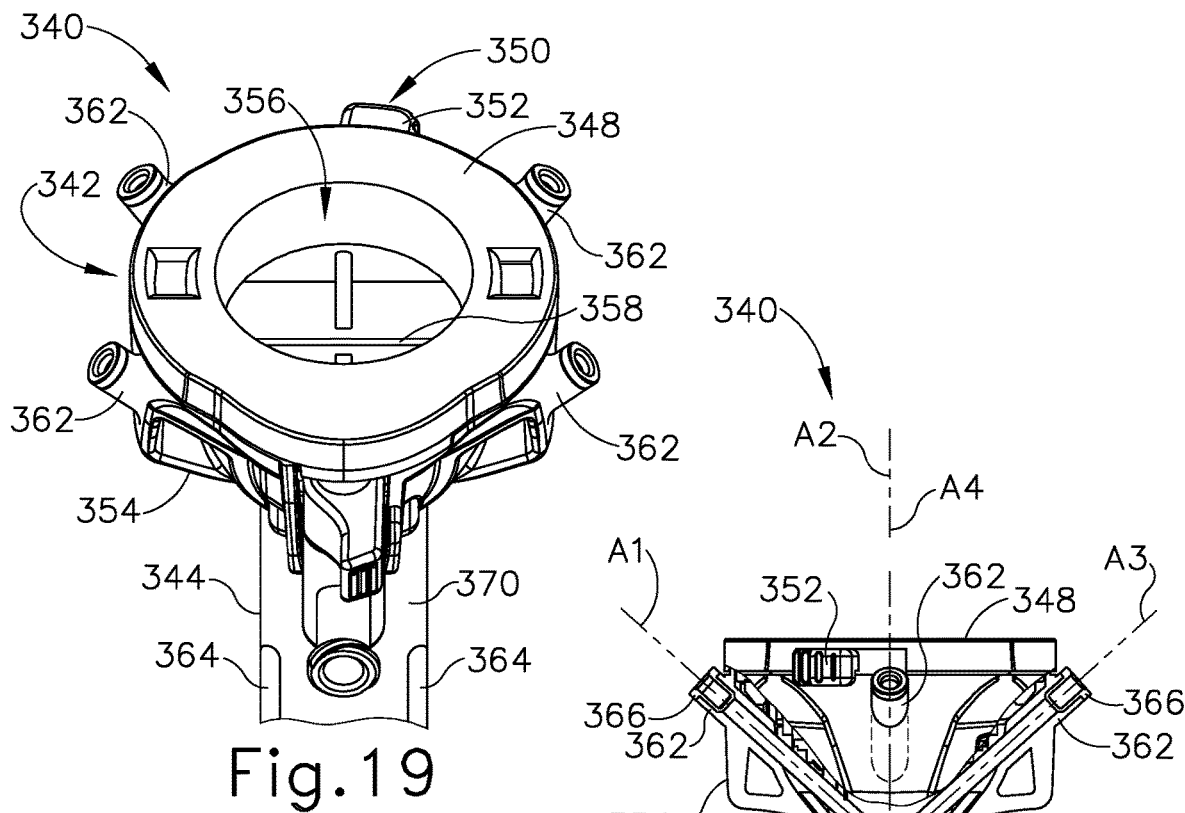
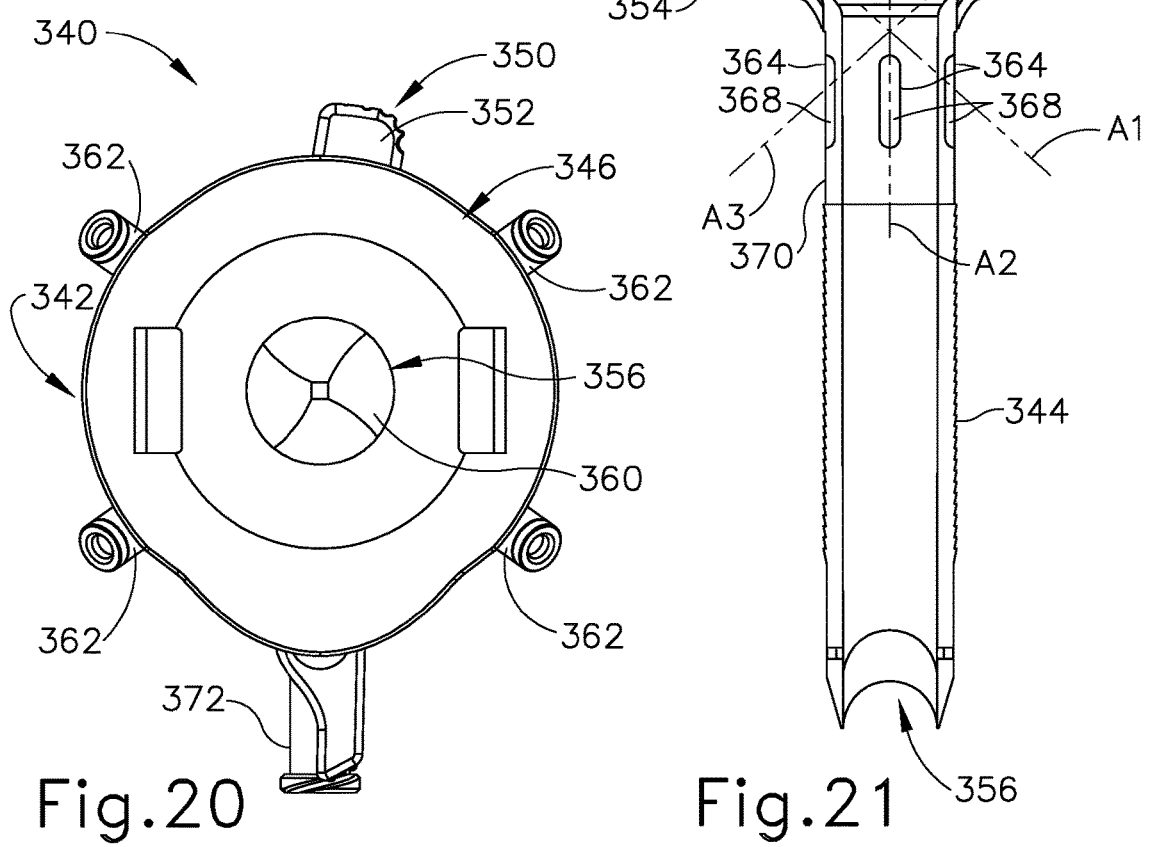

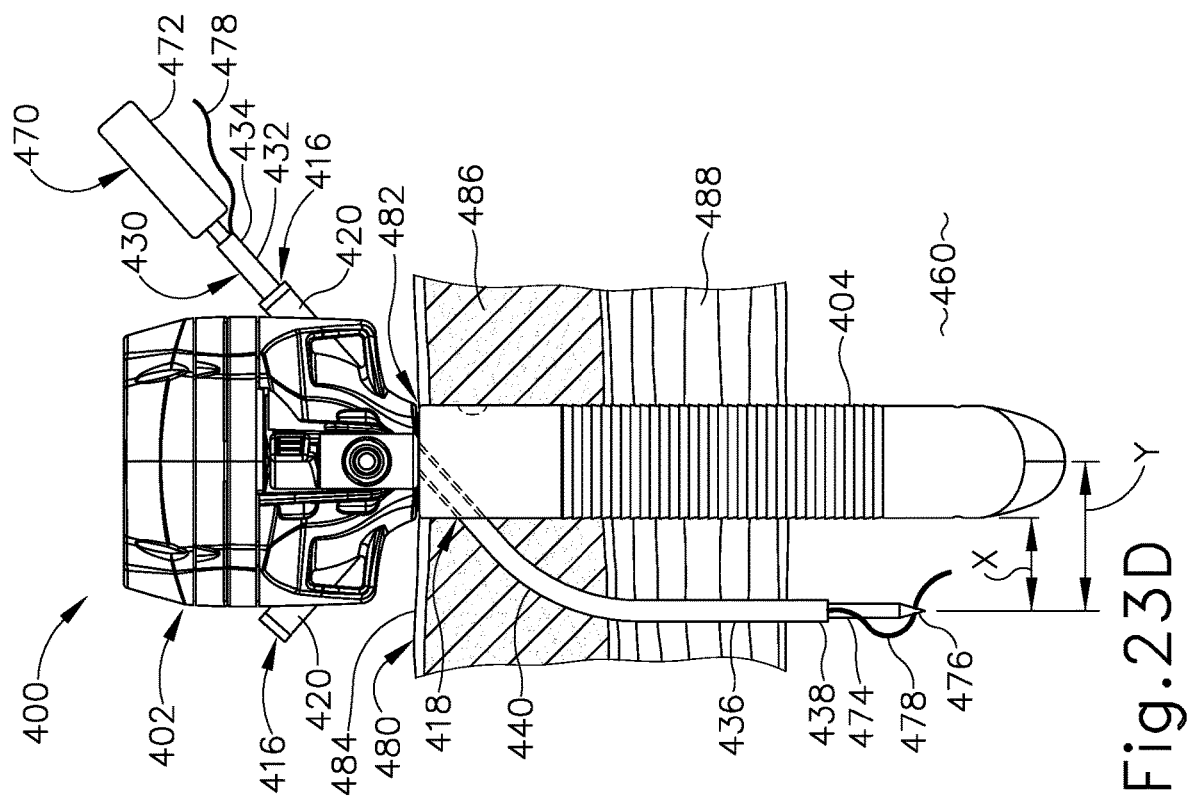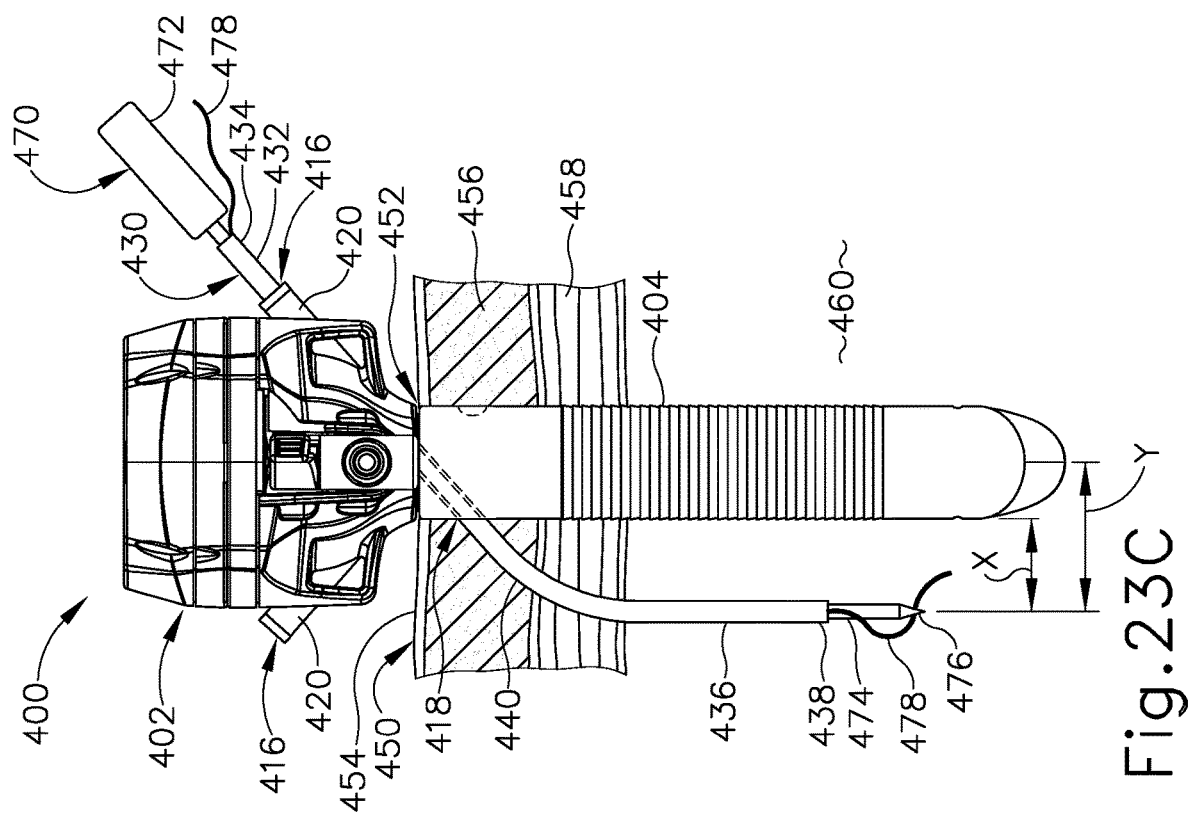

TROCAR WITH OBLIQUE NEEDLE INSERTION PORT AND PERPENDICULAR SEAL LATCH

This application is a continuation of U.S. application Ser. No. 15/827,174, entitled "Trocar with Oblique Needle Insertion Port and Perpendicular Seal Latch," filed Nov. 30, 2017, issued as U.S. Pat. No. 10,939,937; which is a continuation in part of U.S. patent application Ser. No. 15/637,683, entitled "Trocar with Oblique Needle Insertion Port and Perpendicular Seal Latch," filed on Jun. 29, 2017, issued as U.S. Pat. No. 10,639,068 on May 5, 2020, the disclosure of which is incorporated by reference herein.

BACKGROUND

Surgical procedures may require a clinician to gain access to a cavity or other desirable surgical site within a body of a patient. To perform such a surgical procedure, an incision may be made through a tissue of the patient into the cavity. Some conventional surgical procedures may apply a knife, such as a scalpel, to the tissue for the incision, while some less invasive surgical procedures, such as laparoscopic and endoscopic surgical procedures, may access the cavity through a trocar assembly. Traditional trocar assemblies generally include a trocar obturator received within a trocar cannula. In use, the clinician directs the trocar obturator and the cannula through the tissue in order to access the cavity of the desirable surgical site. Once accessed, the clinician withdraws the trocar obturator from the trocar cannula so that the trocar cannula may be used to introduce surgical instruments into the cavity for treatment.

Examples of trocar assemblies, components thereof, and other varieties of surgical access devices and wound closure devices are provided for in U.S. Pat. No. 7,981,092, entitled "Vibratory Trocar," issued Jul. 19, 2011; U.S. Pat. No. 8,226,553, entitled "Access Device with Insert," issued on Jul. 24, 2012; U.S. Pat. No. 8,251,900, entitled "Surgical Access Devices and Methods Providing Seal Movement in Predefined Paths," issued on Aug. 28, 2012; U.S. Pat. No. 8,579,807, entitled "Absorbing Fluids in a Surgical Access Device," issued on Nov. 12, 2013; U.S. Pat. No. 8,568,362, entitled "Surgical Access Device with Sorbents," issued on Oct. 29, 2013; U.S. Pat. No. 8,636,686, entitled "Surgical Access Device," issued on Jan. 28, 2014; U.S. Pat. No. 8,690,831, entitled "Gas Jet Fluid Removal in a Trocar," issued on Apr. 8, 2014; U.S. Pat. Pub. No. 2008/0200950, entitled "Surgical Hook," published on Aug. 21, 2008, now abandoned; U.S. Pat. Pub. No. 2015/0038793, entitled "Devices, Systems, and Methods for Providing Surgical Access and Facilitating Closure of Surgical Access Openings," published on Feb. 5, 2015, issued as U.S. Pat. No. 10,258,324 on Apr. 16, 2019; U.S. Pat. No. 9,700,303, entitled "Devices, Systems, and Methods for Providing Surgical Access and Facilitating Closure of Surgical Access Openings,", issued on Jul. 11, 2017; and U.S. Pat. No. 9,687,226, entitled "Wound Closure Device including Mesh Barrier," issued on Jun. 27, 2017. The disclosure of each of the above-cited U.S. Patents and Publications is incorporated by reference herein.

Surgical instruments for use with such surgical access devices may have a distal end effector for engaging tissue through the access device in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Laparoscopic and endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the cavity of the patient. Positioning of an end effector may be further facilitated through inclusion of one or more articulation joints or features, enabling the end effector to be selectively articulated or otherwise deflected relative to the longitudinal axis of the shaft.

While various kinds of surgical instruments, including surgical access devices and end effectors, and other associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 9A depicts a top sectional view of the trocar of FIG. 5A, taken along section line 9A-9A shown in FIG. 9B, showing a latch ring of the trocar housing in a first exemplary rotational position;

FIG. 9B depicts a front perspective view of the trocar of FIG. 5A, showing a proximal housing of the trocar housing in a coupled state corresponding to the latch ring rotational position of FIG. 9A;

FIG. 10A depicts a top sectional view of the trocar of FIG. 5A, taken along section line 10A-10A shown in FIG. 10B, showing the latch ring in a second exemplary rotational position;

FIG. 10B depicts a front perspective view of the trocar of FIG. 5A, showing the proximal housing in a decoupled state corresponding to the latch ring rotational position of FIG. 9A;

FIG. 11 depicts a side sectional view of the trocar of FIG. 5A, showing an exemplary suture needle passer extending through the trocar along a first suture path oriented obliquely relative to a central axis of the trocar;

FIG. 12A depicts a perspective view of an exemplary pierceable seal provided at the entrance ends of first and second needle guide tubes of the trocar of FIG. 5A;

FIG. 12B depicts a perspective view of another exemplary pierceable seal provided at the entrance ends of first and second needle guide tubes of the trocar of FIG. 5A;

FIG. 15D depicts a schematic side sectional view of the tissue and trocar of FIG. 15A, showing completion of an exemplary fourth step of the suturing procedure in which the suture passer device and suture thread end are removed proximally such that the suture thread passes through two portions of the tissue fascia layers and proximally through the trocar, and the trocar is removed proximally from the tissue opening;

FIG. 15E depicts a schematic side sectional view of the tissue and trocar of FIG. 15A, showing completion of an exemplary fifth step of the suturing procedure in which the suture thread is pulled and knotted to draw together the tissue fascia layers;

FIG. 19 depicts a top perspective view of another exemplary trocar having four circumferentially spaced needle guide structures and corresponding needle ports;

FIG. 20 depicts a top elevational view of the trocar of FIG. 19;

FIG. 21 depicts a side elevational view of the trocar of FIG. 19, showing suture paths extending through the needle guide structures and the corresponding needle ports;

FIG. 23C depicts a schematic side sectional view of the trocar, the suture passer guide tube, and the suture passer needle of FIG. 23B, positioned within tissue of an exemplary first thickness;

FIG. 23D depicts a schematic side sectional view of the trocar, the suture passer guide tube, and the suture passer needle of FIG. 23C, positioned within tissue of an exemplary second thickness;

Figure 1:
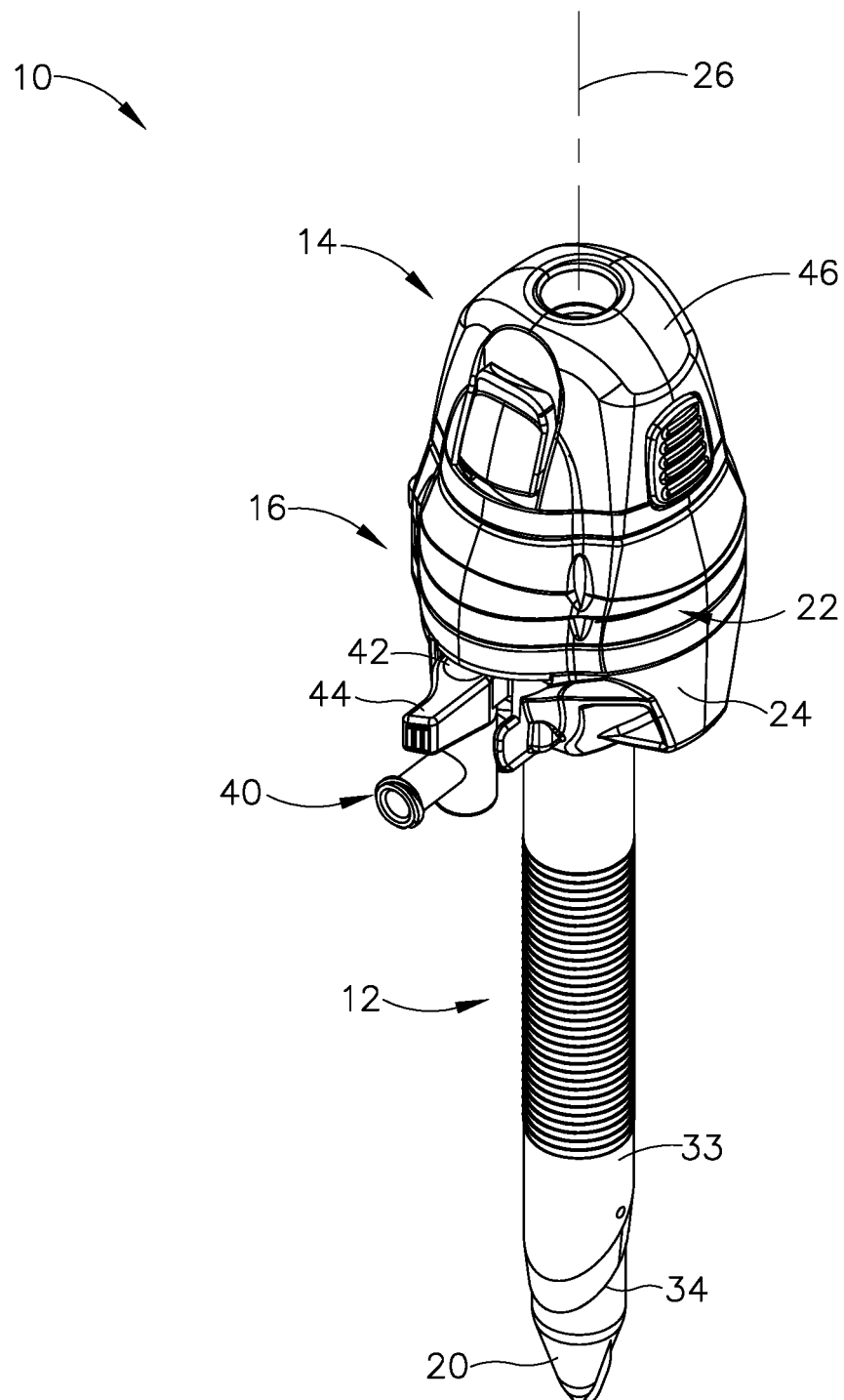
FIG. 1 depicts a perspective view of an exemplary trocar assembly.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. EXEMPLARY SURGICAL ACCESS DEVICE

Figure 2:
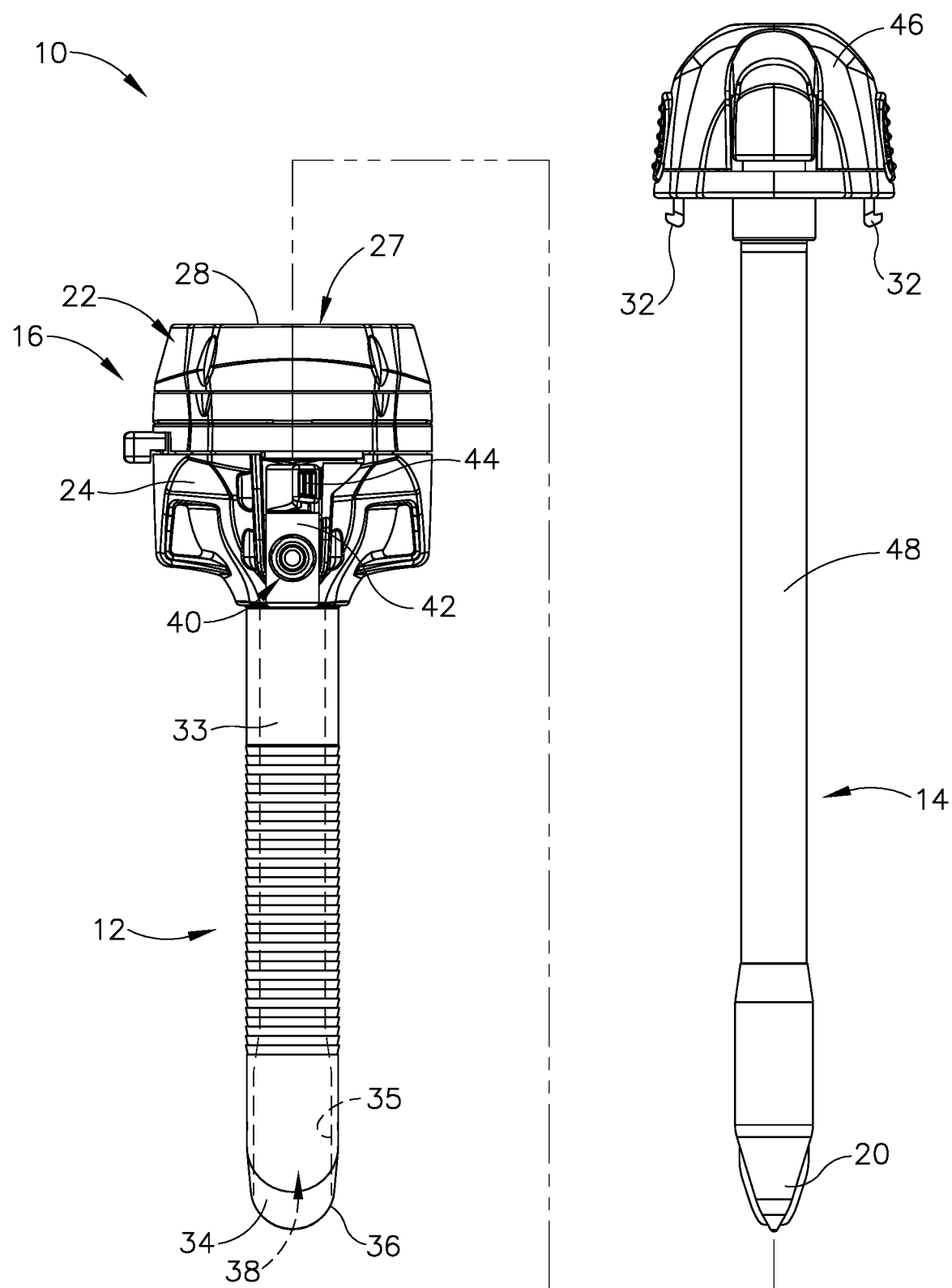
FIG. 2 depicts a partially exploded side elevational view of the trocar assembly of FIG. 1 having a trocar housing, a trocar cannula, and an obturator.

FIGS. 1-2 depict an exemplary surgical access device in the form of a first exemplary trocar assembly (10) that includes a trocar cannula (12) and a trocar obturator (14). Trocar obturator (14) is removably received within trocar cannula (12) through a trocar housing (16) of trocar cannula (12). As shown in FIG. 1 with trocar obturator (14) positioned within trocar cannula (12), a clinician inserts trocar assembly (12) through tissue (17) (see FIG. 3A) of a patient at a desirable surgical site for accessing a cavity (18) (see FIG. 3A) within the patient. By way of example only, trocar assembly (10) may be inserted in a patient's abdomen, between two of the patient's ribs, or elsewhere. A tip (20) of trocar obturator (14) projects distally from trocar cannula (12) to puncture tissue (17) (see FIG. 3A) for introducing a distal end portion of trocar cannula (12) into cavity (18) (see FIG. 3B). The clinician proximally withdraws trocar obturator (14) from trocar cannula (12) such that cavity (18) (see FIG. 3C) within the patient is in communication with a surgical environment via trocar cannula (12). The clinician may then introduce a fluid, such as a gas, through trocar cannula (12) for inflating cavity (18) (see FIG. 3A) and/or an end effector of a surgical instrument through trocar cannula (12) for engaging tissue (17) to achieve a diagnostic or therapeutic effect.

It should be understood that terms such as "proximal" and "distal" are used herein with reference to the clinician gripping trocar housing (16). Thus, tip (20) is distal with respect to the more proximal trocar housing (16). It will be further appreciated that for convenience and clarity, spatial terms such as "vertical" and "horizontal" are used herein with respect to the drawings. However, surgical instruments are used in many orientations and positions, and these terms are not intended to be limiting and absolute. Further, in some instances, components are referred to interchangeably with and without the term "assembly," e.g., a trocar and a trocar assembly. There is no particular intention for the terms to refer to different components. Likewise, terms such as "instrument" and "device" may be used interchangeably.

A. Exemplary Trocar Assembly with Cannula and Obturator

Trocar assembly (10) of FIGS. 1-2 includes cannula (12) extending distally from trocar housing (16). In the present example, trocar housing (16) has a generally cylindrical shape with a proximal removable cap (22) atop a distal housing chamber (not shown). Cap (22) is selectively attachable and detachable from housing chamber (not shown). Trocar housing (16) includes a housing sidewall (24) that extends circumferentially around a central longitudinal axis (26) through trocar assembly (10), and thus along trocar cannula (12). Trocar housing (16) further includes a central lumen (27) extending from a proximal housing end opening (28) to a distal housing end opening (not shown). As shown, cap (22) selectively mates with housing sidewall (24) via distal mating members (not shown) and further includes proximal mating members, such as slots (not shown), configured to removably connect to a pair of tabs (32), respectively, that extend distally from a portion of obturator (14). However, it will be appreciated that alternative structures and devices may also be removably connected to cap (22) during use.

Cannula (12) extends distally from trocar housing (16), and is also generally defined by a cannula sidewall (33) extending circumferentially around central longitudinal axis (26). Cannula sidewall (33) extends distally to a beveled end (34) such that cannula sidewall (33) and beveled end (34) are configured to be inserted through tissue (17) (see FIG. 3A) as discussed below in greater detail for accessing cavity (18) (see FIG. 3A). To this end, cannula (12) generally has a smaller diameter than trocar housing (16), which is configured to remain exterior of tissue (17) (see FIG. 3C). In addition, cannula (12) defines an interior lumen (35) with a proximal cannula end opening (not shown) and a distal cannula end opening (36), which extends through beveled end (34). In the present example, distal housing end opening (not shown) of trocar housing (16) fluidly connects to proximal cannula end opening (not shown) such that central lumen (27) of trocar housing (16) and interior lumen (35) of cannula (12) define a working channel (38). Working channel (38) thus extends from proximal housing end opening (28) to distal cannula end opening (36) and is configured to receive one or more surgical instruments therethrough for accessing cavity (18).

Furthermore, an insufflation port (40) is operatively connected to trocar housing (16) to control the flow of an insufflation fluid, such as carbon dioxide, through a portion of cannula (12) and into cavity (18). More particularly, insufflation port (40) includes a stopcock valve (42) and a cock valve lever (44), which can work together to allow and/or prevent passage of the insufflation fluid into tubing (not shown), through trocar housing (16), and into trocar cannula (12). Trocar housing (16) and cannula (12) respectively have proximal and distal seal assemblies (not shown) positioned within central lumen (27) and interior lumen (35) of working channel (38). In the present example, the proximal seal assembly is an instrument seal (not shown), whereas the distal seal assembly (not shown) is a zero-closure seal, such as a duckbill seal (not shown). Instrument seal (not shown) is retained within cap (22) and is configured to fluidly seal against a surgical instrument extending through working channel (38). In contrast, duckbill seal (not shown) is configured to form a seal in working channel (38) when no instrument is disposed therethrough to thereby inhibit the leakage of insufflation fluid during use. Of course, it will be appreciated that alternative seal assemblies may be positioned within working channel (38) for inhibiting such leakage of insufflation fluid.

Duckbill seal is further configured to be manipulated to provide an opening to working channel (38) that is larger than a corresponding opening provided by instrument seal. This larger opening provided by duckbill seal may facilitate extraction of bodily tissue through trocar housing (16) during a surgical procedure. In particular, cap (22) may be removed, and proximal instrument seal along with it, to expose the duckbill seal and thereby enable a surgeon to extract bodily tissue proximally through the duckbill seal opening that would otherwise be too large to extract proximally through the instrument seal opening.

As discussed briefly above, obturator (14) is used in conjunction with cannula (12) for inserting trocar assembly (10) into the patient. Obturator (14) of the present example, includes a handle head (46) with a cylindrical shaft (48) extending distally therefrom to tip (20), which is generally configured to puncture tissue (17) (see FIG. 3A) as described below in greater detail. Handle head (46) is configured to be gripped by the clinician during use and includes selectively movable tabs (32) extending distally to removably connect with trocar housing (16) for selective securement. Shaft (48) is received through working channel (38) such that tip (20) extends distally from beveled end (34). Of course, obturator (14) may be selectively removed from cannula (12) and trocar housing (16) to free working channel (38) for use. While the present example of trocar assembly (10) has obturator (14), it will be appreciated that cannula (12) may be inserted in some examples without obturator (14) or may be alternatively configured to aid insertion without using obturator (14).

B. Exemplary Method of Accessing a Cavity within a Patient

Figure 3A:
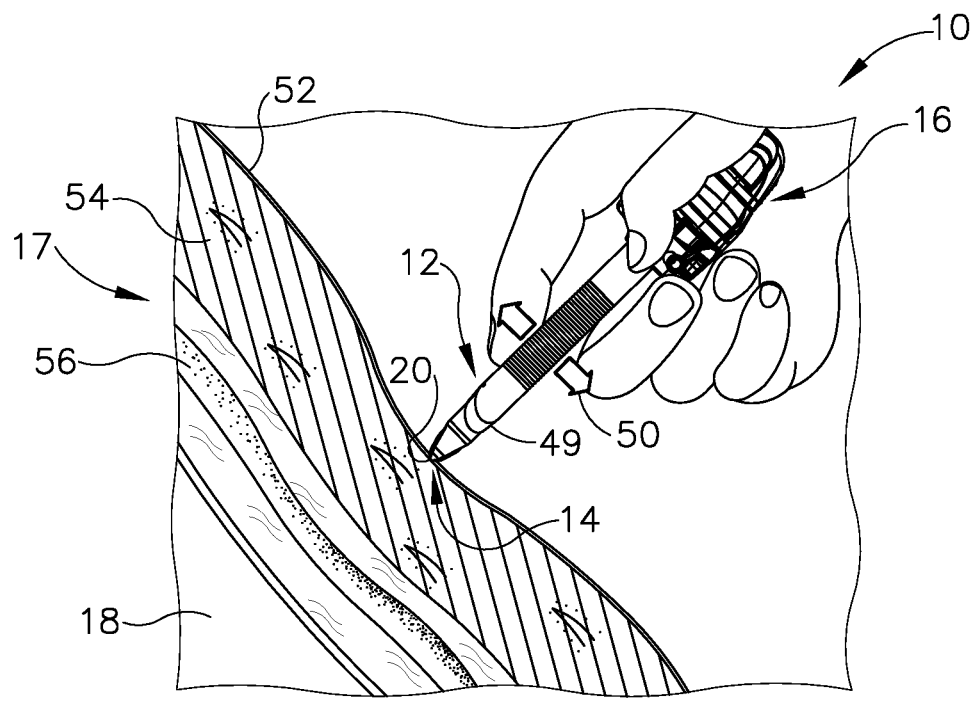
FIG. 3A depicts a side sectional view of tissue of a patient with the trocar assembly of FIG. 1 being manipulated by a clinician through the tissue.
Figure 3B:
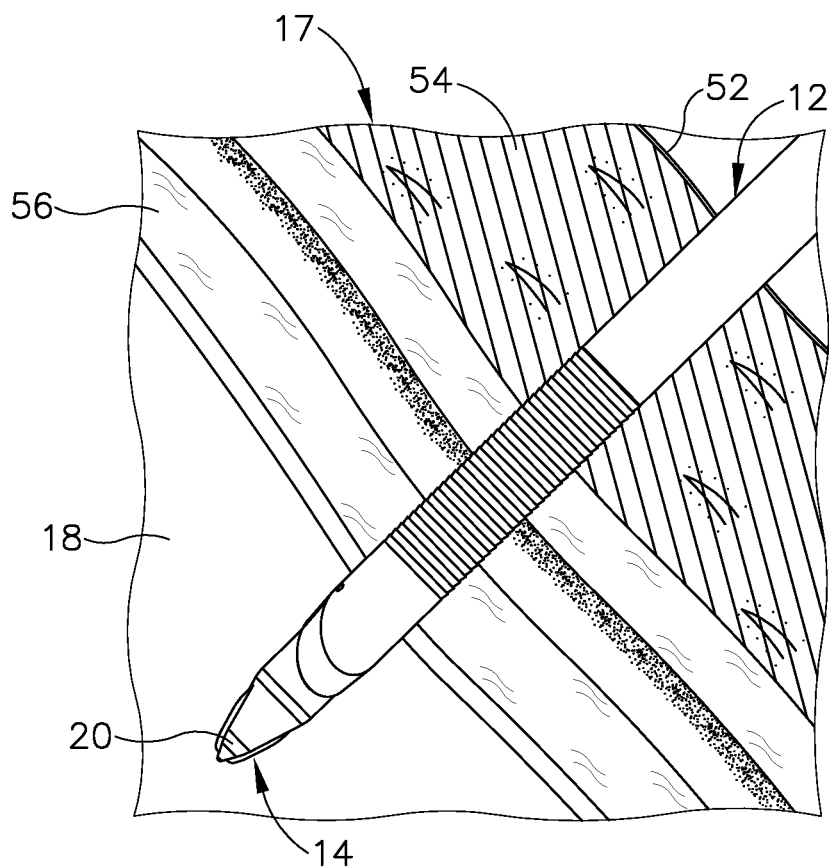
FIG. 3B depicts a side sectional view of the tissue and trocar assembly of FIG. 3A, with the trocar assembly of FIG. 1 inserted through the tissue and received within a cavity of the patient.
Figure 3C:
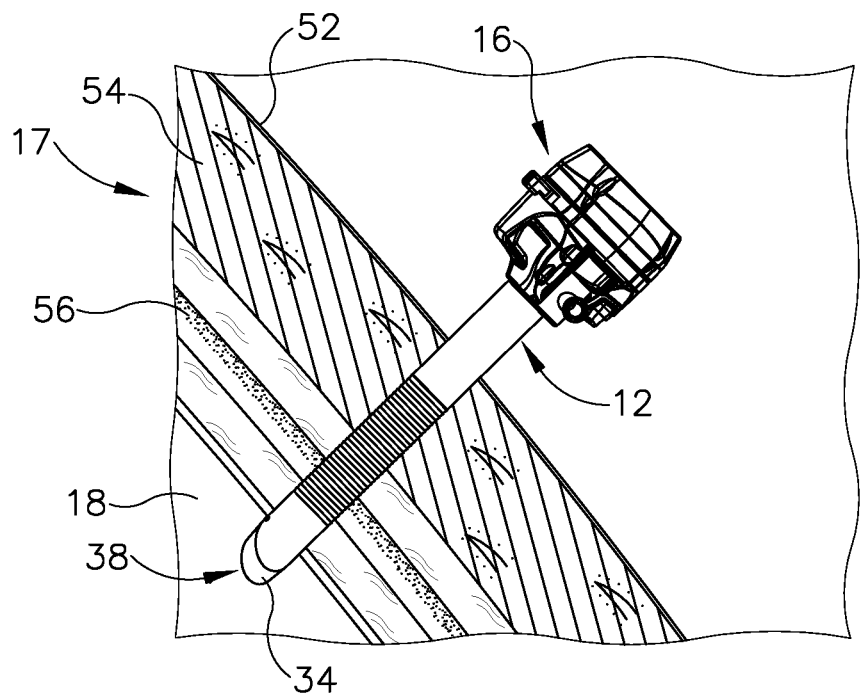
FIG. 3C depicts a side sectional view of the tissue and the trocar assembly of FIG. 3A, with the obturator withdrawn from the trocar cannula for accessing the cavity via a working channel through the trocar cannula and the trocar housing.
Figure 3D:
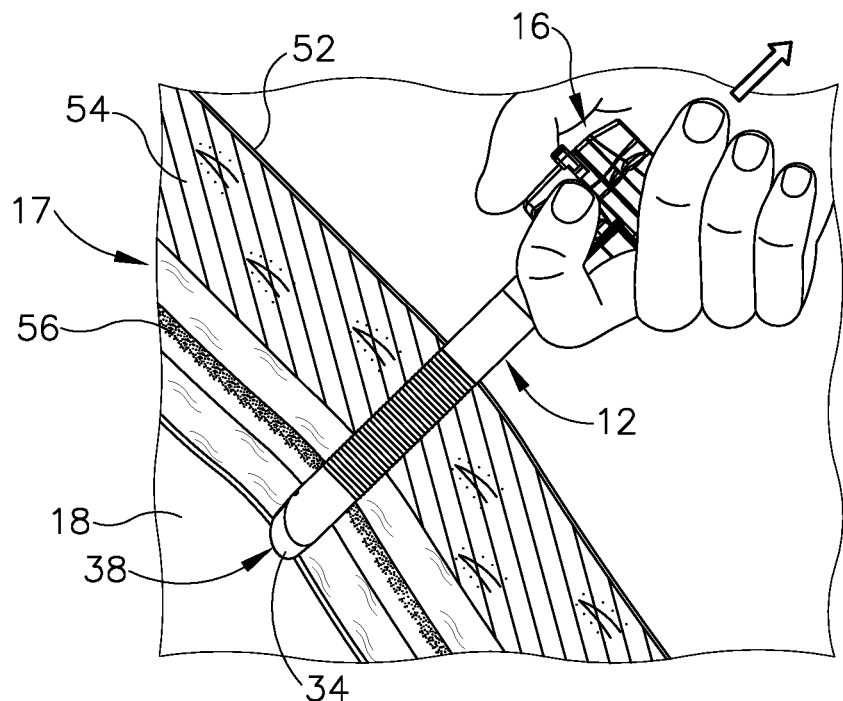
FIG. 3D depicts a side sectional view of the tissue and the trocar assembly of FIG. 3C, with the trocar housing and the trocar cannula being removed from the cavity and the tissue of the patient.

FIGS. 3A-3D illustrate accessing cavity (18) through tissue (17) with trocar assembly (10) discussed above. Tissue (17) of the present example more particularly has relatively outward superficial layers and relatively inward deep layers. Superficial layers generally include an outer layer of skin (52) and an inner layer of fat (54); whereas the deeper layers include layers of fascia (56), which are fibrous and flexible with relatively higher tensile strength than the superficial layers. As shown in FIG. 3A, with obturator (14) received within cannula (12) and connected to trocar housing (16), the clinician manipulates trocar assembly (10) to urge tip (20) of obturator (14) against skin (52) and inward toward cavity (18) while rotating trocar assembly (10) back and forth. Arrow (49) and arrow (50) respectively indicate this inward and rotatable movement. Continued inward urging of trocar assembly (10) further directs tip (20) and beveled end (34) of cannula (12) through the layers of fat (54) and fascia (56) and into cavity (18) as shown in FIG. 3B. The clinician then disconnects obturator (14) from trocar housing (16) and withdraws obturator (14) from cannula (12) to establish access from the exterior of tissue (17) into cavity (18) via working channel (38) as shown in FIG. 3C for achieving a diagnostic or therapeutic effect with another surgical instrument (not shown). Once the diagnostic or therapeutic effect is complete, clinician withdraws cannula (12) and trocar housing (16) outwardly for removal from tissue (17) as shown in FIG. 3D.

Figure 4A:
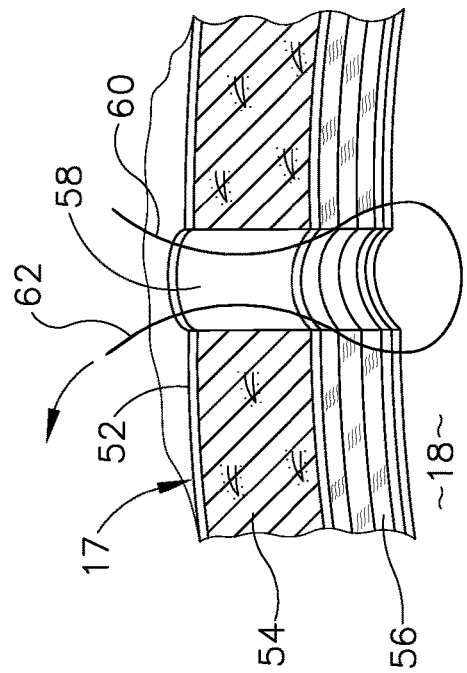
FIG. 4A depicts another side sectional view of the tissue shown in FIGS. 3A-3D following removal of the trocar assembly of FIG. 1, with an opening through the tissue and a suture thread being introduced into a portion of the tissue for suturing the opening closed.
Figure 4B:
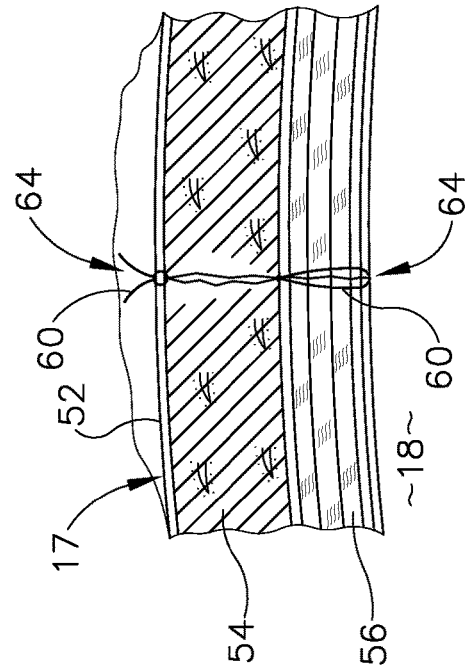
FIG. 4B depicts a side sectional view of the tissue of FIG. 4A, with the suture thread being introduced though another portion of the tissue and pulled through the tissue.
Figure 4C:
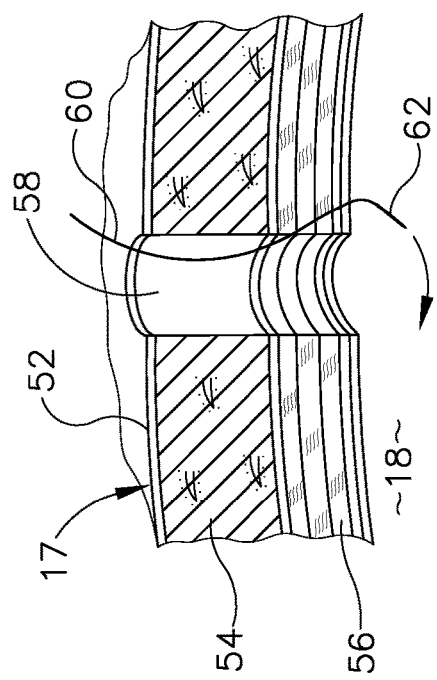
FIG. 4C depicts a side sectional view of the tissue of FIG. 4A, with the suture thread tightened and knotted for at least partially closing the opening.
Figure 4D:
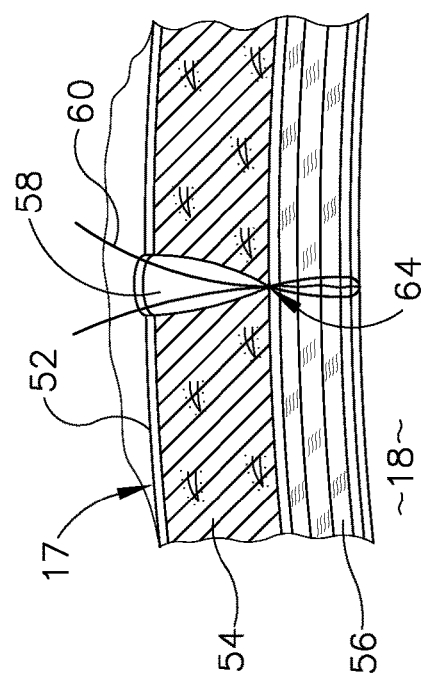
FIG. 4D depicts a side sectional view of the tissue of FIG. 4A, with additional suturing for further closing the opening.

As shown in FIG. 4A, removal of cannula (12) from tissue (17) generally results in a tissue opening (58), which may also be referred to as a tissue port or tissue wound, that clinician closes to encourage healing of tissue (17). While some tissue openings may sufficiently close as tissue (17) comes together, other openings, such as tissue opening (58), are sutured closed with a suture thread (60). In one example shown in FIGS. 4A-4D, suture thread (60) is removably coupled with a needle (62) for guiding suture thread (62) through tissue (17) as the clinician manipulates needle (62). More particularly, as shown in FIG. 4B, the clinician directs needle (62) downwardly through fascia (56) on one side of tissue opening (58) and then upwardly through fascia (56) on the other side of tissue opening (58) as needle (62) clears tissue (17). Notably, the clinician threads needle (62) though fascia (56) a desirable distance distally from tissue opening (58) in order to provide a relatively close proximity to tissue opening (58); but also at a sufficient distance to provide ample fascia (56) for anchoring suture thread (60) therein. Additionally, the clinician angles a tip of needle (62) obliquely away from a central axis of opening (58) at a suitable angle in order to achieve sufficient "bite" when anchoring suture thread (60) within fascia (56). As shown in FIG. 4C, suture thread (60) from respective sides of tissue opening (58) are brought together and pulled to similarly pull tissue (17) together and at least partially close tissue opening (58). The clinician then knots suture thread (60) to secure tissue (17) together and sufficiently close tissue opening (58) with a formed suture (64) as shown in FIG. 4D. Additional sutures (64) may be placed along tissue (17) to further close tissue opening (58) and encourage healing of tissue (17).

While the above described suturing technique shown in FIGS. 4A-4D is one exemplary procedure for closing tissue opening (58) with suture thread (60) following use of trocar assembly (10) (see FIG. 1), other exemplary procedures and devices may be alternatively used for closing such tissue openings. By way of example, U.S. patent application Ser. No. 15/088,723, entitled "Surgical Access Devices with Integrated Wound Closure Features," filed Apr. 1, 2016, issued as U.S. Pat. No. 10,299,785 on May 28, 2019, which is incorporated by reference herein in its entirety, describes an alternative trocar assembly and suturing technique. To this end, alternative trocar assemblies and suturing techniques may be used in any combination as desired by the clinician.

II. EXEMPLARY SURGICAL ACCESS DEVICE HAVING WOUND CLOSURE FEATURES

Figure 5A:
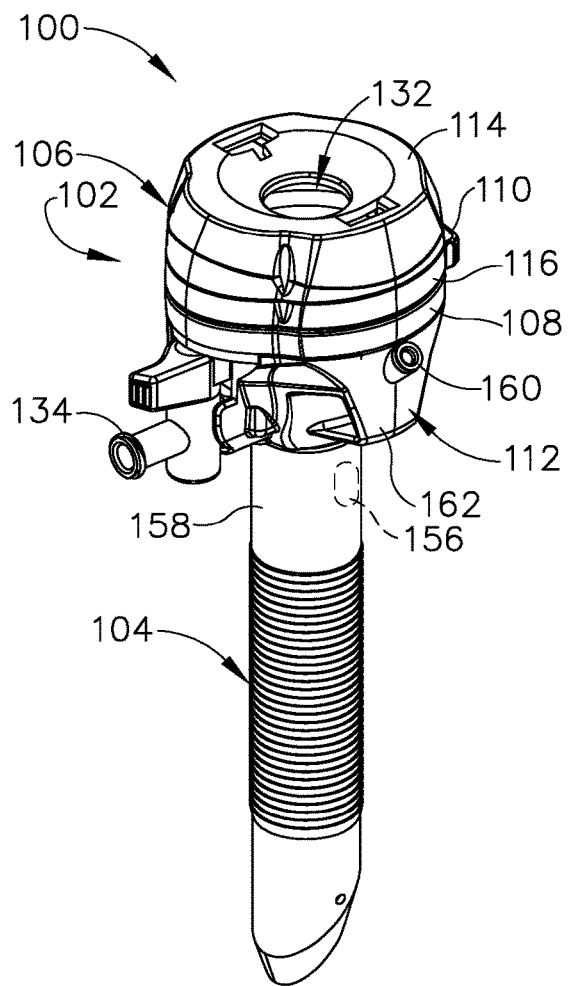
FIG. 5A depicts a front perspective view of an exemplary trocar having a housing and a cannula.
Figure 5B:
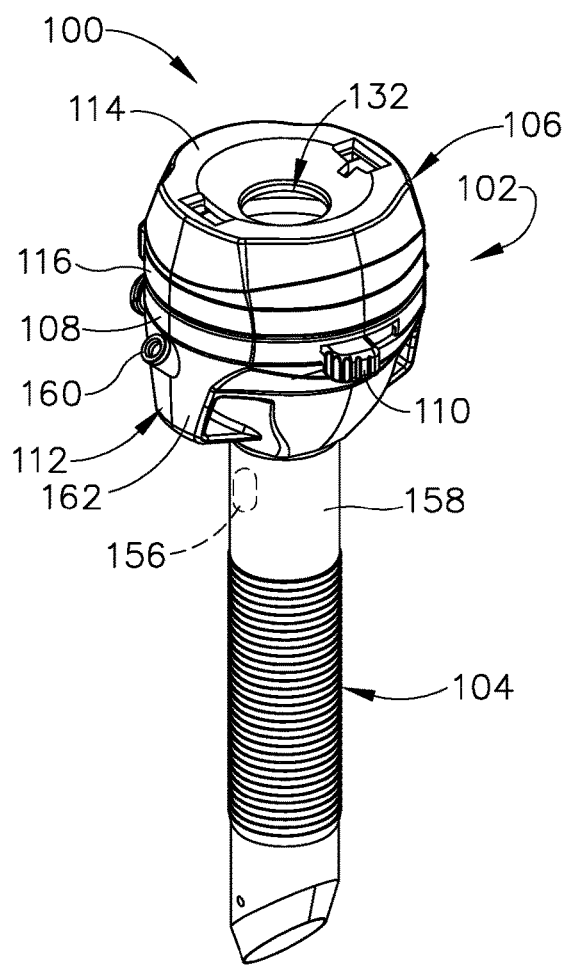
FIG. 5B depicts a rear perspective view of the trocar of FIG. 5A.
Figure 6:
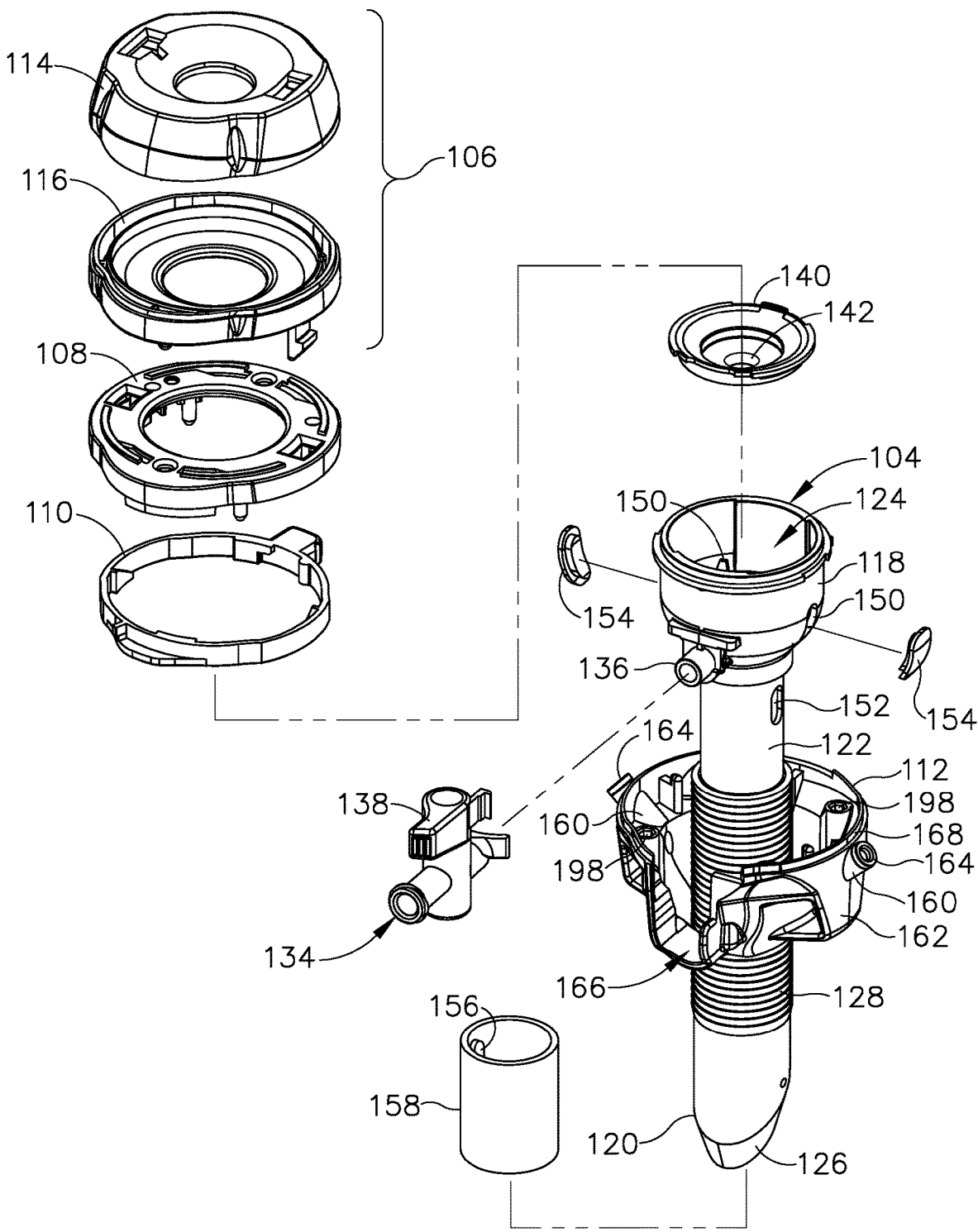
FIG. 6 depicts an exploded perspective view of the trocar of FIG. 5A.

A. Exemplary Trocar Having Latch Ring and Needle Ports Defining Oblique Suture Paths FIGS. 5A-6 show another exemplary surgical access device in the form of a trocar (100). Though not shown, those of ordinary skill in the art will recognize that trocar (100) may be used in combination with any suitable trocar obturator, such as obturator (14) described above, for example. Trocar (100) generally includes a housing (102) and a cannula (104) coupled to and extending distally from housing (102) along a central longitudinal axis of trocar (100). Housing (102) includes a proximal housing (106), a housing cap plate (108), a latch ring (110), and a distal housing (112). Proximal housing (106) has a proximal housing head (114) and a proximal housing base (116). As described in greater detail below, proximal housing (106) is coupled with and selectively releasable from the remainder of trocar (100) via housing cap plate (108) and latch ring (110). In particular, distally extending protrusions of proximal housing (106) are received through housing cap plate (108) and are releasably engaged by latch ring (110). Latch ring (110) is rotatable about a central axis of trocar (100) to selectively release the distally extending protrusions and thereby enable separation of proximal housing (102) proximally from housing cap plate (108). As described below, latch ring (110) is suitably oriented to avoid obstructing needle ports and needle guide tubes that define suture paths extending obliquely through trocar (100).

As shown in FIG. 6, cannula (104) includes a proximal hub (118), a distal tip (120), and a cylindrical body (122) extending therebetween along the central axis of trocar (100). Proximal hub (118) flares radially outwardly from cylindrical body (122) in a proximal direction and defines a proximal opening to a cannula lumen (124), while distal tip (120) defines a distal opening to cannula lumen (124). Distal tip (120) itself is beveled and includes a chamfered edge (126) to facilitate insertion of distal tip (120) through tissue and into a patient body cavity during a surgical procedure. An outer surface of cylindrical body (122) may be provided with a plurality of tissue engagement ribs (128) or other similar features suitable to frictionally engage the inner wall of a tissue opening through which cannula (104) is received into the body cavity.

Referring briefly to FIG. 11, cannula lumen (124) fluidly communicates with an interior (130) of housing (102) to collectively define a working channel (132) extending through trocar (100) along the central axis thereof. A distal opening to working channel (132) is defined by distal tip (120) of cannula (104), and a proximal opening to working channel (132) is defined by proximal housing head (114). In configurations in which proximal housing (106) is decoupled from the remainder of trocar (100), for example as described below with reference to FIG. 10B, the proximal opening to working channel (132) is defined by housing cap plate (108). Working channel (132) is configured to receive one or more surgical instruments therethrough, such as a variety of endoscopic surgical instruments for example, for accessing the patient body cavity and observing and/or treating tissue accessible therein.

As shown in FIG. 6, an insufflation port (134) (or "stopcock") is operatively connected to proximal hub (118) of cannula (104) at fitting (136), and includes an internal valve (not shown) similar to valve (42) and a valve lever (138). Insufflation port (134) may be formed integrally with fitting (136), or alternatively coupled to fitting (136) during assembly of trocar (100). Insufflation tubing (not shown) is coupled to an inlet of insufflation port (134) and directs insufflation fluid, such as carbon monoxide, from a fluid source into insufflation port (134), which directs the fluid distally through working channel (132) into the patient body cavity. Valve lever (138) is configured to rotate the internal valve (not shown) between open and closed positions to control the flow of insufflation fluid through insufflation port (134).

Similar to trocar assembly (10), trocar (100) may include a proximal (or "outer") seal assembly and/or a distal (or "inner") seal assembly each arranged within working channel (132). In the present example, trocar (100) includes a distal seal assembly in the form of an instrument seal (140) arranged within a distal tapered portion of proximal hub (118). Distal instrument seal (140) includes a central opening (142) configured to receive a surgical instrument therethrough, and is configured to sealingly engage an outer surface of a surgical instrument extending through central opening (142) to prevent proximal advancement of bodily fluids and/or tissue into interior (130) of housing (102). In exemplary configurations, instrument seal (140) may be configured to absorb or otherwise remove bodily fluids from the outer surface of the surgical instrument as the surgical instrument is retracted proximally through instrument seal (140). Though not shown, trocar (100) may further include a proximal seal assembly arranged within proximal housing (106).

Those of ordinary skill in the art will recognize that trocar (100) may include proximal and/or distal seal assemblies of various alternative configurations, such as those disclosed in U.S. patent application Ser. No. 15/088,723, issued as U.S. Pat. No. 10,299,785 on May 28, 2019 incorporated by reference above. For instance, though not shown, trocar (100) may include a proximal seal assembly in the form of an instrument seal arranged within proximal housing (106), and a distal seal assembly in the form of a zero-closure seal, such as a duckbill seal, arranged within proximal hub (118) of cannula (104). As described above with reference to trocar assembly (10), such a zero-closure seal is generally configured to form a fluid-tight seal in working channel (132) and thereby maintain insufflation even when no surgical instrument is present in working channel (132). Furthermore, the distal zero-closure seal may be manipulated to provide an opening to a distal portion of working channel (132) (e.g., cannula lumen (124)) that is large enough to enable extraction of tissue proximally therethrough, particularly when proximal housing (106) is removed from trocar (100) to provide access to the distal zero-closure seal.

As shown in FIG. 6, trocar (100) further includes a plurality of needle ports formed in select side portions of cannula (104). As described in greater detail below, each needle port is configured to direct a suture passer needle (or simply "suture passer") across working channel (132) of trocar (100) at an oblique angle relative to the central axis of trocar (100) (see FIG. 11) to thereby establish an oblique suture path extending through trocar (100) and adjacent tissue. As used herein, the term "oblique" means neither parallel nor perpendicular to the referenced axis, such as the central axis of trocar (100).

In the present example, trocar (100) includes a pair of needle entrance ports (150) and a corresponding pair of needle exit ports (152) arranged distally of needle entrance ports (150). Needle entrance ports (150) extend through respective side portions of proximal hub (118) of cannula (104) at diametrically opposed positions, and open to cannula lumen (124). Needle exit ports (152) extend through respective side portions of cylindrical body (122) of cannula (104) at diametrically opposed positions, and open to cannula lumen (124). Each needle port (150, 152) is generally elongate along the central axis of trocar (100), though needle ports (150, 152) may be formed with various other shapes in alternative configurations.

Each needle entrance port (150) is configured to cooperate with an opposing needle exit port (152) to direct a suture passer needle along a respective oblique suture path. In particular, a needle entrance port (150) on a first side of cannula (104) cooperates with a needle exit port (152) on an opposing second side of cannula (104) to define a first oblique suture path. Similarly, a needle entrance port (152) on the second side of cannula (104) cooperates with a needle exit port (152) on the opposing first side of cannula (104) to define a second oblique suture path. In the present example, each needle exit port (152) is positioned in circumferential alignment with the adjacent needle entrance port (150), such that the resulting oblique suture paths define an X-shaped pattern in a single suture plane extending along the central axis of trocar (100). In other examples, needle entrance ports (150) and/or needle exit ports (152) may be arranged in a non-diametrically opposed configuration, and/or needle exit ports (152) may be circumferentially offset from needle entrance ports (150), such that the resulting oblique suture paths lie in separate suture planes.

Each needle exit port (152) may be spaced distally from its respective needle entrance port (150) by a distance suitable to achieve a desired suture path angle (or "tissue bite angle") measured between the resulting suture path and the central axis of trocar (100). In the present example, each needle exit port (152) is spaced distally from its respective needle entrance port (150) by the same axial distance, such that the resulting suture paths exhibit the same suture path angles. In other examples, however, needle exit ports (152) may be spaced distally at different distances to achieve different suture path angles. Moreover, in various other examples, any suitable quantity and arrangement of needle entrance ports (150) and needle exit ports (152) may be provided.

Each needle port (150, 152) is provided with a pierceable seal configured to aid in maintaining insufflation when a suture passer needle is directed through trocar (100) along the suture paths, and/or when the suture passer needle is withdrawn from trocar (100). In the present example, each needle entrance port (150) is provided with an entrance seal shown in the form of an elongate plug (154), and each needle exit port (152) is provided with an exit seal shown in the form of an elongate protrusion (156) projecting radially inwardly from an inner surface of a cannula sleeve (158). Each seal (154, 156) is shaped to sealingly engage its respective needle port (150, 152). As shown in FIGS. 5A-6, cannula sleeve (158) is received over a narrowed region of cylindrical body (122) of cannula (104), and has an outer diameter similar to an outer diameter of a distal region of cylindrical body (122) located distally of tissue engagement ribs (128). In exemplary configurations, plugs (154) and cannula sleeve (158), including protrusions (156), and may be formed of an elastomeric material. Additionally, cannula sleeve (158) may be overmolded over cannula (104) during manufacture.

Trocar (100) further includes a pair of needle guide structures shown in the form of guide tubes (160), each configured to guide a suture passer needle along the oblique suture path defined by the respective pair of needle entrance and exit ports (150, 152), described above. In the present example, needle guide tubes (160) are formed integrally with distal housing (112) and extend angularly through side wings (162) of distal housing (112). Each needle guide tube (160) includes a proximal opening through which a suture passer needle is introduced, and a distal opening that confronts seal plug (154) of a respective needle entrance port (150), as shown in FIG. 11. Additionally, the entrance opening of each needle guide tube (160) includes a seal cap (164). As described in greater detail below with reference to FIGS. 12A and 12B, seal caps (164) are pierceable by a suture passer needle and function in a manner similar to seal plugs (154) to assist in maintaining insufflation during a surgical procedure. While the needle guide structures of the present example are shown in the form of needle guide tubes (160), it will be appreciated that in alternative examples various other structures suitable to guide a suture passer needle along the oblique suture paths of trocar (100) may be employed instead. In other examples, such needle guide structures may be omitted from trocar (100).

As shown in FIGS. 5A-6, distal housing (112) is in the form of a generally annular shell shaped to receive and encircle proximal hub (118) of cannula (104). A sidewall of distal housing (112) includes a cutout (166) that accommodates insufflation port (134), which extends radially outwardly from proximal hub (118). As described above, distal housing (112) includes a pair of diametrically opposed side wings (162) that support needle guide tubes (160). During a surgical procedure, side wings (162) may be gripped by a surgeon when introducing trocar (100) through patient tissue. An upper edge (168) of distal housing (112) supports housing cap plate (108) and latch ring (110).

Figure 7A:
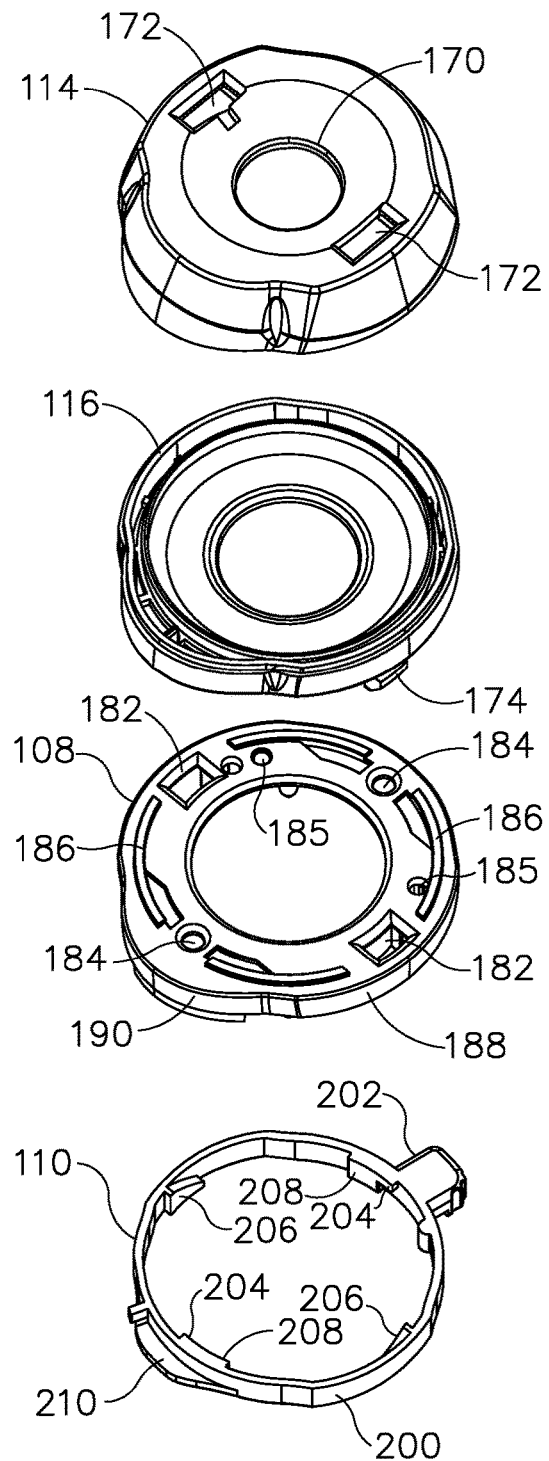
FIG. 7A depicts an exploded top perspective view of a portion of the trocar housing of FIG. 5A.
Figure 7B:
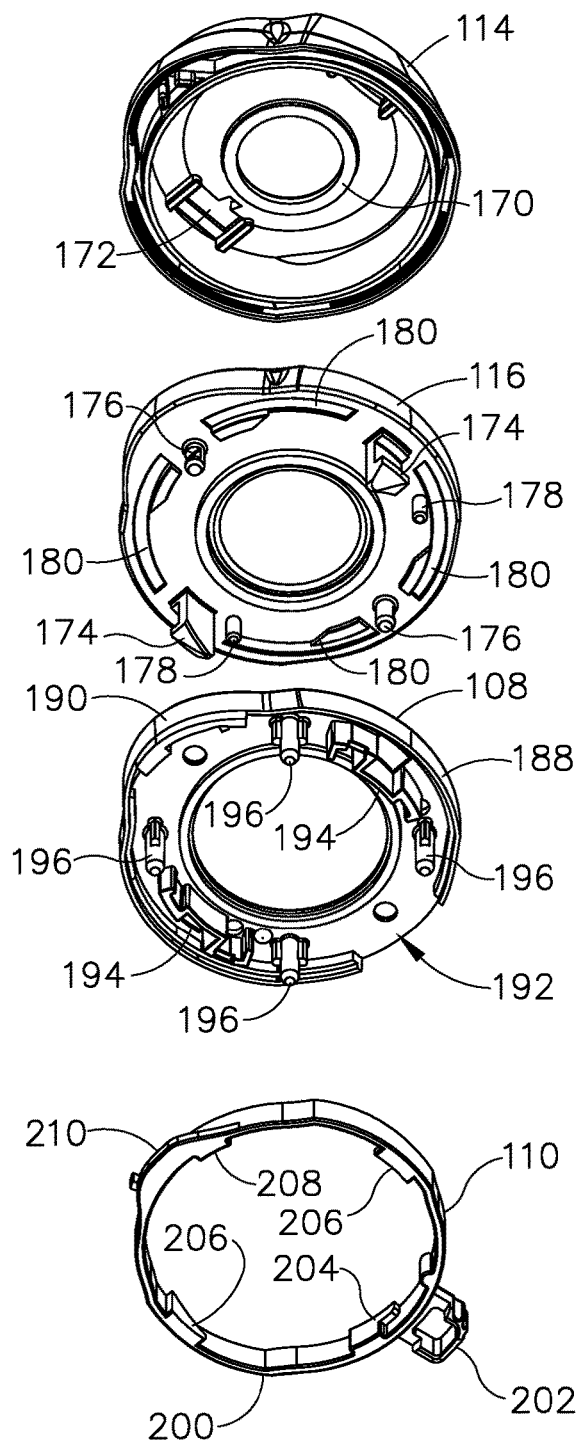
FIG. 7B depicts an exploded bottom perspective view of the housing portion of FIG. 7A.
Figure 8:
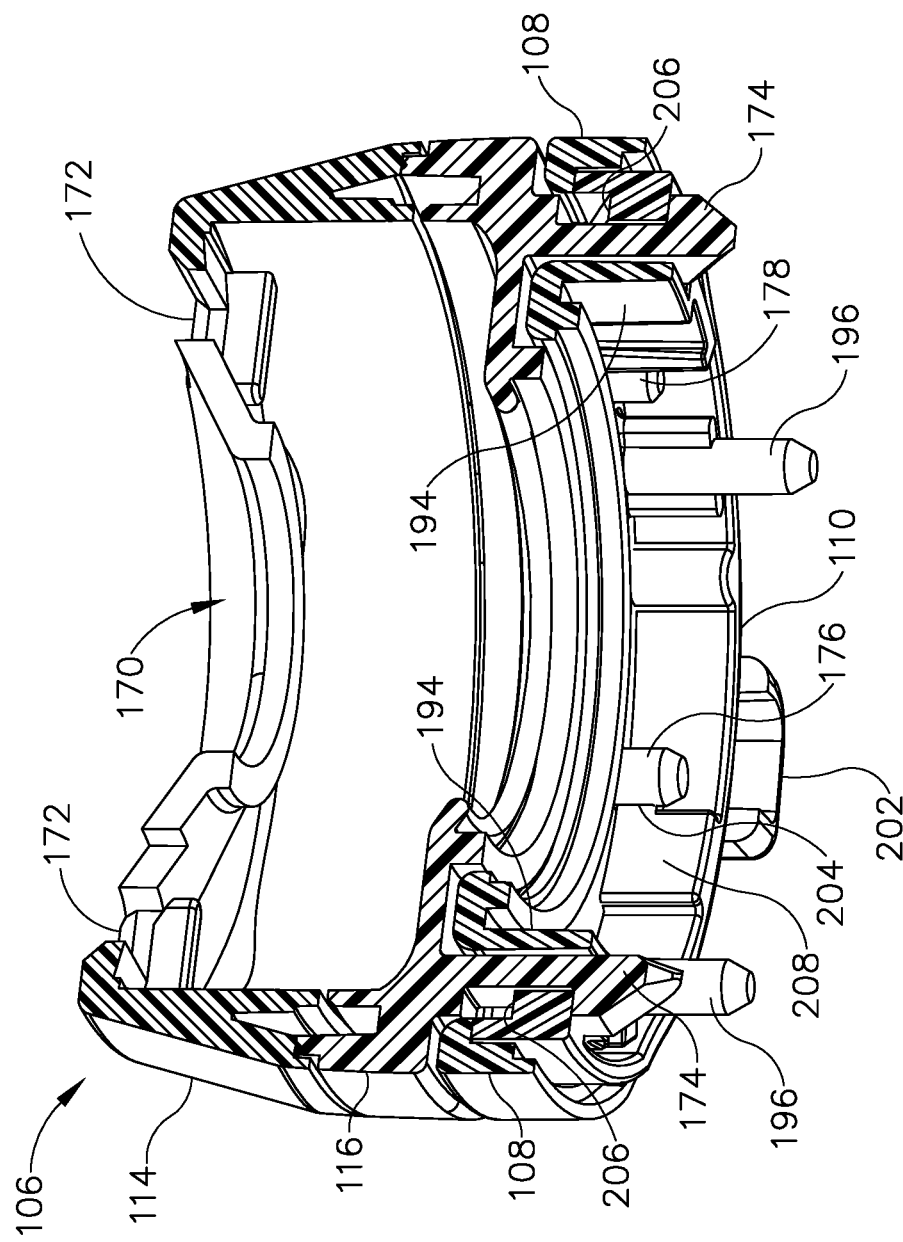
FIG. 8 depicts an assembled side sectional perspective view of the housing portion of FIG. 7A.

FIGS. 7A-8 show additional details of proximal housing head (114), proximal housing base (116), housing cap plate (108), and latch ring (110). Proximal housing head (114) includes a central opening (170) that defines a proximal end of working channel (132) of trocar (100). Proximal housing head (114) further includes a pair of slots (172) configured to receive a corresponding pair of tabs extending distally from the proximal head of an obturator, such as tabs (32) of obturator (14), for releasably connecting the obturator to trocar (100). Proximal housing head (114) is supported by and coupled to proximal housing base (116), for example by a snap-fit connection. Though not shown, a proximal seal assembly, such as an instrument seal, may be arranged between proximal housing head and proximal housing base (116). Such a proximal seal assembly may cooperate with distal seal assembly (140), described above, to ensure a sealing engagement between trocar (100) and a surgical instrument inserted through trocar (100) while maintaining insufflation.

As described below, proximal housing (106), defined by proximal housing head (114) and proximal housing base (116), is configured to couple with and selectively decouple from the remaining distal portion of trocar (100) via operation of latch ring (110) in combination with housing cap plate (108). In that regard, proximal housing base (116) further includes a plurality of distally extending mating features configured to facilitate attachment and release of proximal housing (106) from housing cap plate (108) and latch ring (110). In particular, an underside of proximal housing base (116) includes a pair of latching tabs (174), a pair of latching posts (176), a pair of guide pins (178), and a plurality circumferentially extending arcuate recesses (180). In the present example, four arcuate recesses (180) are provided in respective quadrants of the underside of proximal housing base (116). Additionally, latching tabs (174) are arranged at diametrically opposed positions along a first transverse axis, and latching tabs (174) are arranged at diametrically opposed positions along a second transverse axis that is perpendicular to the first transverse axis. Each guide pin (178) is positioned circumferentially between a latching tab (174) and an adjacent latching post (176). In other examples, various alternative quantities and arrangements of latching tabs (174), latching posts (176), guide pins (178), arcuate recesses (180), and/or other like mating features, and corresponding mating features of housing cap plate (108) and latch ring (110) described below, may be provided.

As shown in FIG. 7A, housing cap plate (108) includes a plurality of mating features configured and positioned to receive the above-described features of proximal housing base (116) to promote coupling and rotational alignment of proximal housing (106) with housing cap plate (108) and latch ring (110). In particular, housing cap plate (108) includes a pair of tab slots (182) configured to receive latching tabs (174) therethrough, a pair of post bores (184) configured to receive latching posts (176) therethrough, a pair of pin bores (185) configured to receive guide pins (178) therethrough, and a plurality of circumferentially extending arcuate ribs (186) configured to seat within arcuate recesses (180). As described above, various alternative quantities and arrangements of these mating features may be provided in other examples.

Housing cap plate (108) further includes a downwardly depending sidewall (188) extending about an outer perimeter of housing cap plate (108). A section of sidewall (188) bulges radially outwardly to define a nose portion (190) of housing cap plate (108) that is centered on the axis along which post bores (184) and latching posts (176) are arranged. As shown in FIG. 5A, nose portion (190) aligns with and overhangs a portion of insufflation port (134). As shown in FIG. 7B, housing cap plate (108) further includes a circumferentially extending slot (192) formed in sidewall (188) at a location opposite of nose portion (190). Slot (192) is configured to expose a user engagement feature projecting radially outwardly from latch ring (110), as described below.

As shown in FIGS. 7B and 8, an underside of housing cap plate (108) includes a pair of distally extending tab retaining walls (194) aligned with tab slots (182) and configured to abut and circumferentially constrain latching tabs (174) when tabs (174) are inserted through tab slots (182). The underside of housing cap plate (108) additionally includes a plurality of distally extending coupling posts (196) configured to be received by a corresponding plurality of coupling bores (198) formed on distal housing (112), as shown in FIG. 6, for coupling housing cap plate (108) with distal housing (112). In exemplary configurations, coupling posts (196) and coupling bores (198) may be suitably shaped and sized respectively to couple with a press-fit or a snap-fit engagement.

As shown in FIGS. 7A-8, latch ring (110) includes an annular body (200) and a user engagement feature in the form of a knob (202) projecting radially outwardly from annular body (200). Latch ring (110) further includes a plurality of latching features projecting radially inwardly from annular body (200). In particular, latch ring (110) includes a pair of latching arms (204) arranged at diametrically opposed positions along a first transverse axis, and a pair of cam ramps (206) arranged at diametrically opposed positions along a second transverse axis that is generally perpendicular to the first transverse axis. Each latching arm (204) extends circumferentially from an adjoining base (208) that may function as a secondary rotational stop for latch ring (110), as described below. Latch ring (110) additionally includes an arcuate fin (210) configured to be received and move circumferentially within nose portion (190) of housing cap plate (108). Knob (202) and arcuate fin (210) are generally diametrically opposed from one another across annular body (200).

Latch ring (110) is arranged distally of housing cap plate (108) and is housed radially inwardly of housing cap plate sidewall (188) at a proximal end, as best shown in FIG. 8, and radially inwardly of distal housing (112) at a distal end, as shown in FIG. 11. Latch ring (110) is rotatable about the central axis of trocar (100) between a latched position (see FIG. 9A) in which the latching features of latch ring (110) capture the distally extending features of proximal housing base (116), and an unlatched position (see FIG. 10A) in which the latching features of latch ring (110) release the distally extending features of proximal housing base (116) to thereby allow proximal detachment of proximal housing (106). Latch ring (110) is movable between the latched and unlatched positions by knob (202), which projects radially through circumferential slot (192) of housing cap plate (108) and is movable circumferentially therein as latch ring (110) rotates about the trocar central axis. In particular, circumferential slot (192) may define the rotational range of latch ring (110) such that a first end of slot (192) defines the latched position and a second end of slot (192) defines the unlatched position. In various configurations, proximal housing base (116), housing cap plate (108), and latch ring (110) may be suitably configured to define any desired rotational range of latch ring (110) relative to proximal housing base (116) and housing cap plate (108), which remain rotationally fixed.

FIG. 8 shows latch ring (110) in an exemplary latched position. As latch ring (110) is rotated into this latched position, from an unlatched position, each cam ramp (206) is received within an outwardly facing notch of a respective latching tab (174) of proximal housing base (116). Simultaneously, each latching arm (204) is received within an outwardly facing notch (see FIG. 7B) of a respective latching post (176) of proximal housing base (116). As latch ring (110) is rotated further toward the latched position, the sloped surface of each cam ramp (206) engages a proximal notch wall of the respective latching tab (174), and the latching arms (204) advance further within the notches of their respective latching posts (176), thereby securing proximal housing (106) axially against housing cap plate (108). Latch ring (110) may be rotated in the opposite direction to disengage cam ramps (206) from latching tabs (174) and latching arms (204) from latching posts (176), to thereby enable proximal detachment of proximal housing (106) from the remaining distal portion of trocar (100).

Rotation of latch ring (110) between the latched and unlatched positions is limited by direct contact of latch ring knob (202) with the ends of circumferential slot (192) formed in housing cap plate (108), which serves as a primary rotational stop. One or more secondary rotational stops may also be provided. For example, a side surface of each latching arm base (208) is configured to abut a respective latching post (176) of proximal housing base (116), and a first end of fin (210) is configured to abut a corresponding first inner surface of distal housing (112) (see FIG. 9A), to prevent rotation of latch ring (110) beyond the latched position. A second end of fin (210) may be configured to abut a corresponding second inner surface of distal housing (112) (see FIG. 10A) to prevent rotation of latch ring (110) beyond the unlatched position. Though not shown, latch ring (110) may be coupled with a resilient member configured to bias latch ring (110) toward the latched position.

FIGS. 9A-10B show rotation of latch ring (110) relative to the remainder of trocar (100), including proximal housing base (116) and housing cap plate (108), between the latched position (FIGS. 9A-9B) and the unlatched position (FIGS. 10A-10B). FIG. 9A shows latch ring (110) in the latched position in which cam ramps (206) and latching arms (204) engage latching tabs (174) and latching posts (176), respectively, of proximal housing base (116). As shown in FIG. 9B, this position of latch ring (110) maintains proximal housing (106) in axial engagement with the remaining distal portion of trocar (100). FIG. 10A, by comparison, shows latch ring (110) after having been rotated to the unlatched position such that cam ramps (206) and latching arms (204) disengage latching tabs (174) and latching posts (176), respectively. As shown in FIG. 10B, this position of latch ring (110) enables proximal housing (106) to be removed proximally from the remaining distal portion of trocar (100).

As shown in FIGS. 9A and 10A, needle guide tubes (160) are oriented at diametrically opposed positions along a first axial plane (P1) extending along and through (i.e., containing) the central axis of trocar (100). Additionally, latch ring (110) is oriented such that knob (202) is movable within circumferential slot (192) along a circumferential path having a midpoint (M) that is diametrically opposed from insufflation port (134) along a second axial plane (P2) extending along and through the central axis of trocar (100). In the present example, first axial plane (P1) and second axial plane (P2) are perpendicular to one another. Accordingly, path midpoint (M) is spaced circumferentially equidistantly between needle guide tubes (160) and their respective needle ports (150, 152); specifically, at approximately 90 degrees in the present example. Consequently, latch ring knob (202) remains circumferentially spaced (or "offset") from needle guide tubes (160) and needle ports (150, 152) throughout the full range of permissible rotation of latch ring (110). Advantageously, this configuration prevents undesirable interference between knob (202) and a suture passer needle being directed through needle guide tubes (160) and needle ports (150, 152), as shown in FIG. 11.

As used herein with reference to various first and second structures or reference points, such as path midpoint (M) and insufflation port (134) described above, the term "diametrically opposed" encompasses but is not limiting to a configuration in which the referenced structures or reference points are located at the same longitudinal location along the central axis of trocar (100). Indeed, in the present example shown throughout FIGS. 5A-10B, path midpoint (M) for latch ring knob (202) is spaced proximally from insufflation port (134), though midpoint (M) and port (134) are still understood to be diametrically opposed from one another along axial plane (P2), shown in FIGS. 9A and 10A.

Those of ordinary skill in the art will recognize that various other configurations of housing (102) and cannula (104) as described above may be provided such that latch ring knob (202) remains circumferentially spaced (or "offset") from needle guide tubes (160) and needle entrance ports (150) throughout the full range of permissible rotation of latch ring (110). In such alternative configurations, midpoint (M) of the circumferential path along which knob (202) travels may or may not be spaced circumferentially equidistantly between needle guide tubes (160) and needle entrance ports (150). In various examples, path midpoint (M) may be circumferentially spaced from one or more of needle guide tubes (160) and the respective needle entrance port (150) by less than, greater than, or equal to 90 degrees. Furthermore, in other examples as described above, needle guide tubes (160) and their respective needle entrance ports (150), and/or needle exit ports (152), may be positioned in non-diametrically opposed arrangements.

FIG. 11 shows a side sectional view of trocar (100) with an exemplary suture passer needle (220) inserted therethrough along an oblique suture path extending through needle guide tube (160), needle entrance port (150), across working channel (132), and through needle exit port (152). As described above, each oblique suture path passing through trocar (100) includes a plurality of pierceable seals, including a guide tube entrance seal (164), a needle entrance port seal (154), and a needle exit port seal (156). Each seal (154, 156, 164) is configured to assist in maintaining insufflation when suture passer needle (220) is inserted through trocar (100) along the suture path, and/or when suture passer needle (220) is withdrawn from trocar (100).

As described above, the guide tube entrance seals of the present example are shown in the form of seal caps (164). FIG. 12A shows additional details of seal cap (164), which includes a cylindrical body (222) and a proximal rim (224) defining a proximal opening to seal cap (164). Cylindrical body (222) is formed with an outer diameter sized to be received within a proximal end of a needle guide tube (160), and includes a closed distal end that is pierceable by suture passer needle (200), as shown in FIG. 11. Cylindrical body (222) and proximal rim (224) define an inner dimeter sized to sealingly engage an outer surface of suture needle passer (220) upon insertion through trocar (100).

FIG. 12B shows another exemplary seal cap (230) having a body (232) and a proximal rim (234) defining a proximal opening to seal cap (230). Body (232) may be in the form of a duckbill seal or a tab having a closed distal end, for example. Proximal rim (234) defines a first inner dimension of seal cap, and body (232) defines a second smaller inner dimension of seal cap (230). In some variations, the second inner dimension defined by body (232) may taper distally. Seal caps (164, 230) described above may be formed separately from housing (102) and cannula (104) and assembled with needle guide tubes (160) during manufacture of trocar (100). In other examples, seal caps (164, 230) may be co-molded with needle guide tubes (160) in a single operation.

B. Exemplary Needle Guide Tubes

Figure 13:
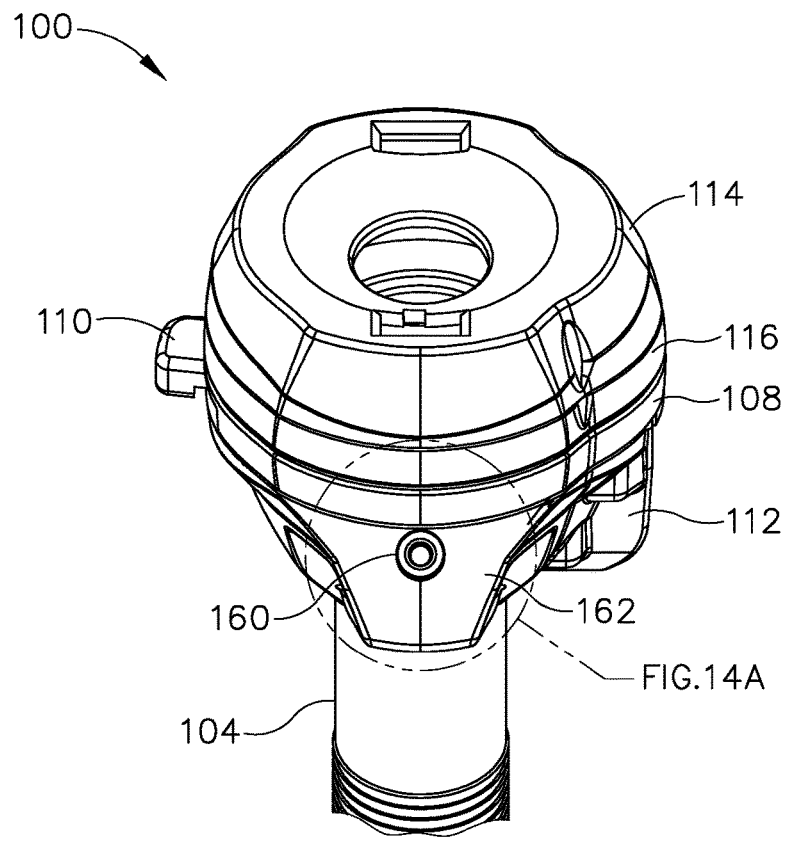
FIG. 13 depicts a side perspective view of the trocar of FIG. 5A.
Figures 14A, 14B, 14C:
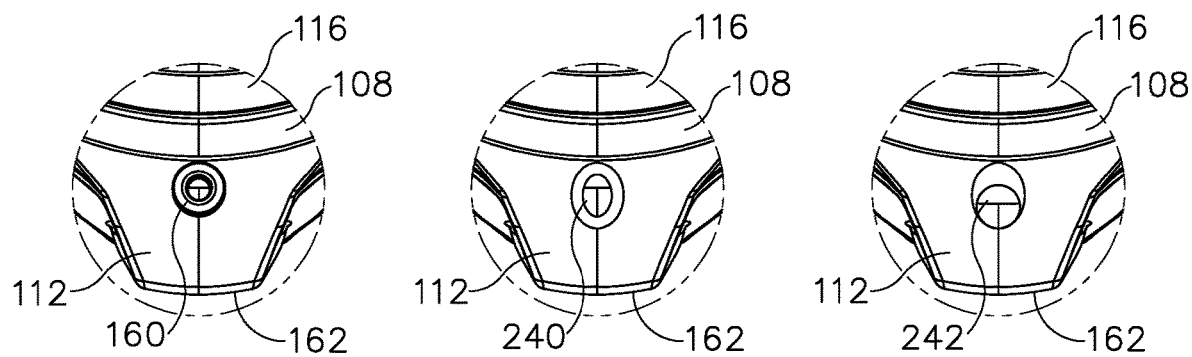
FIG. 14A depicts an enlarged perspective view of a region indicated in FIG. 13, showing details of a needle guide tube of the trocar.
FIG. 14B depicts an enlarged perspective view showing details of a needle guide tube shaped according to an exemplary variation of the needle guide tube of FIG. 14A.
FIG. 14C depicts an enlarged perspective view showing details of a needle guide tube shaped according to another exemplary variation of the needle guide tube of FIG. 14A.

FIGS. 13 and 14A show additional details of needle guide tubes (160) of trocar (100). In the present example, needle guide tubes (160) are formed with a generally circular cross-section. In other examples, needle guide tubes (160) may be formed with various alternatively shaped cross-sections to facilitate insertion of suture passer needles. For example, FIG. 14B shows an exemplary alternative configuration in which distal housing (112) is provided with needle guide tubes (240) having a generally oval cross-section. FIG. 14C shows another exemplary configuration in which distal housing (112) is provided with needle guide tubes (242) having entrance ends that are recessed inwardly within an outer surface of side wings (162), which may also serve to ease insertion of suture passer needles. Guide tubes (242) may be provided with any suitably shaped cross-section, such as a circular cross-section, for example.

C. Exemplary Suturing Procedure Using Trocar Having Needle Ports

FIGS. 15A-15E schematically illustrate steps of an exemplary procedure for suturing closed an opening (58) (see FIG. 15D) formed in tissue (17) by trocar (100) during insertion for accessing body cavity (18). Advantageously, the features of trocar (100) described above enable a surgeon to leave trocar (100) in place within opening (58) and use trocar (100) as a needle guide mechanism for directing suture thread (250) distally through tissue (17) and into cavity (18) at desired suture angles to achieve an appropriate degree of "tissue bite" in lower fascia layers (56) of tissue (17). As used herein, the term "tissue bite" refers to the amount of tissue (17) captured by a suture thread. In the present context, tissue bite is defined by a distance (X) (see FIG. 15E) measured perpendicularly from the inner wall of tissue opening (58), which may coincide with the outer surface of cannula (104), to the point at which a suture passer needle and thus suture thread (250) exits distally from fascia (56) into body cavity (18).

Figures 15A, 15B, 15C:
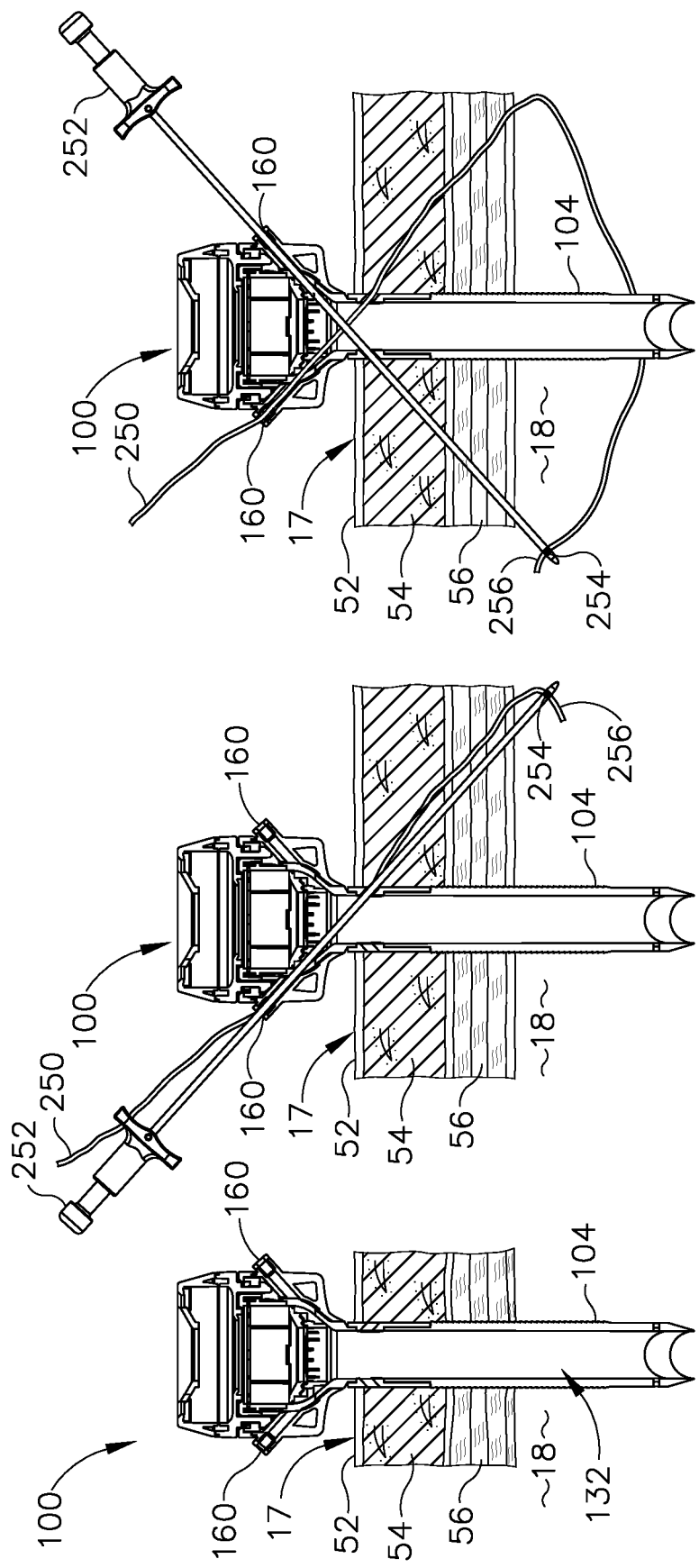
FIG. 15A depicts a schematic side sectional view of tissue of a patient and the trocar of FIG. 5A positioned through an opening formed in the tissue such that the cannula extends distally into a cavity of the patient, according to a first step of an exemplary suturing procedure.
FIG. 15B depicts a schematic side sectional view of the tissue and trocar of FIG. 15A, showing completion of an exemplary second step of the suturing procedure in which a suture thread end is directed by a suture passer device distally through the trocar and fascia layers of the tissue into the cavity along a first oblique suture path.
FIG. 15C depicts a schematic side sectional view of the tissue and trocar of FIG. 15A, showing completion of an exemplary third step of the suturing procedure in which the suture passer device is re-inserted distally through the trocar and the tissue fascia layers along a second oblique suture path to capture the free suture thread end located within the cavity.

FIG. 15A shows trocar cannula (104) extending distally through a portion of upper fat layers (54) and through a full thickness of lower fascia layers (56) of patient tissue (17), and into body cavity (18). All surgical instruments (not shown) have been withdrawn from trocar (100) such that working channel (132) is clear. FIG. 15B shows insertion of an exemplary suture passer needle (252) distally through a needle guide tube (160) and along the respective first suture path as generally described above. A distal tip (254) of suture passer needle (252) carries an end (256) of suture thread (250) along the suture path, through fascia (56) and into body cavity (18). As described above, needle guide tubes (160) and needle ports (150, 152) are positioned such that the resulting suture paths are angled obliquely relative to the central axis of trocar (100).

Once suture thread end (256) has been delivered into cavity (18), suture passer needle (252) releases suture thread end (256) and is withdrawn proximally from trocar (100). As shown in FIG. 15C, suture passer needle (252) is then re-inserted distally through the opposing needle guide tube (160) and along the respective second suture path into cavity (18). Suture passer needle (252) is then manipulated by a surgeon to recapture suture thread end (256) with needle tip (254). Once captured, thread end (256) and needle are withdrawn proximally through trocar (100) along the second suture path.

FIG. 15D shows trocar (100) and suture thread (250) following proximal removal of suture passer needle (252) along the second suture path. In the present configuration, suture thread (250) includes a first thread leg (258) passing distally along the first suture path and through a first captured portion of fascia (56) located on a first side of tissue opening (58); a second thread leg (260) passing distally along the second suture path and through a second captured portion of fascia (56) located on a second side of tissue opening; and an anchoring loop (262) extending through cavity (18) between the first and second captured portions of fascia (56). As shown in FIG. 15D, trocar (100) is withdrawn proximally from tissue opening (58) to allow thread legs (258, 260) to advance distally through needle guide tubes (160) and along their respective suture paths, thereby releasing suture thread (250) from trocar (100).

As shown in FIG. 15E, once trocar (100) has been fully disengaged from suture thread (250), thread legs (258, 260) may be pulled tight to draw together fascia (56) on either side of tissue opening (58), and then tied to form a suture knot (264) at a location just proximally of fascia layers (56). Optionally, the remaining portions of thread legs (258, 260) may be directed through fat layers (54) and skin (52) using suture needles, for example as shown in FIG. 4D using needles (62), to create an additional "superficial" suture knot to fully close tissue opening (58) and promote healing.

III. EXEMPLARY TROCAR HAVING DISTAL HOUSING WITH INTEGRALLY FORMED NEEDLE GUIDE TUBES

Figure 16A:
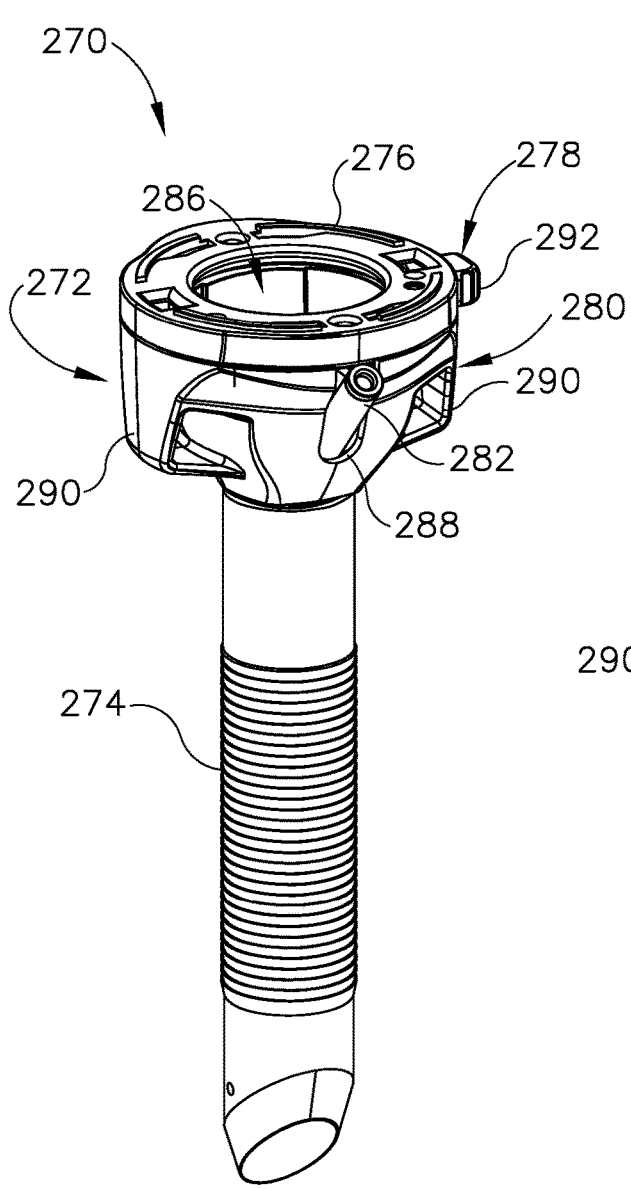
FIG. 16A depicts a perspective view of another exemplary trocar having needle guide tubes that are integrally molded with the cannula.
Figure 16B:
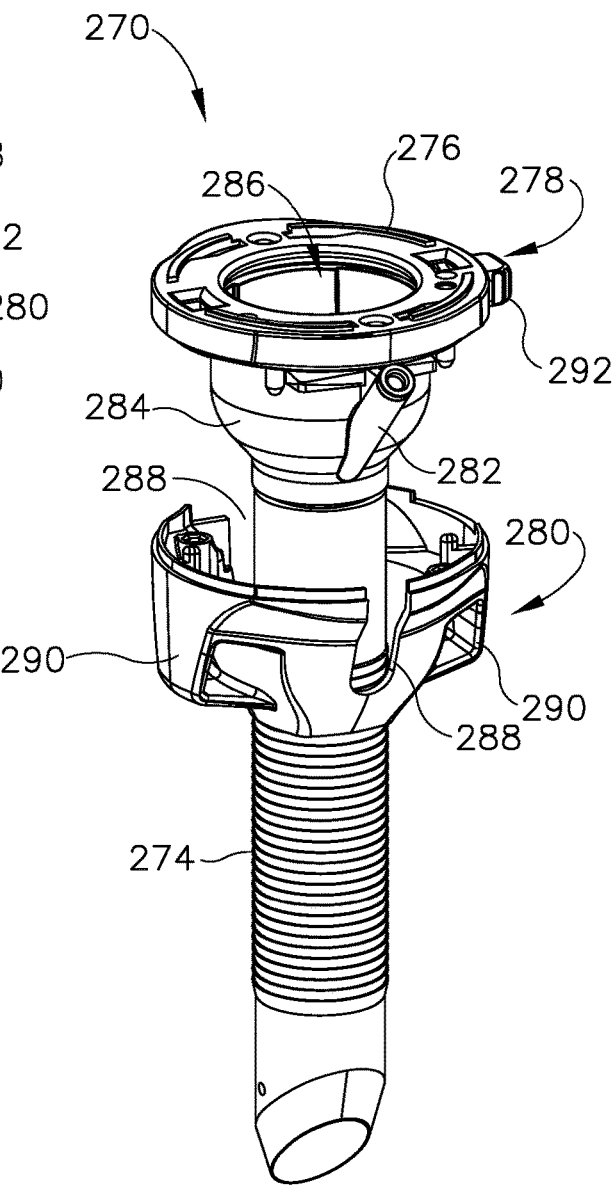
FIG. 16B depicts a partially disassembled perspective view of the trocar of FIG. 16A.

FIGS. 16A and 16B show another exemplary trocar (270). Trocar (270) is similar to trocar (100) in that trocar (270) includes a housing (272) and a cannula (274) coupled to and extending distally from housing (272) along a central axis of trocar (270). Housing (272) includes a proximal housing (not shown), a housing cap plate (276), a latch ring (278), and a distal housing (280). These components are substantially similar in structure and function to the corresponding components of trocar (100) described above, except as otherwise described below. In particular, trocar (270) includes first and second needle guide tubes (282) that are formed integrally with proximal hub (284) of cannula (274), rather than with distal housing (280). Distal ends of needle guide tubes (282) open directly to a working channel (286) of trocar (270), and thus needle guide tubes (282) define the needle entrance ports to working channel (286). Plug seals (154) received within needle entrance ports (150) of trocar (100) may be omitted from trocar (270).

Distal housing (280) of trocar (270) includes a pair of axially extending slots (288) sized and shaped to accommodate needle guide tubes (282) therethrough when distal housing (280) is connected to housing cap plate (276) during device assembly. In the present example, distal housing (280) is oriented such that slots (288) are arranged in sidewalls of distal housing (280) extending between side wings (290) of distal housing (280). In alternative configurations, slots (288) may be arranged in side wings (290) or in various other portions of distal housing (280). Similar to trocar (100) described above, trocar (270) is configured such that a knob (292) of latch ring (278) remains circumferentially spaced from each of needle guide tubes (282) throughout a full range of permissible rotation of latch ring (278) relative to housing cap plate (276). As described above in connection with trocar (100), such a configuration ensures unobstructed access to needle guide tubes (282) during use.

IV. EXEMPLARY TROCAR HAVING SUTURING FEATURES FOR USE WITH VARIOUS TISSUE THICKNESSES

Figure 17:
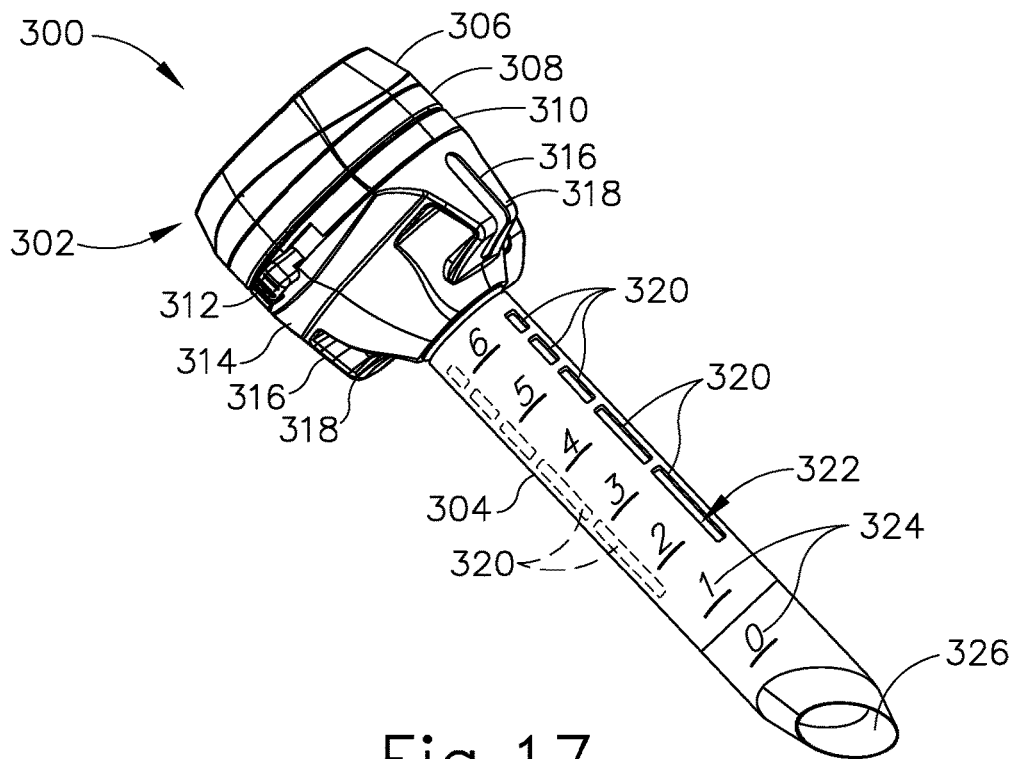
FIG. 17 depicts a perspective view of another exemplary trocar including a housing and a cannula having a plurality of axially spaced needle ports and corresponding indicia.

FIG. 17 shows another exemplary trocar (300) configured for use with patient tissue of various thicknesses. Trocar (300) is similar to trocar (100) in that trocar (300) includes a housing (302) and a cannula (304) coupled to and extending distally from housing (302) along a central axis of trocar (300). Housing (302) includes a proximal housing having a proximal housing head (306) and a proximal housing base (308), a housing cap plate (310), a latch ring (312), and a distal housing (314). These components are substantially similar in structure and function to the corresponding components of trocar (100) described above, except as otherwise described below. In particular, distal housing (314) includes needle guide structures in the form of slots (316) formed in side wings (318). Additionally, cannula (304) includes a plurality of elongate needle ports (320) spaced axially along opposing sides of cannula (304). Each needle port (320) is provided with a pierceable seal (322), which may include an axial slit (not shown) to ease passage of a suture passer needle through seal (322).

Cannula (304) of trocar (300) further includes visual indicia shown in the form of tissue depth graduation marks (324) spaced axially along a length of cannula (304). Marks (324) may indicate any suitable distance increments, such as inches or centimeters for example, and subdivisions of each increment. Marks (324) are configured to communicate to a surgeon a depth, measured from cannula tip (326), to which cannula (304) has been inserted within patient tissue. For example, during or after insertion of cannula (304) into tissue, a surgeon may observe a distal-most mark (324) that is visible extracorporeally to determine a depth to which cannula (304) has been inserted into the tissue, which may indicate a thickness of the tissue. Those of ordinary skill in the art will appreciate that any one or more of the features of trocar (300) may be incorporated into any of the other exemplary trocars described herein.

Figure 18A:
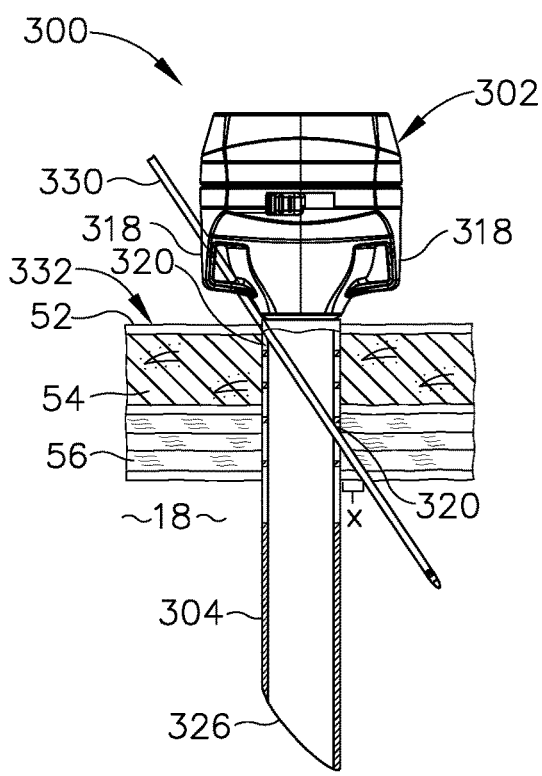
FIG. 18A depicts a schematic side sectional view of the trocar of FIG. 17 positioned within tissue of a first thickness, showing a suture passer device extending distally through the trocar and tissue along a first exemplary suture path defining a first oblique angle relative to a central axis of the trocar.
Figure 18B:
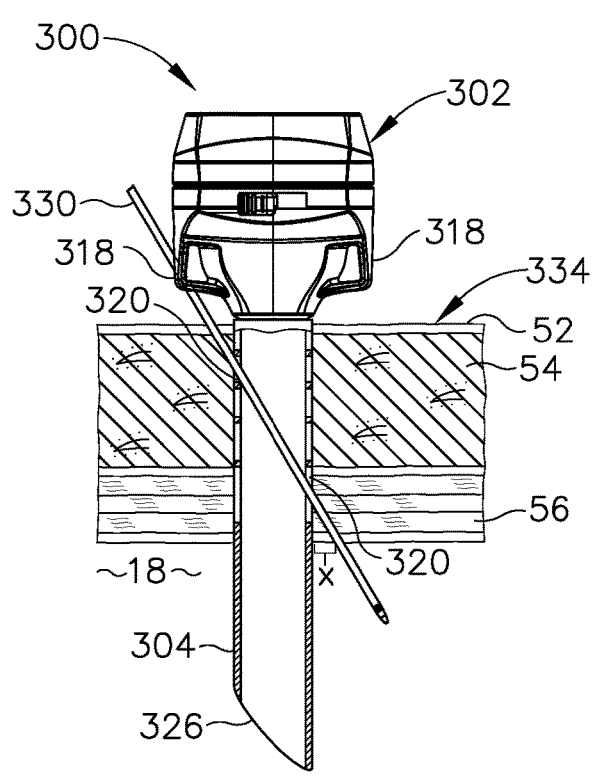
FIG. 18B depicts a schematic side sectional view of the trocar of FIG. 17 positioned within tissue of a second thickness, showing the suture passer device extending distally through the trocar and tissue along a second exemplary suture path defining a second oblique angle relative to the central axis of the trocar.

As shown in FIGS. 17-18B, elongate needle ports (320) increase in length along cannula (304) to allow a suture passer needle (330) to be directed through trocar (300) at a selected suture path angle, measured relative to a central axis of trocar (300), of a plurality of available suture path angles. This enables trocar (300) to be used as a suturing guide mechanism with tissues exhibiting a range of tissue thicknesses, while maintaining a consistent tissue bite distance (X) across the range of tissue thickness. FIG. 18A shows trocar (300) inserted through tissue (332) of a first thickness. Suture needle passer (330) is inserted through a first pair of needle ports (320) to define a first suture path angle and a tissue bite distance (X). FIG. 18B shows trocar (300) inserted through tissue (334) of a greater thickness than tissue (332). Suture needle passer (330) is inserted through a second pair of needle ports (320) to define a second suture path angle while maintaining substantially the same tissue bite distance (X) shown in FIG. 18A.

V. EXEMPLARY TROCAR FOR APPLYING MULTIPLE SUTURES AT SAME SURGICAL SITE

In some instances, it may be desirable to apply multiple suture threads for closing an opening formed in patient tissue by a trocar cannula. For example, in instances in which the tissue opening is formed by a trocar cannula having a diameter of approximately 15 mm or greater, application of multiple suture threads may ensure effective closing of the tissue opening to promote complete and proper healing of the tissue. Accordingly, it may be desirable to provide one or more variations of any of the above-described trocars that includes suture features of suitable quantity and arrangement to facilitate application of multiple suture threads for closing a tissue opening.

FIGS. 19-21 show an exemplary variation of trocar (100) in the form of trocar (340), having suture features configured to facilitate application of first and second suture threads for closing a single tissue opening formed by trocar (340). Trocar (340) is similar to trocar (100) in that trocar (340) includes a housing (342) and a cannula (344) coupled to and extending distally from housing (342) along a central axis of trocar (340). Housing (342) includes a proximal housing (not shown) similar to proximal housing (106), a housing cap plate (348), a latch ring (350) having a user engagement feature (352), and a distal housing (354). Cannula (344) and housing together define a working channel (356) extending through trocar (340) along the central axis thereof. These components of trocar (340) are substantially similar in structure and function to the corresponding components of trocar (100) described above, except as otherwise described below. For example, like trocar (100), trocar (340) includes a distal seal assembly (358), shown in FIG. 19, that separates a lumen of cannula (344) from an interior of housing (342). However, unlike distal seal assembly (140) of trocar (100), distal seal assembly (358) is shown in the form of a duckbill seal. Further, trocar (340) includes a proximal seal assembly (360) in the form of an instrument seal supported within proximal housing (346), as shown in FIG. 20.

Distal housing (354) of trocar (340) includes four needle guide tubes (362) defining respective needle entrance ports, and four needle exit ports (364) arranged on cannula (344), each needle exit port (364) corresponding to a respective needle guide tube (362). Each needle guide tube (362) and its respective needle exit port (364) defines a suture path, indicated by axes (A1, A2, A3, A4) in FIG. 21, extending distally through and obliquely relative to the central axis of trocar (340). Each needle port (362, 364) opens to working channel (356) and is sealed by a respective pierceable seal. Specifically, an entrance end of each needle guide tube (362) is sealed by a respective pierceable seal cap (366), which may be similar to seal caps (164, 230) described above. Each needle exit port (364) is sealed by a respective pierceable seal protrusion (368) projecting radially inwardly from an inner surface of a cannula sleeve (370), which may be similar to cannula sleeve (158) described above.

In the present example, latch ring (350) is oriented rotationally about the central axis of trocar (340) such that its user engagement feature (352) is generally diametrically opposed from an insufflation port (372). Additionally, needle guide tubes (362) and their respective needle exit ports (364) are arranged circumferentially about the central axis such that each needle guide tube (362) is circumferentially spaced from user engagement feature (352) and from insufflation port (372). As shown best in FIG. 20, user engagement feature (352) is spaced circumferentially equidistantly between a first pair of needle guide tubes (362), and insufflation port (372) is spaced circumferentially equidistantly between a second pair of needle guide tubes (362). Each needle exit port (364) is positioned to align with a respective needle guide tube (362) arranged along the corresponding suture path. In alternative examples, various other quantities and arrangements of needle guide tubes (362) and their respective needle exit ports (364) may be provided.

In use, each needle guide tube (362) and its respective needle exit port (364) cooperate with an opposed needle guide tube (362) and its needle exit port (364) to guide application of a suture thread (not shown) to tissue. Application of each of the first and second suture threads may be performed using the exemplary procedure described above in connection with FIGS. 15A-15D, for example. As is evident in FIG. 20, needle guide tubes (362) and needle exit ports (364) are circumferentially arranged such that the applied first and second suture threads cross over one another to define an X-shaped pattern in the tissue when viewed from above. It will be appreciated that any suitable circumferential spacing between needle guide tubes (362), and between needle exit ports (364), may be provided to achieve a desired suture pattern and resulting closure effect on the tissue opening.

VI. EXEMPLARY TROCAR WITH SUTURE PASSER GUIDE TUBE

A. Overview of Exemplary Trocar with Suture Passer Guide Tube

Figure 22:
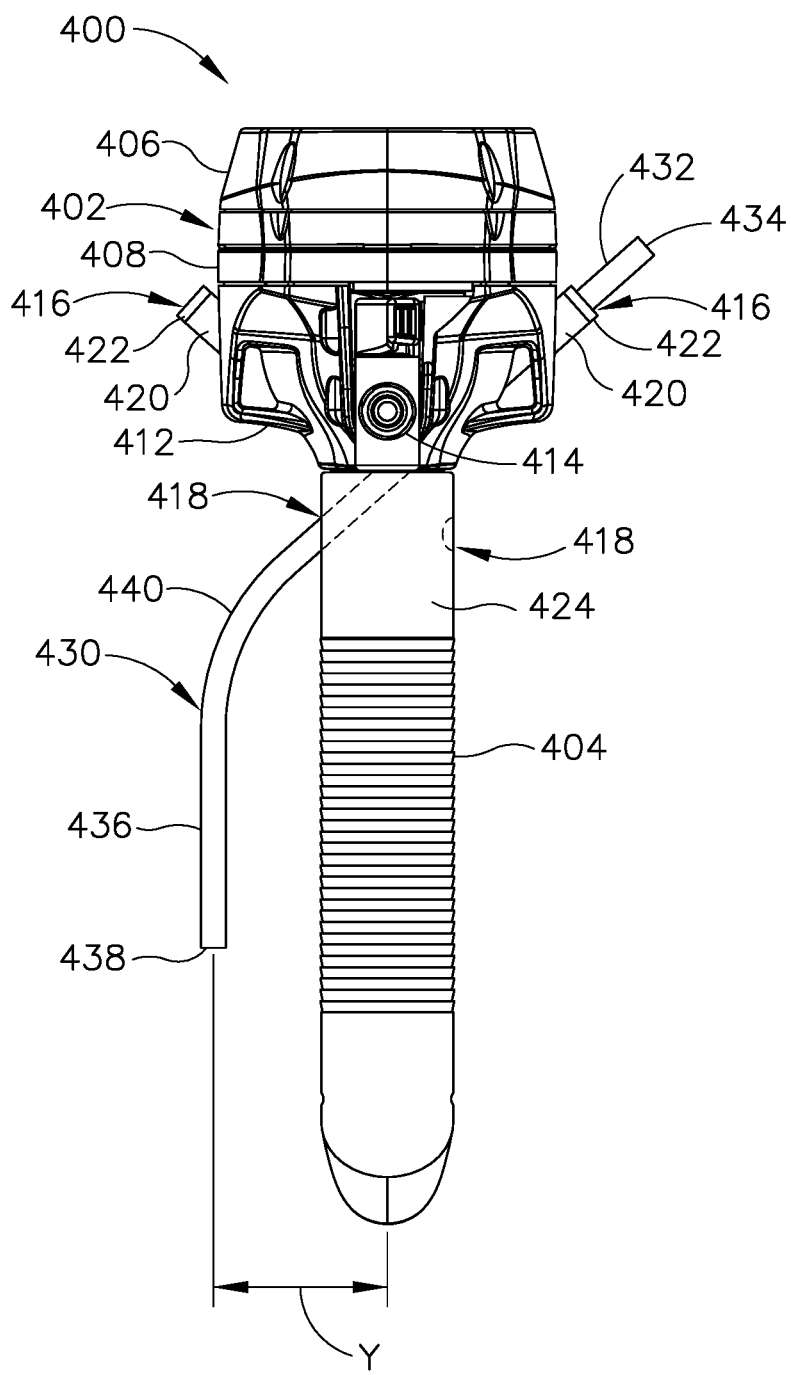
FIG. 22 depicts a side elevational view of another exemplary trocar and a suture passer guide tube.

FIG. 22 shows another exemplary surgical access device in the form of trocar (400) and a corresponding suture passer guide tube (430). As described in greater detail below, the use of suture passer guide tube (430) with trocar (400) ensures a consistent tissue bite distance (X) across a range of tissue thicknesses. In particular, for various tissue thicknesses, suture passer guide tube (430) guides a suture passer needle distally through the tissue and into the body cavity while maintaining a consistent radial distance between the central axis of trocar (400) and the location at which the suture passer needle passes distally through an inner-most layer of the tissue, as shown in FIGS. 23C-23D.

In the present example, trocar (400) is similar in structure to trocar (100). In particular, trocar (400) includes a housing (402) and a cannula (404) coupled to and extending distally from housing (402) along a central axis of trocar (400). Housing (402) includes a proximal housing (406), a housing cap plate (408), a latch ring (not shown) similar to latch ring (110), and a distal housing (412). Trocar (400) further includes a working channel (not shown) similar to working channel (132), and an insufflation port (414) configured to direct insufflation fluid into the working channel. Trocar (400) further includes a set of first and second needle entrance ports (416) and a corresponding set of first and second needle exit ports (418). Each needle entrance port (416) is opposed from its corresponding needle exit port (418), and the paired needle entrance and exit ports (416, 418) define a respective suture path extending through trocar (400) and across the working channel at an oblique angle relative to the trocar central axis. In the present example, needle entrance ports (416) are diametrically opposed from one another and needle exit ports (418) are also diametrically opposed from one another such that the resulting first and second suture paths extend in a common vertical plane passing through the trocar central axis.

Each needle entrance port (416) of trocar (400) is defined by a respective needle entry guide tube (420) projecting angularly outwardly from a respective side portion of distal housing (412). Needle entry guide tubes (420) are fitted with seal caps (422) that function to seal needle entrance ports (416). Each needle exit port (418) is formed in a proximal portion of cannula (404). A cannula sleeve (424) encircles the proximal portion of cannula (404) and functions to seal needle exit ports (418). In the present example, the above-described components of trocar (400) are substantially similar in structure and function to the corresponding components of trocar (100), described above. In other examples, trocar (400) may be suitably modified to incorporate any one or more features of the other trocars (10, 100, 270, 300, 340) described herein.

Figure 23A:
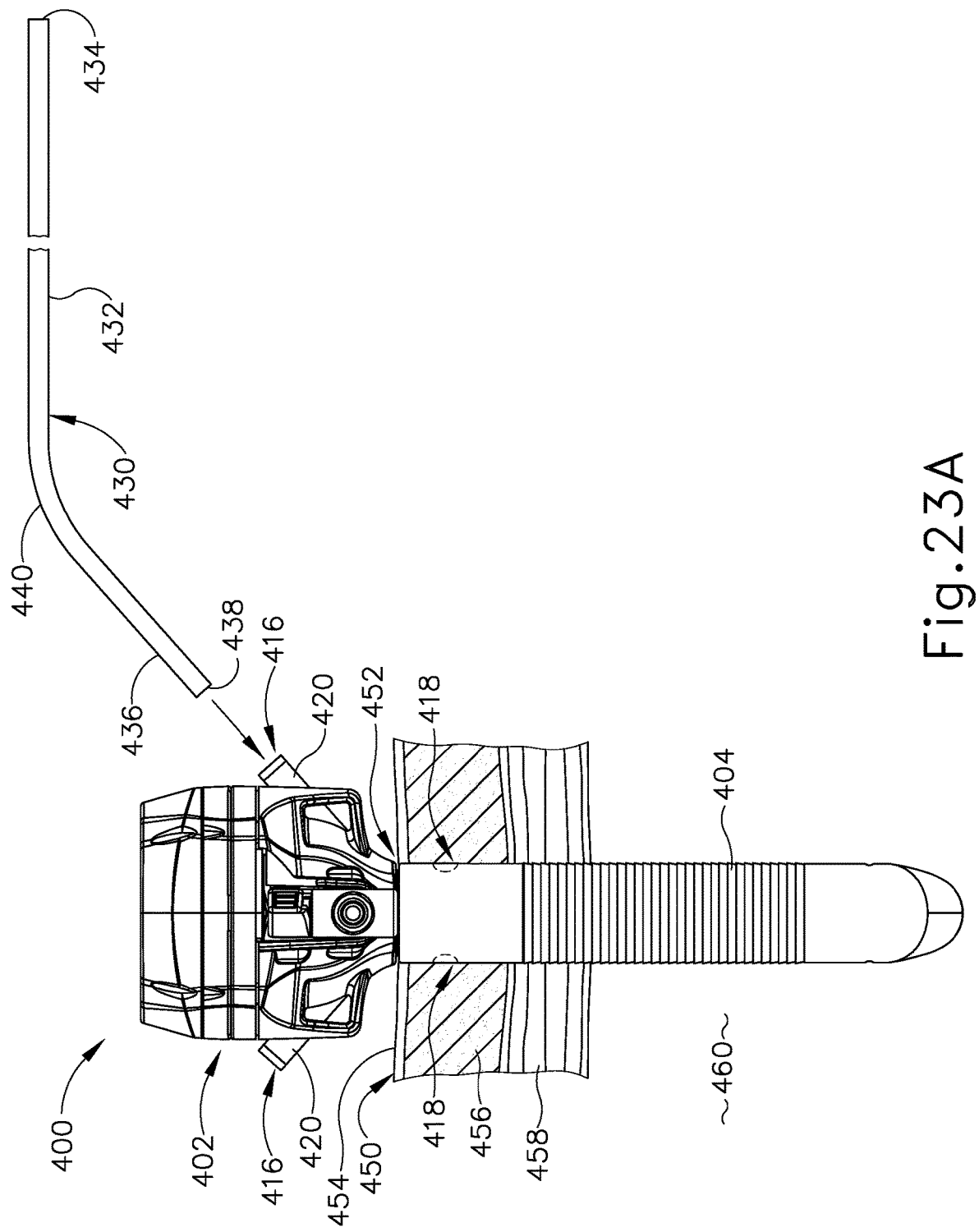
FIG. 23A depicts a schematic side sectional view of the trocar of FIG. 22 positioned within tissue, showing the suture passer guide tube being inserted distally through the trocar.

As shown in FIGS. 22 and 23A, trocar (400) is employed in combination with a suture passer guide tube (430). Suture passer guide tube (430) is configured to be received through each pair of needle entrance and exit ports (416, 418), and is configured to guide a suture passer device (470) (see FIG. 23B) along the respective suture path and corresponding tissue, as described below. Suture passer guide tube (430) includes a proximal tube portion (432) defining a proximal tube end (434), and a distal tube portion (436) defining a distal tube end (438). Distal tube portion (436) is angled relative to proximal tube portion (432) such that when suture passer guide tube (430) is assembled with trocar (400), distal tube portion (436) extends angularly toward the trocar central axis and positions distal tube end (438) a predetermined radial distance (Y) (or "apposition distance") from the trocar central axis, as shown in FIG. 22.

In the present example, proximal and distal tube portions (432, 436) are each generally straight and are separated by a curved medial tube portion (440) that provides a smooth angular transition between proximal and distal tube portions (432, 436). Additionally, distal tube portion (436) is angled relative to proximal tube portion (432), via curved medial tube portion (440), such that distal tube portion (436) extends along an axis that is parallel to the trocar central axis. In other examples, distal tube portion (436) may be curved, and/or distal tube portion (436) may extend distally along an axis that is angled relative to the trocar central axis.

As shown in FIG. 22, proximal tube portion (432) of suture passer guide tube (430) is formed with a length sufficient to extend distally from a position proximal of needle entrance port (416) to a position distal of needle exit port (418), such that curved medial tube portion (440) is positioned externally of cannula (404). In various examples, distal tube portion (436) is formed with any suitable length up to a distal end of cannula (404). For instance, in the illustrated example in which distal tube portion (436) extends parallel to the trocar central axis, distal tube portion (436) may extend distally with any length sufficient to establish an axis parallel to the central trocar axis. This configuration enables suture passer guide tube (430) to achieve a consistent tissue bite distance (X) across all thicknesses of patient tissue in which trocar (400) is positioned, including tissue thicknesses that are greater than a distal length of suture passer guide tube (430).

In other examples in which distal tube portion (436) extends angularly relative to the trocar central axis, distal tube portion (436) may be formed with a length sufficient to pass distally through a predetermined maximum tissue thickness. Additionally, in such examples, distal tube portion (436) may be suitably angled relative to proximal tube portion (432) so as to establish the predetermined apposition distance (Y) at distal tube end (438). This alternative configuration enables suture passer guide tube (430) to maintain a consistent tissue bite distance (X) across a predetermined range of tissue thicknesses.

Figure 23B:
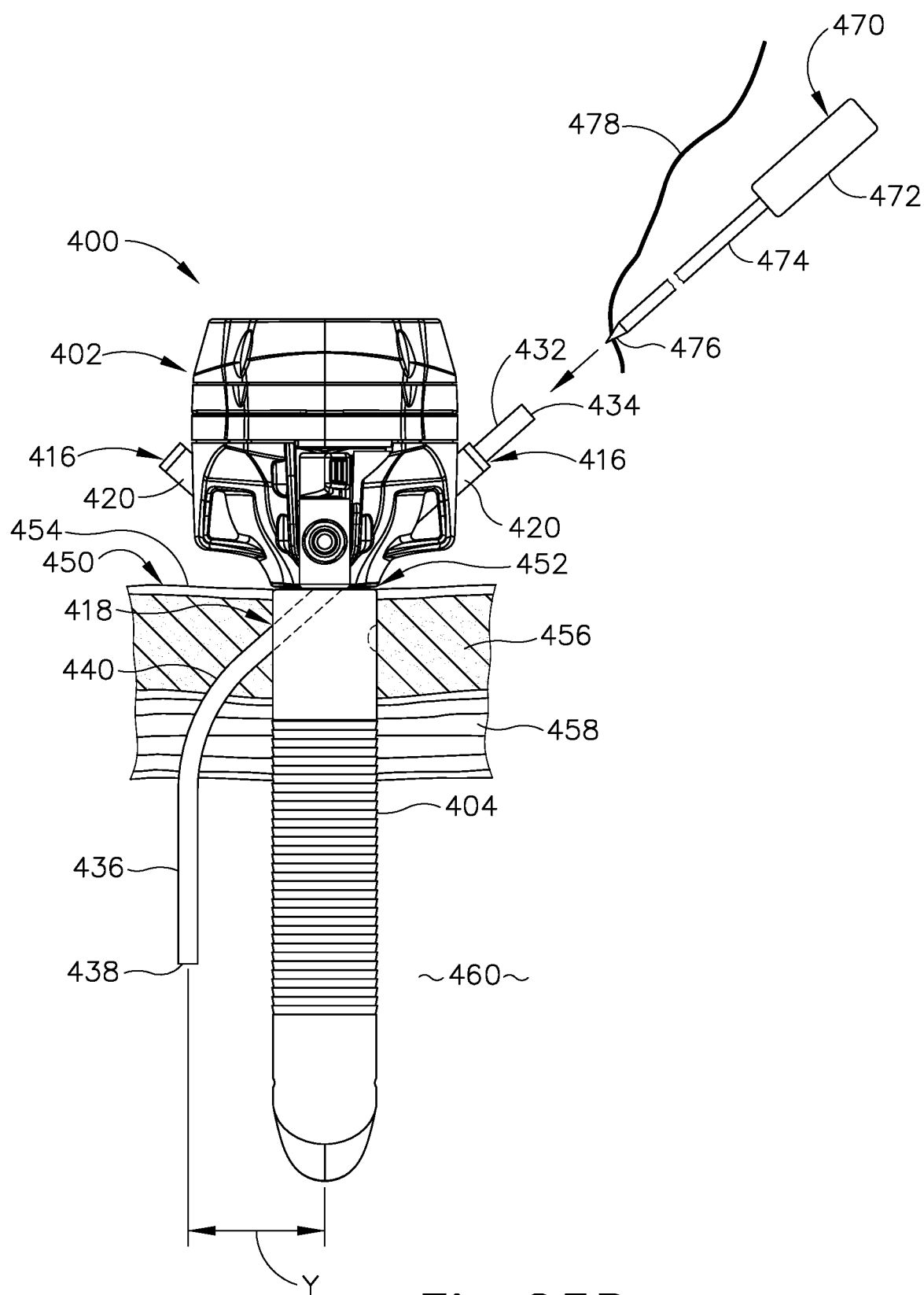
FIG. 23B depicts a schematic side sectional view of the trocar and suture passer guide tube of FIG. 23A, showing a suture passer needle being inserted distally through the suture passer guide tube.

Suture passer guide tube (430) may be formed of a variety of suitable materials that will be readily apparent to those of ordinary skill in the art. For instance, suture passer guide tube (430) may be formed of a resilient material that enables guide tube (430) to resiliently flex when passing distally through trocar (400), as shown in FIG. 23A, and then reassume its original shape once fully seated within trocar (400), as shown in FIG. 23B.

B. Exemplary Method of Using Trocar and Suture Passer Guide Tube

FIGS. 23A-23D show an exemplary method of using trocar (400) and suture passer guide tube (430) for suturing closed an opening (452) formed in patient tissue (450) by trocar (400). Tissue (450) is similar to tissue (17) described above in that tissue (450) comprises superficial outer layers including a layer of skin (454) and multiple layers of fat (456), and deeper layers of fascia (458), which are fibrous and flexible with relatively higher tensile strength than the superficial layers (454, 456). Opening (452) in tissue (450) provides access to a body cavity (460) for performance of an endoscopic surgical procedure on tissue accessible via cavity (460).

FIG. 23A shows trocar cannula (404) extending distally through tissue opening (452) and into body cavity (460). Following the completion of one or more surgical procedures using trocar (400) and an endoscopic surgical instrument (not shown), the instrument is withdrawn proximally from the working channel of trocar (400). Distal tube end (438) of suture passer guide tube (430) is aligned with one of the needle entry guide tubes (420) of trocar (400), and suture passer guide tube (430) is directed distally through trocar (400) along the respective suture path. Suture passer guide tube (430) is advanced distally so that distal tube end (438) extends distally through needle exit port (418), and distal tube portion (436) and curved medial tube portion (440) enter into tissue (450), as shown in FIG. 23B. As described above, suture passer guide tube (430) may be formed of a material having a suitable degree of resilience. Accordingly, curved medial tube portion (440) may resiliently straighten as it passes through trocar (400), and then reassume its curved shape upon exiting needle exit port (418) so as to angle distal tube portion (436) downwardly through fascia (458) and toward body cavity (460).

As shown in FIG. 23B, when suture passer guide tube (430) reaches its final, seated position relative to trocar (400), proximal tube portion (432) extends through trocar (400), and curved medial tube portion (440) and distal tube portion (436) extend through tissue (450) such that distal tube end (438) is positioned at a predetermined apposition distance (Y) from the trocar central axis. In the present example, distal tube portion (436) is long enough that distal tube end (438) passes fully through the inner-most fascia layer (458) and into body cavity (460).

Following placement of suture passer guide tube (430) within trocar (400), a suture passer device (470) is used to direct a suture thread (478) distally through trocar (400) and suture passer guide tube (430). As shown in FIG. 23B, suture passer device (470) includes a handle (472) and an elongate flexible needle (474) extending distally from handle (472) and having a tip (476) configured to capture an end of suture thread (478). In various examples, suture passer guide tube (430) is stiffer than flexible needle (474), such that suture passer guide tube (430) does not deform when needle (474) is directed through guide tube (430).

As shown in FIGS. 23B and 23C, flexible needle (474) is directed distally through suture passer guide tube (430) to deposit the captured end of suture thread (478) within body cavity (460). Flexible needle (474) resiliently flexes as it passes from proximal tube portion (432) to angled distal tube portion (436). Following deposition of the end of suture thread (478) within cavity (460), needle (474) is withdrawn proximally from suture passer guide tube (430). Though not shown, flexible needle (474) is then directed distally through the opposing needle entry guide tube (420) along the second suture path of trocar (400), in manner similar to that shown in FIGS. 23B and 23C. Trocar (400) is manipulated as necessarily to recapture the deposited end of suture thread (478) with needle tip (476), and needle (474) is withdrawn proximally along the second suture path with the recaptured thread end.

Following the removal of suture passer device (470) from trocar (400), trocar (400) is withdrawn proximally from tissue opening (452). This motion allows suture thread (478) to release from trocar (400) in a manner similar to that shown and described above in connection with FIG. 15D. Freed ends of suture thread (478) may then be tied to close tissue opening (452) in a manner similar to that shown and described above in connection with FIG. 15E.

FIG. 23D shows trocar (400), suture passer guide tube (430), and suture passer device (470) positioned within tissue (480) of a thickness greater than tissue (450). Tissue (480) includes an opening (482) and layers (482, 486, 488) similar to those of tissue (450). Advantageously, the configuration of suture passer guide tube (430) enables maintenance of a consistent tissue bite distance (X) despite the increased thickness of tissue (480) relative to tissue (450). In the example of FIG. 23D, distal tube portion (436) remains long enough to extend fully through an inner-most layer of tissue (480) into cavity (460). It will be understood, however, that in configurations in which distal tube portion (436) extends parallel to the trocar central axis, distal tube portion (436) will remain effective to ensure maintenance of the same tissue bite distance (X) in tissues of even greater thicknesses having inner-most fascia layers (488) situated distally of distal tube end (438).

VII. EXEMPLARY TROCAR HAVING FLEXIBLE NECK JOINT

FIGS. 24-27 show another exemplary trocar (500) having a movable neck joint (530) configured to enable a physician to achieve a consistent tissue bite distance (X) with trocar (500) across a range of tissue thicknesses, as described in greater detail below. Trocar (500) of the present example is similar to the trocars of the previously described examples in that trocar (500) includes a housing (502) and a cannula (504) coupled to and extending distally from housing (502). Housing (502) includes a removable proximal housing (not shown) similar to proximal housing (106), a housing cap plate (508), a latch ring (not shown) similar to latch ring (110), and a distal housing (512). Trocar (500) further includes a working channel (not shown) similar to working channel (132), and an insufflation port (514) configured to direct insufflation fluid into the working channel.

Trocar (500) further includes a set of first and second needle entrance ports (516) arranged on opposed side portions of distal housing (512), and a corresponding set of first and second needle exit ports (518) arranged on opposed side portions of cannula (504). Each needle entrance port (516) is opposed from its corresponding needle exit port (518). Each entrance port (516) and its corresponding exit port (518) define a respective suture path extending through trocar (500) and across the working channel at an oblique angle relative to the central axis of cannula (504). In the present example, needle entrance ports (516) are diametrically opposed from one another and needle exit ports (518) are also diametrically opposed from one another such that the resulting first and second suture paths extend and intersect in a common vertical plane passing through the trocar central axis. In will be understood that various alternative quantities and configurations of needle ports (516, 518) may be provided in other examples.

Each needle entrance port (516) of trocar (500) is defined by an opening to a respective needle guide tube (520) formed integrally with a respective side of distal housing (512). Each needle exit port (518) is formed on a respective side of a proximal portion of cannula (504), and has an elongate, axially extending shape that enables a suture passer device to be directed through needle exit port (518) at various suture path angles relative to the central axis of cannula (504), as described below. Needle entrance ports (516) and/or needle exit ports (518) may be provided with respective seals configured to be pierced by a suture passer device during a wound closure procedure. In various examples, trocar (500) may incorporate any one or more features of the other trocars (10, 100, 270, 300, 340, 400) described herein.

Figure 24:
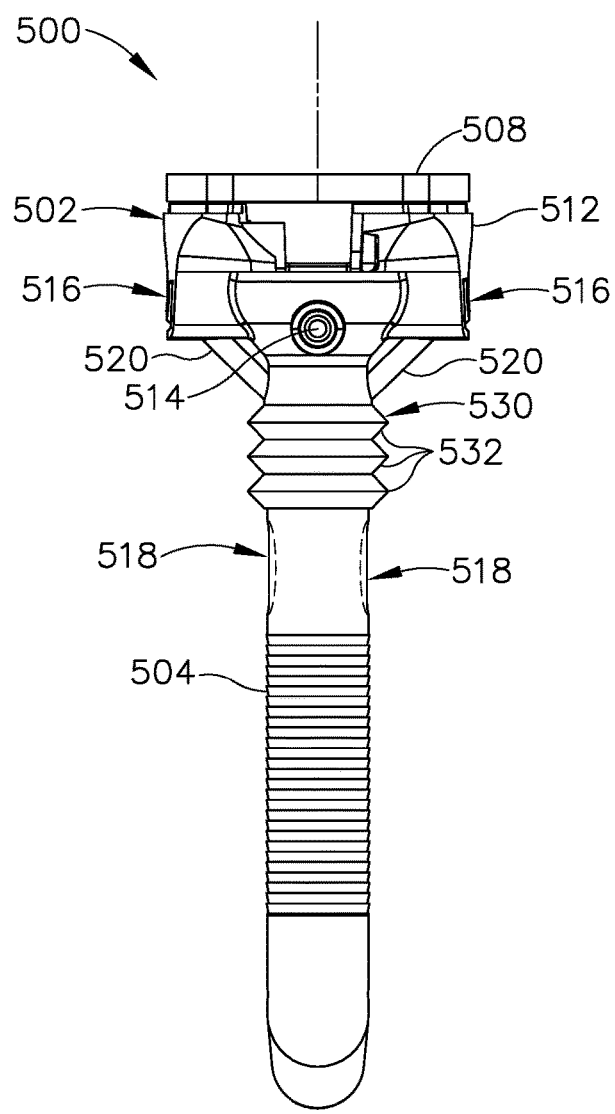
FIG. 24 depicts a front elevational view of an exemplary trocar having a movable neck joint, showing the trocar in a straight configuration.
Figure 25:
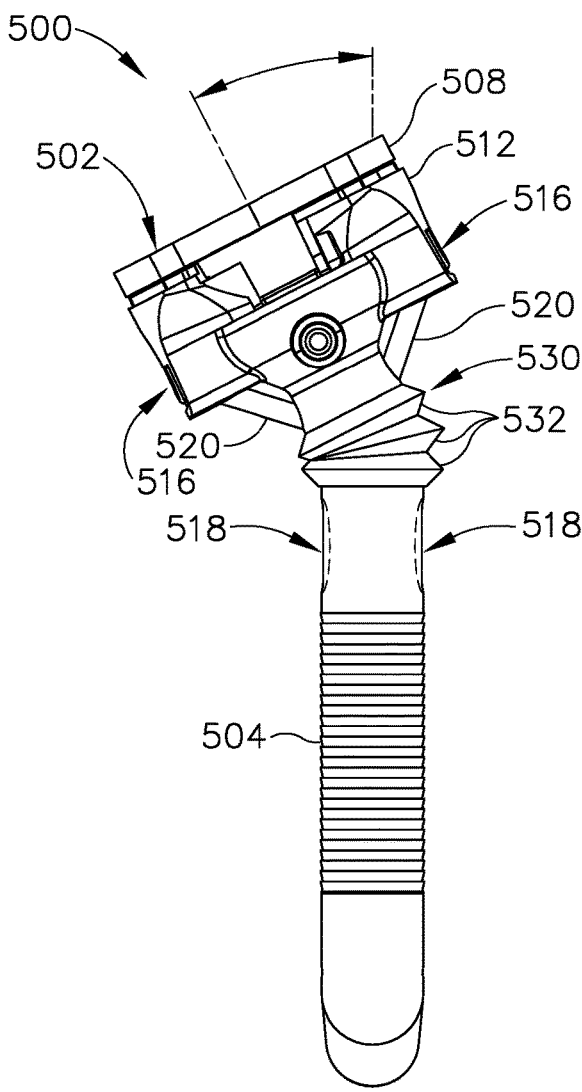
FIG. 25 depicts a front elevational view of the trocar of FIG. 24, showing the trocar in an exemplary angled configuration.

Movable neck joint (530) of trocar (500) couples a distal end of distal housing (512) to a proximal end of cannula (504), and is shown in the form of a flexible sleeve joint having a plurality of annular bellows (532). As shown in FIGS. 24 and 25, flexible sleeve joint (530) enables housing (502) to deflect angularly (or "articulate") relative to cannula (504) about a full circumference of trocar (500). More specifically, flexible sleeve joint (530) enables housing (502) to deflect relative to cannula (504) from a straight configuration (FIG. 24) in which a central axis of housing (502) aligns coaxially with a central axis of cannula (504), to a variety of angled configurations (e.g., FIG. 25) in which the central axis of housing (502) is angled relative to the central axis of cannula (504). Though not shown, trocar (500) may include one or more locking mechanisms that may be activated by a physician to temporarily secure trocar (500) in a particular angled configuration.

Flexible sleeve joint (530) of the present example is formed of a flexible elastomeric material, such as a rubber for example, that resiliently biases trocar (500) toward the straight configuration shown in FIG. 24. In that regard, bellows (532) of flexible sleeve joint (530) are resiliently compressible and extendable to facilitate angular deflection of housing (502) relative to cannula (504). While flexible sleeve joint (530) of the present example is shown having three bellows (532), it will be appreciated that any suitable quantity of bellows (532) may be provided. Additionally, though not shown, it will be appreciated that flexible sleeve joint (530) has a hollow interior that enables the interior of housing (502) to communicate with a lumen of cannula (504) such that the working channel of trocar (500) extends axially through flexible sleeve joint (530).

Figure 26:
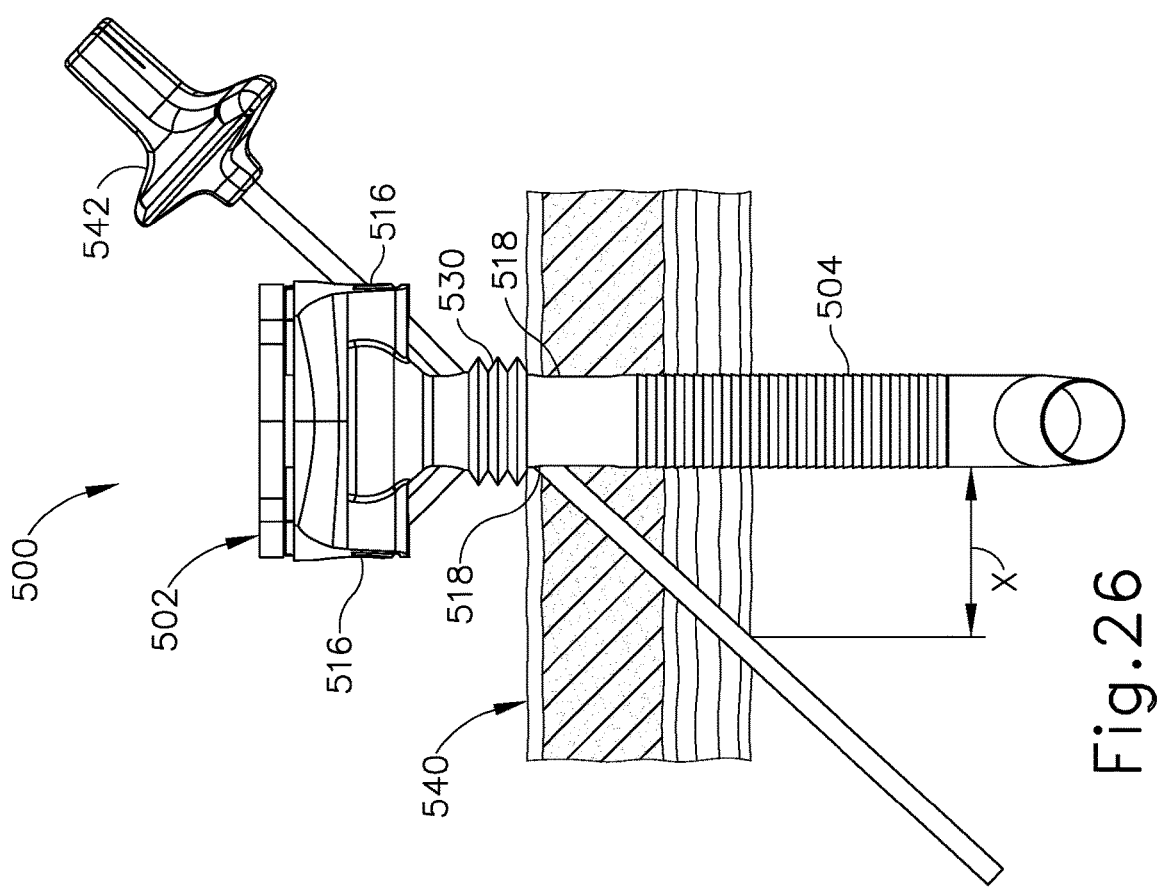
FIG. 26 depicts a rear elevational view of the trocar of FIG. 24, showing the trocar positioned in tissue of a first exemplary thickness and oriented in a straight configuration that defines a tissue bite distance.

FIG. 26 shows trocar (500) positioned within an opening formed in tissue (540) of an exemplary first thickness. Tissue (450) includes layers of skin, fat, and fascia similar to tissue (17) described above. A suture passer device (542) is shown directed distally through trocar (500) along a suture path defined by a needle entrance port (516) and a corresponding opposed needle exit port (518). Trocar (500) is provided in a straight configuration such that suture passer device (542) extends distally through trocar (500) and tissue (540) at a first suture path angle relative to the central axis of cannula (504), to thereby define a tissue bite distance (X).

Figure 27:
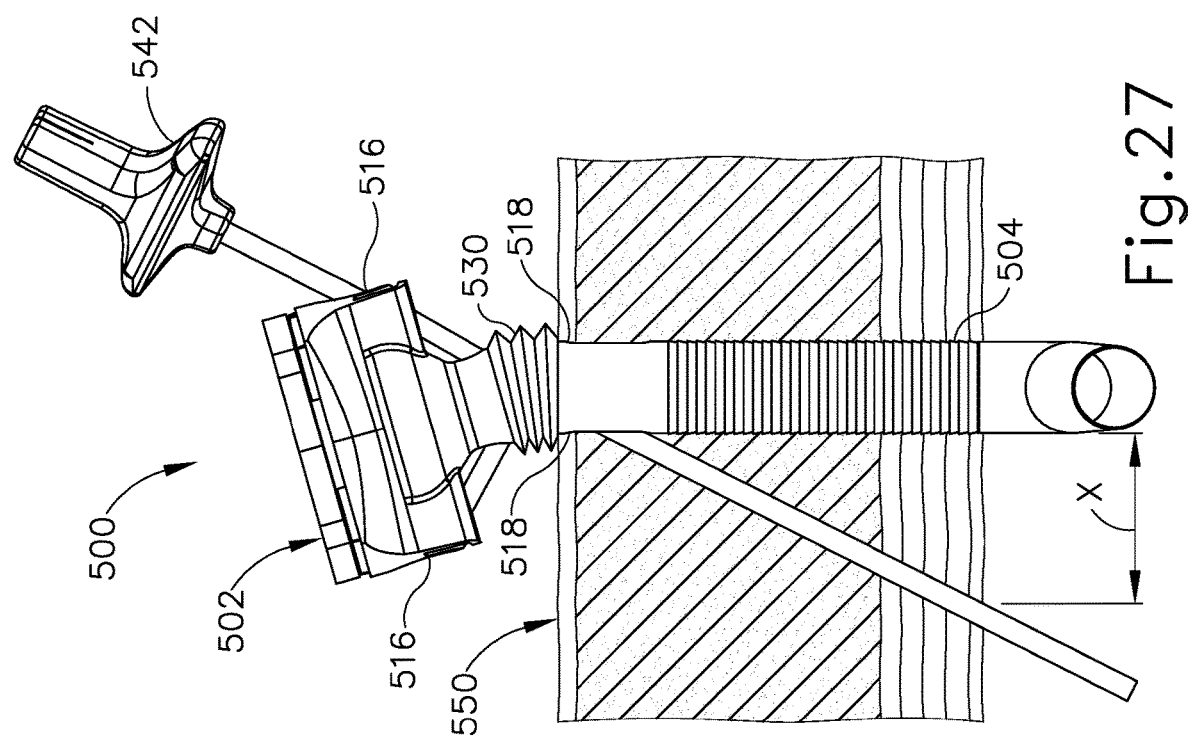
FIG. 27 depicts a rear elevational view of the trocar of FIG. 26, showing the trocar positioned in tissue of a second exemplary thickness and oriented in an exemplary angled configuration to define the same tissue bite distance of FIG. 26.

FIG. 27 shows trocar (500) positioned within an opening formed in tissue (550) of an exemplary second thickness that is greater than the first thickness of tissue (540) of FIG. 26. Tissue (550) is otherwise similar to tissue (540) in that tissue (550) includes layers of skin, fat, and fascia. As shown, trocar (500) is provided in an angled configuration in which housing (502) is deflected relative to cannula (504). Consequently, suture passer device (542) is directed distally through trocar (500) and tissue (550) at a second, smaller suture path angle to achieve the same tissue bite distance (X) as achieved in thinner tissue (540) of FIG. 26. Accordingly, flexible sleeve joint (530) of trocar (500) enables a consistent tissue bite distance (X) to be achieved across a range of different tissue thicknesses.

VIII. EXEMPLARY TROCAR HAVING BALL-AND-SOCKET NECK JOINT

FIGS. 28-31 show another exemplary trocar (600) having a movable neck joint (630) configured to enable a physician to achieve a consistent tissue bite distance (X) with trocar (600) across a range of tissue thicknesses. Trocar (600) is similar to trocar (500) in that trocar (600) includes a housing (602) and a cannula (604) coupled to and extending distally from housing (602). Housing (602) includes a removable proximal housing (not shown) similar to proximal housing (106), a housing cap plate (608), a latch ring (not shown) similar to latch ring (110), and a distal housing (612). Trocar (600) further includes a working channel (not shown) similar to working channel (132), and an insufflation port (614) configured to direct insufflation fluid into the working channel.

Trocar (600) further includes a set of first and second needle entrance ports (616) arranged on opposed sides of distal housing (612), and a corresponding set of first and second needle exit ports (618) arranged on opposed sides of a proximal portion of cannula (604). Needle ports (616, 618) are similar to needle ports (516, 518) described above. In particular, each entrance port (616) and its corresponding exit port (618) define a respective suture path extending through trocar (600) and across the working channel at an oblique angle relative to the central axis of cannula (604). In various examples, trocar (600) may incorporate any one or more features of the other trocars (10, 100, 270, 300, 340, 400) described herein.

Movable neck joint (630) of trocar (600) is shown in the form of a ball-and-socket joint. Like flexible sleeve joint (530) described above, ball-and-socket joint (630) enables housing (602) to deflect angularly (or "articulate") relative to cannula (604). More specifically, ball-and-socket joint (630) enables housing (602) to deflect relative to cannula (604) from a straight configuration (FIG. 28) in which a central axis of housing (602) aligns coaxially with a central axis of cannula (604), to a variety of angled configurations (e.g., FIG. 29) in which the central axis of housing (602) is angled relative to the central axis of cannula (604). Optionally, ball-and-socket joint (630) may enable housing (602) to rotate relative to cannula (604) about the central axis of cannula (604).

Figures 28, 29:
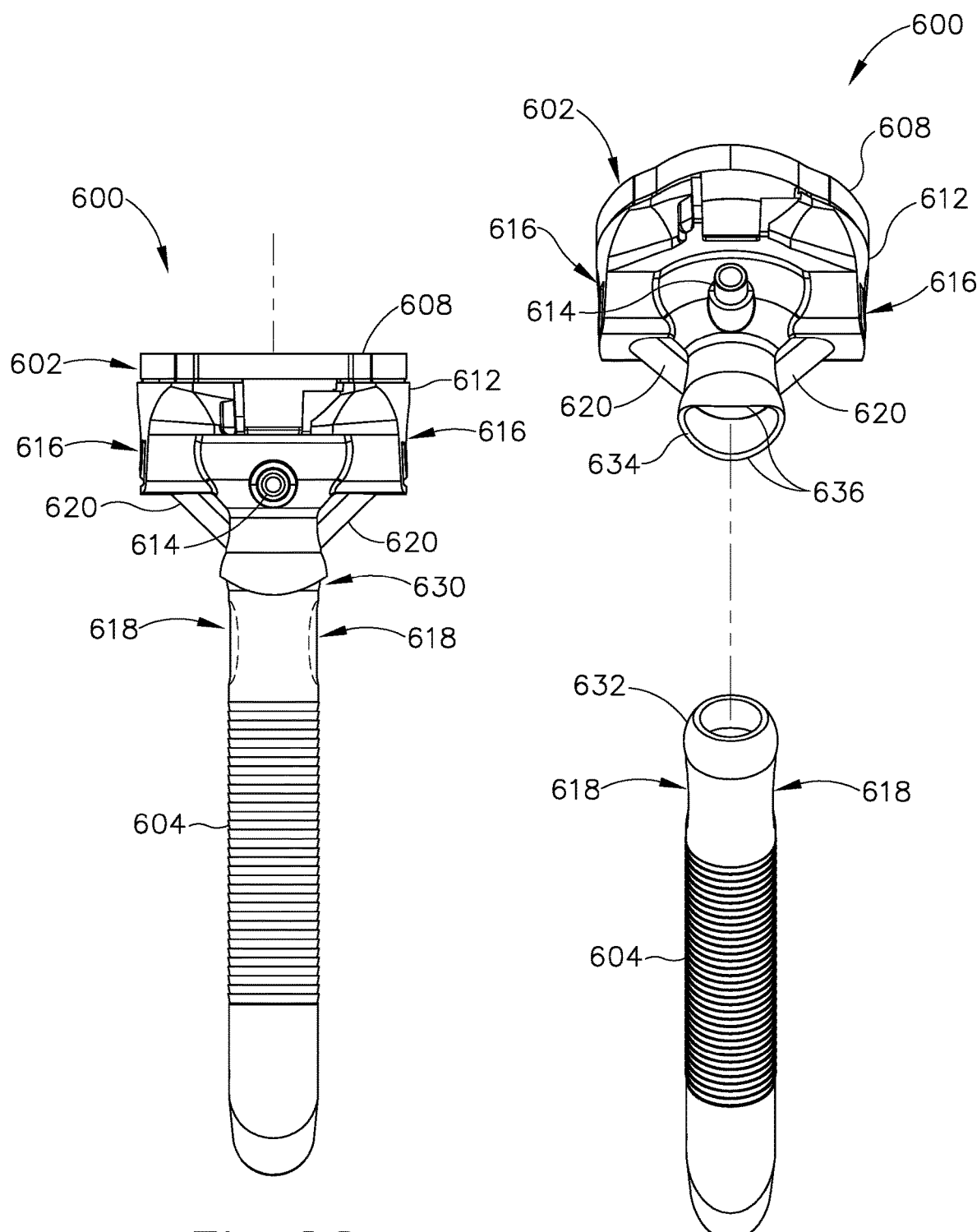
FIG. 28 depicts a front elevational view of another exemplary trocar having a movable neck joint, showing the trocar in a straight configuration.
FIG. 29 depicts a disassembled perspective view of the trocar of FIG. 28.

As shown in the disassembled view of FIG. 29, a ball portion (632) of joint (630) is defined by or otherwise rigidly coupled to a proximal end of cannula (604). A socket portion (634) of joint (630) is defined by or otherwise rigidly coupled to a distal end of distal housing (612). Additionally, ball-and-socket joint (630) includes a hollow interior that enables the interior of housing (602) to communicate with a lumen of cannula (604) such that the working channel of trocar (600) extends axially through ball-and-socket joint (630).

In the present example, socket portion (634) is suitably shaped to promote angular deflection of housing (602) relative to cannula (604) in an axially extending plane that contains needle ports (616, 618). In particular, as shown in FIG. 29, outer walls of socket portion (634) include rounded distal projections (636) configured to engage the proximal portion of cannula (604) to thereby limit deflection of housing (602) in axially extending planes not containing needle ports (616, 618). In other variations of trocar (600), such deflection limiting features may be omitted to enable housing (602) to deflect relative to cannula (604) about a full conference of trocar (600). It will be appreciated that deflection limiting features similar to or different from distal projections (636) may be provided on trocar (500) described above. Optionally, trocar (600) may further include one or more locking mechanisms configured to be activated by a physician to temporarily secure trocar (600) in a particular angled configuration. Additionally, in other variations, trocar (600) may include one or more resilient members (not shown) configured to bias trocar (600) toward the straight configuration shown in FIG. 28. For instance, ball-and-socket joint (630) may be encircled by a resilient member similar to flexible joint sleeve (530) of trocar (500).

Figure 30:
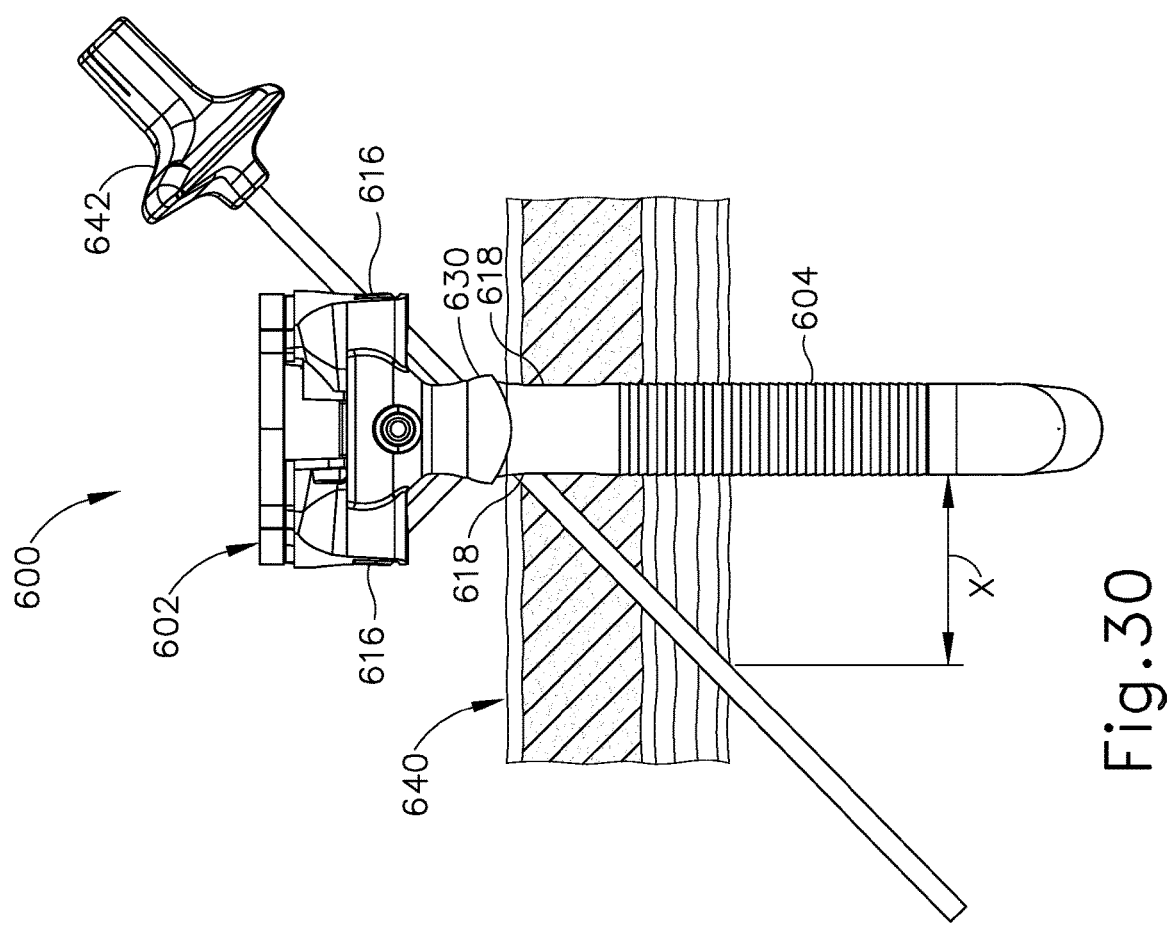
FIG. 30 depicts a front elevational view of the trocar of FIG. 28, showing the trocar positioned in tissue of a first exemplary thickness and oriented in a straight configuration that defines a tissue bite distance.

FIG. 30 shows trocar (600) positioned within an opening formed in tissue (640) of an exemplary first thickness. Tissue (640) includes layers of skin, fat, and fascia similar to tissue (17) described above. A suture passer device (642) is shown directed distally through trocar (600) along a suture path defined by a needle entrance port (616) and a corresponding opposed needle exit port (618). Trocar (600) is provided in a straight configuration such that suture passer device (642) extends distally through trocar (600) and tissue (640) at a first suture path angle relative to the central axis of cannula (604), to thereby define a tissue bite distance (X).

Figure 31:
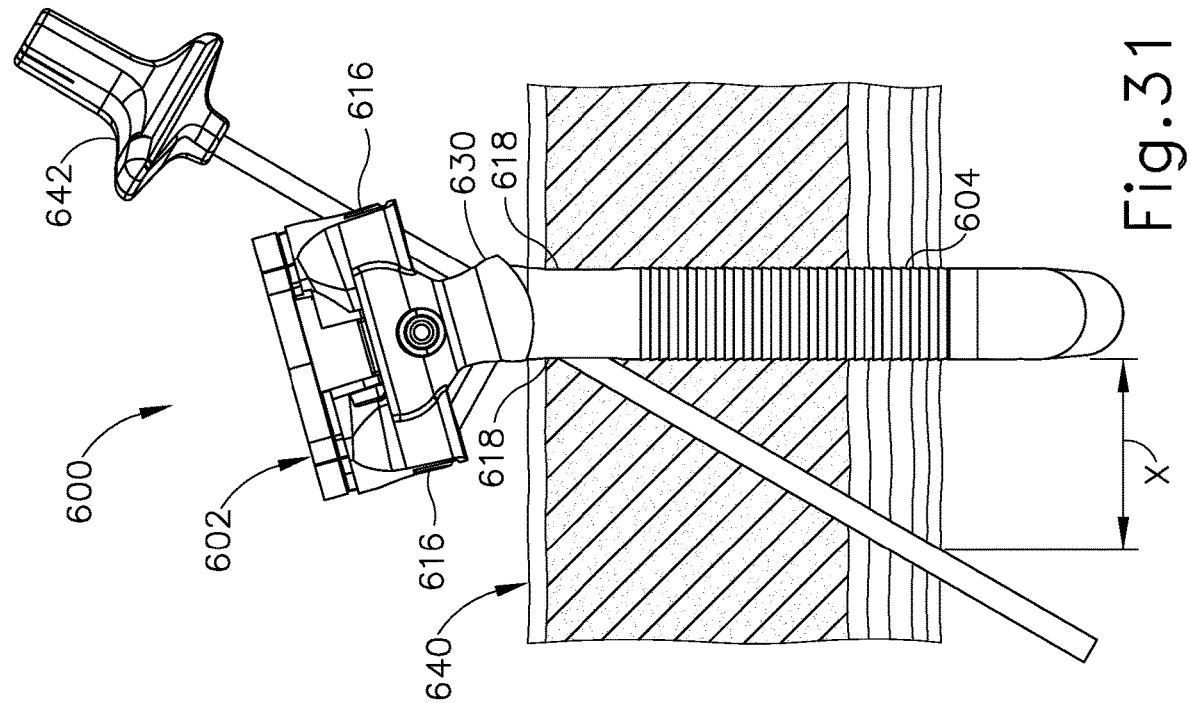
FIG. 31 depicts a front elevational view of the trocar of FIG. 30, showing the trocar positioned in tissue of a second exemplary thickness and oriented in an exemplary angled configuration to define the same tissue bite distance of FIG. 30.

FIG. 31 shows trocar (600) positioned within an opening formed in tissue (650) of an exemplary second thickness that is greater than the first thickness of tissue (640). Tissue (650) is otherwise similar to tissue (640) in that tissue (650) includes layers of skin, fat, and fascia. As shown, trocar (600) is provided in an angled configuration in which housing (602) is deflected relative to cannula (604). Consequently, suture passer device (642) is directed distally through trocar (600) and tissue (650) at a second, smaller suture path angle to achieve the same tissue bite distance (X) as achieved in thinner tissue (640) of FIG. 30. Accordingly, ball-and-socket joint (630) of trocar (600) enables a consistent tissue bite distance (X) to be achieved across a range of different tissue thicknesses.

IX. EXEMPLARY SUTURE PASSER DEVICE

Figure 32:
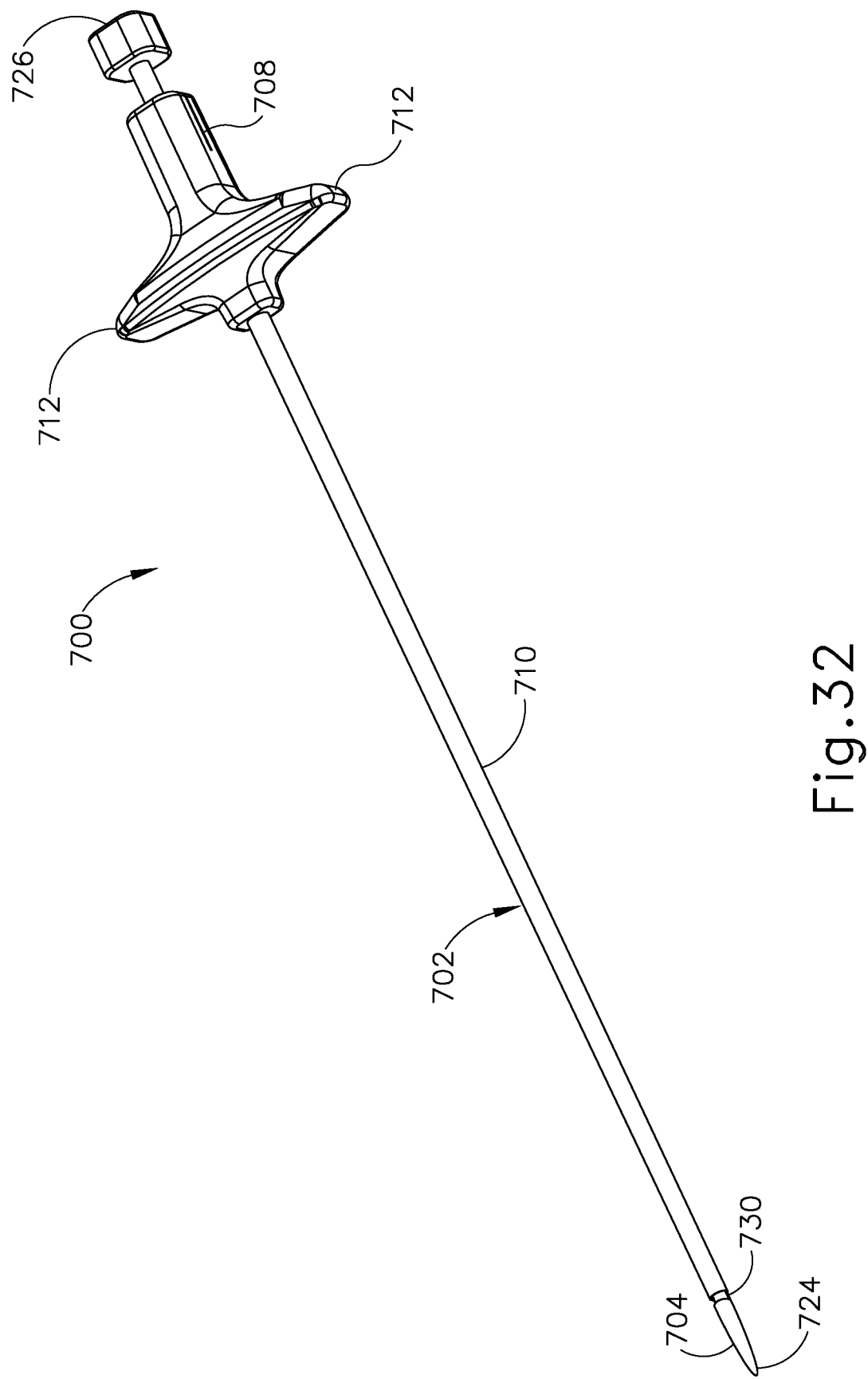
FIG. 32 depicts a perspective view of an exemplary suture passer device configured for used with any of the exemplary trocars disclosed herein.
Figure 33:
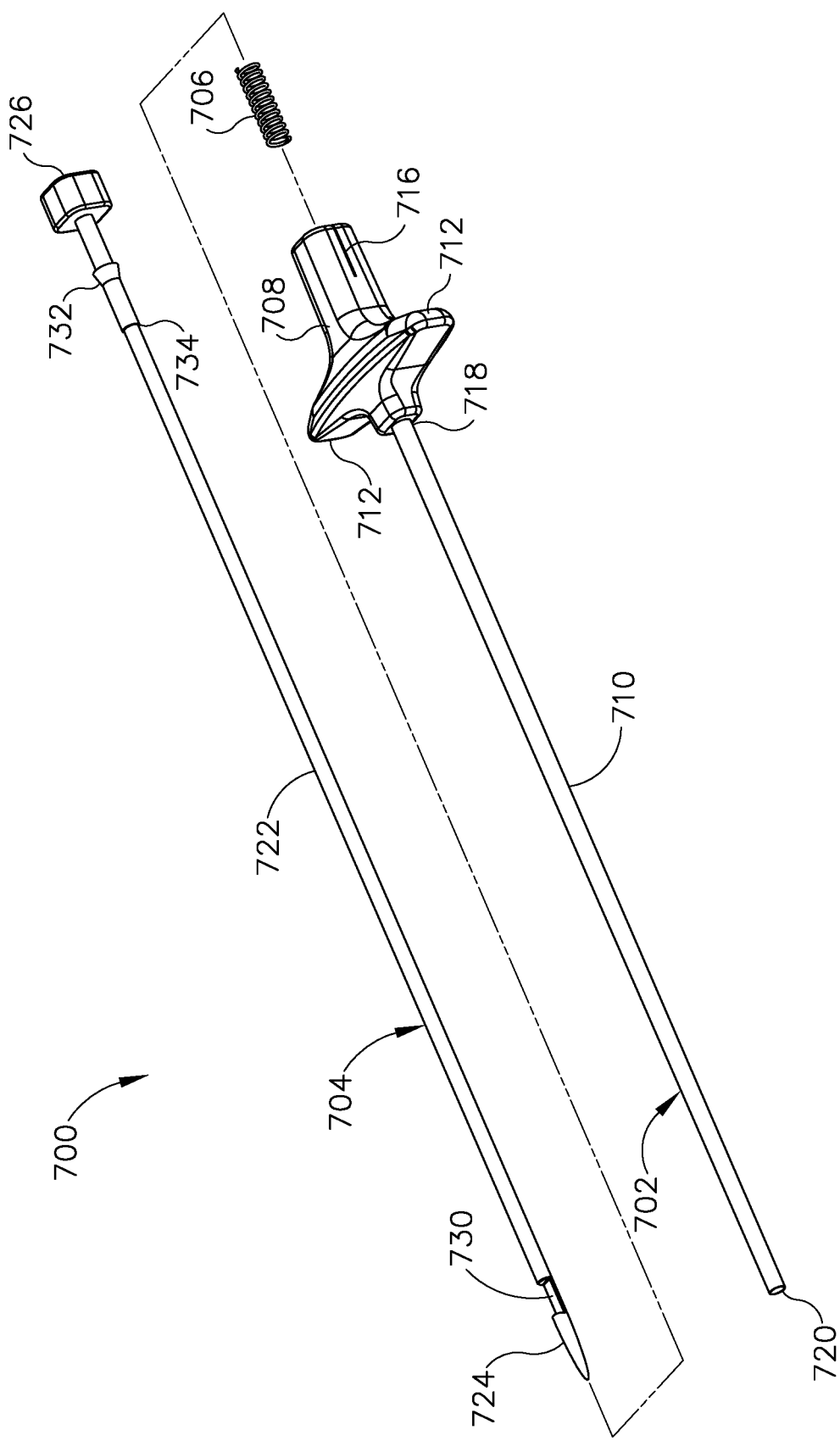
FIG. 33 depicts a disassembled view of the suture passer device of FIG. 32.

FIGS. 32 and 33 show an exemplary suture passer device (700) configured for use with a surgical access device, such as any of the exemplary trocars (10, 100, 270, 300, 340, 400, 500, 600) described above. Suture passer device (700) includes an external housing (702), a needle (704) slidably disposed within housing (702), and a resilient member in the form of a compression spring (706) configured to bias needle (704) proximally relative to housing (702), as described below.

Figure 34:
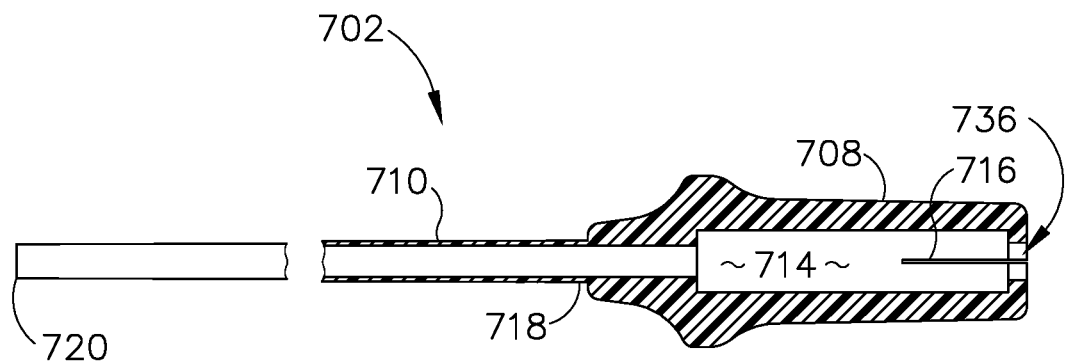
FIG. 34 depicts a side sectional view of a housing of the suture passer device of FIG. 32.

Housing (702) includes a handle (708) and an elongate tube (710) extending distally from handle (708). Handle (708) includes laterally extending projections (712) that enable handle (708) to be easily gripped by a single hand of a physician. As shown in FIG. 34, handle (708) includes an axially extending cavity (714) configured to receive a proximal end portion of needle (704), as described below, and a pair of longitudinal slits (716) extending through opposed sidewalls of handle (708) and opening to cavity (714). As also shown best in FIG. 34, a sidewall of housing tube (710) tapers distally from a first radial thickness at a proximal end (718) of tube (710) that joins with a distal end of handle (708), to an open distal end (720) of tube (710) through which needle (704) extends. This tapered configuration of tube (710) minimizes the presence of a step between the outer surface of tube (710) and the outer surface of needle (704) at open distal end (720), thereby substantially preventing suture passer device (700) from snagging on patient tissue or on features of a surgical access device through which suture passer device (700) is inserted during use. As best seen in FIG. 34, proximal end (718) of tube (710) couples integrally with the distal end of handle (708) so as to provide housing (702) with a monolithic structure. Housing (702) may be formed of a single material, such as a hard plastic, through an injection molding process, for example.

Figure 35:
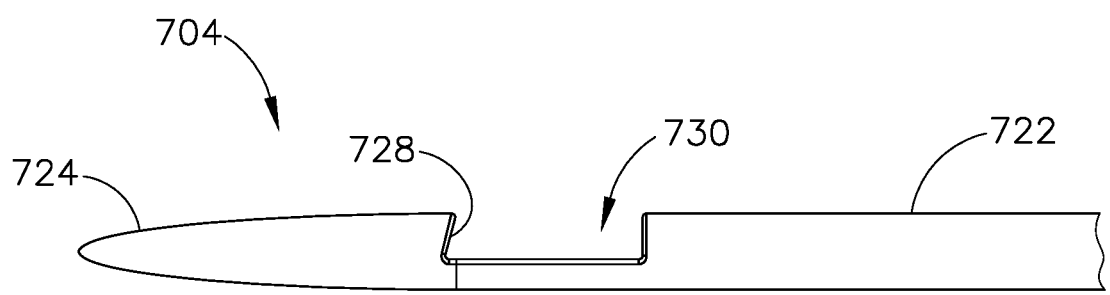
FIG. 35 depicts a side elevational view of a distal end portion of a needle of the suture passer device of FIG. 32.

Needle (704) is slidably disposed within housing (702) and includes a shaft (722), a tapered distal tip (724), and a proximal head (726). As best shown in FIG. 35, needle (704) further includes an angled grasping surface (728) defined by a notch (730) formed in a distal end portion of shaft (722), proximal to distal tip (724). In the present example, grasping surface (728) is generally planar and is angled proximally at an angle of approximately 75 degrees. Grasping surface (728) is configured to engage and capture a suture thread (not shown) against open distal end (720) of housing (702) when needle (704) is actuated to a proximal position (FIG. 36) relative to housing (702), as described in greater detail below.

Figure 36:
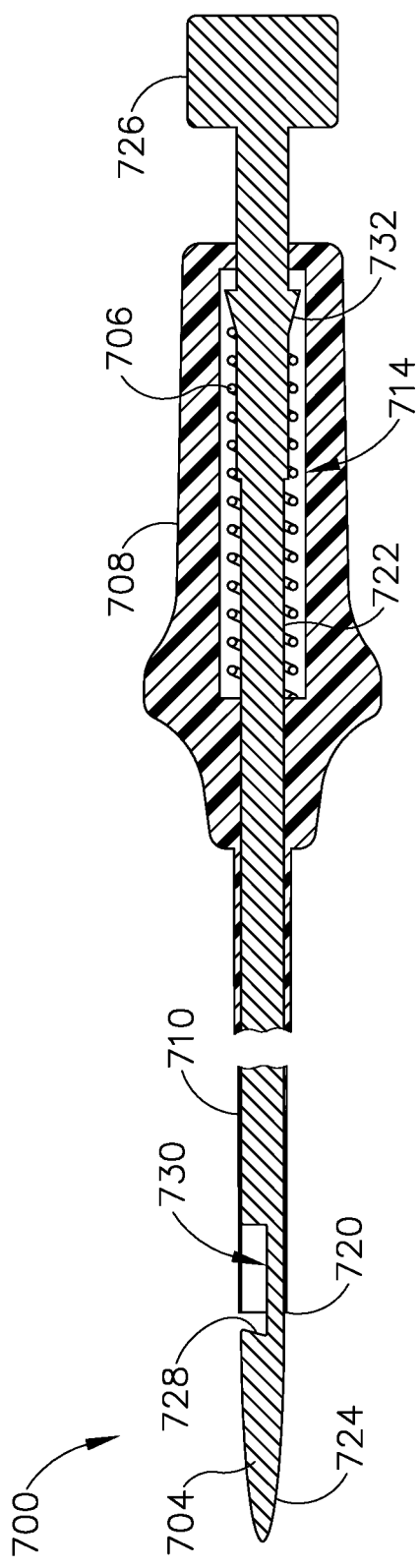
FIG. 36 depicts a side sectional view of the suture passer device of FIG. 32, showing the needle in a proximal position relative to the housing.

As shown in FIG. 33, needle (704) further includes a tapered collar (732) arranged on a proximal portion of needle shaft (722) just distal to needle head (726), and an annular shoulder (734) arranged distal to tapered collar (732) on the proximal shaft portion. Tapered collar (732) tapers distally and is thus configured to promote a snap-fit engagement of needle (704) with housing (702). In particular, as needle (704) is inserted distally through housing (702) during assembly, tapered collar (732) is received through an opening (736) of reduced dimeter formed in a proximal end of handle (708), as shown in FIG. 36. As tapered collar (732) advances distally through opening (736) and into cavity (714) during device assembly, tapered collar (732) causes side portions of handle (708) to resiliently flex laterally away from one another, as enabled by longitudinal slits (716). As tapered collar (732) reaches cavity (714), the side portions of handle (708) snap back together to thereby retain tapered collar (732) within cavity (714) and secure needle (704) longitudinally relative to housing (702). As described below, needle (704) is still permitted to translate relative to housing (702) between proximal and distal positions.

Figure 37:
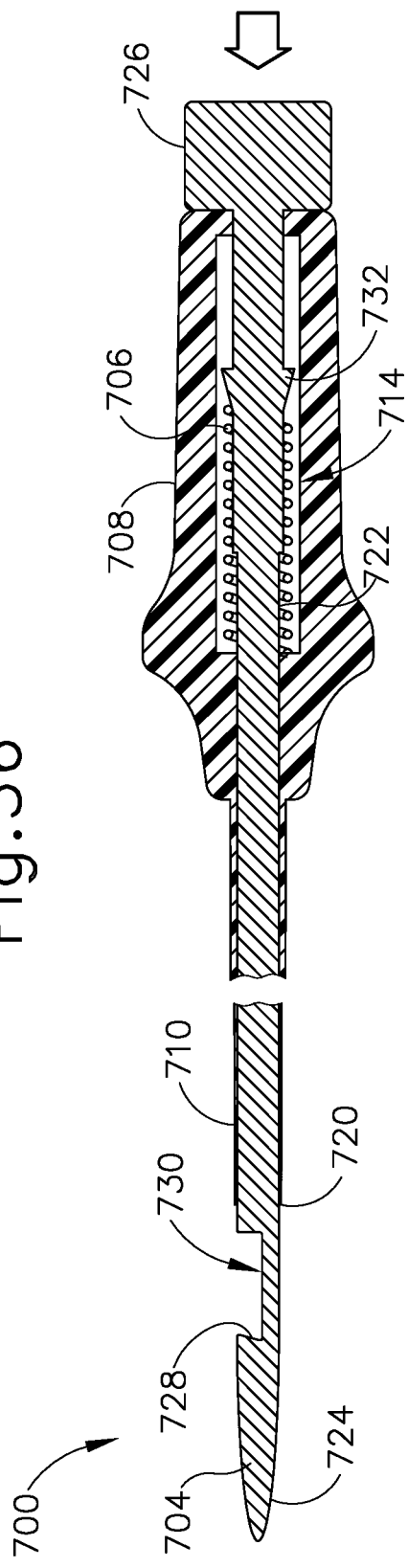
FIG. 37 depicts a side section view of the suture passer device of FIG. 36, showing the needle in a depressed distal position relative to the housing.

As shown best in FIGS. 36 and 37, needle (704) is selectively movable relative to housing (702) between a proximal position (FIG. 36) for grasping a suture thread (not shown), and a distal position (FIG. 37) for releasing the suture thread. Compression spring (706) encircles a proximal portion of needle shaft (722) within handle cavity (714), and is configured to bias needle (704) toward the proximal position. Spring (706) is constrained at a proximal end by tapered collar (732) of needle (704), and at a distal end by a distal wall of cavity (714). As shown in FIG. 36, when needle is in the proximal position, grasping surface (728) confronts open distal end (720) of housing tube (710) such that a suture thread may be clamped within notch (730) between grasping surface (728) and tube (710). As shown in FIG. 37, needle (704) is advanced to the distal position by exerting a distally directed axial force on needle head (726) to thereby compress spring (706) within cavity (714) and drive needle (704) distally until needle head (726) abuts a proximal end of handle (708). In the distal position, shown in FIG. 37, notch (730) is exposed from tube (710) such that a suture thread captured therein may be released, and/or so that needle (704) may be positioned to capture a suture thread within exposed notch (730).

X. OTHER EXEMPLARY FEATURES

Though not shown, the needle guide structures of any of the exemplary trocars disclosed herein may be coupled to one or more rotatable structures configured to rotate about the central axis of the respective trocar. Examples of such a configuration are disclosed in U.S. patent application Ser. No. 15/637,688, entitled "Trocar with Oblique Needle Insertion Port and Coplanar Stopcock," filed Jun. 29, 2017, issued as U.S. Pat. No. 10,485,580 on Nov. 26, 2019, the disclosure of which is incorporated by reference herein. This rotating configuration enables the suture path corresponding to each needle guide structure to be selectively rotationally positioned about the trocar central axis during use. Further, such a configuration may include one or more detents or other rotational limiting mechanisms suitably positioned to define various pre-determined rotational positions of the one or more rotatable structures. The trocar cannula may be provided with a plurality of needle ports arranged circumferentially about the central axis to account for the various rotational positions of the needle guide structures. In various examples, the one or more rotatable structures may be incorporated within or coupled to the cannula or any portion of the housing, for instance.

The teachings presented herein may be further combined with various teachings of any one or more of the following: U.S. patent application Ser. No. 15/637,690, entitled "Needle Guide Instrument with Traverse Suture Capture Feature," filed Jun. 29, 2017, issued as U.S. Pat. No. 10,675,018 on Jun. 9, 2020, the disclosure of which is incorporated by reference herein; U.S. patent application Ser. No. 15/637,702, entitled "Suture Grasping Instrument," filed Jun. 29, 2017, issued as U.S. Pat. No. 10,639,029 on May 5, 2020, the disclosure of which is incorporated by reference herein; U.S. patent application Ser. No. 15/637,712, entitled "Suture Passing Instrument with Puncture Site Identification Feature," filed Jun. 29, 2017, issued as U.S. Pat. No. 10,709,440 on Jul. 14, 2020, the disclosure of which is incorporated by reference herein; U.S. patent application Ser. No. 15/637,696, entitled "Trocar Obturator with Transverse Needle Ports," filed Jun. 29, 2017, issued as U.S. Pat. No. 10,869,690 on Dec. 22, 2020, the disclosure of which is incorporated by reference herein; U.S. patent application Ser. No. 15/637,707, entitled "Surgical Port with Wound Closure Channels," filed Jun. 29, 2017, issued as U.S. Pat. No. 10,568,619 on Feb. 25, 2020, the disclosure of which is incorporated by reference herein; U.S. patent application Ser. No. 15/637,735, entitled "Trocar Obturator with Detachable Rotary Tissue Fastener," filed Jun. 29, 2017, issued as U.S. Pat. No. 10,709,473 on Jul. 14, 2020, the disclosure of which is incorporated by reference herein; U.S. patent application Ser. No. 15/637,778, entitled "Method of Suturing a Trocar Patch Incision," filed Jun. 29, 2017, published as U.S. Pub. No. 2019/0000496 on Jan. 3, 2019, issued as U.S. Pat. No. 11,389,192 on Jul. 19, 2022, the disclosure of which is incorporated by reference herein; and/or other patents and patent application publications incorporated by reference herein.

XI. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical access device, comprising: (a) a cannula having a proximal end, a distal end, and a cannula lumen extending therebetween; (b) a housing assembly coupled to the proximal end of the cannula, wherein the housing assembly comprises: (i) a proximal housing, and (ii) a latch ring arranged distally of the proximal housing and having a user engagement feature, wherein the latch ring is rotatable by the user engagement feature to selectively couple and decouple the proximal housing with the cannula, wherein an interior of the housing assembly communicates with the cannula lumen to define a working channel extending from a proximal end of the surgical access device to a distal end of the surgical access device along a central axis thereof, wherein the working channel is configured to receive a surgical instrument therethrough; (c) a first needle port that opens to the working channel through a first side portion of the surgical access device; and (d) a second needle port that opens to the working channel through a second side portion of the surgical access device; wherein each of the first and second needle ports is configured to direct a suture passer needle through the surgical access device, across the working channel, at an oblique angle relative to the central axis of the surgical access device, wherein the user engagement feature of the latch ring is circumferentially offset from each of the first and second needle ports.

Example 2

The surgical access device of Example 1, wherein the housing assembly further comprises a distal housing coupled to the cannula, wherein the latch ring is arranged between the proximal housing and the distal housing, wherein the latch ring is rotatable relative to at least one of the proximal or distal housings to selectively couple and decouple the proximal housing with the distal housing.

Example 3

The surgical access device of any one or more of the preceding Examples, wherein the latch ring is rotatable to a position in which the user engagement feature is spaced circumferentially equidistantly between the first and second needle ports.

Example 4

The surgical access device of any one or more of the preceding Examples, wherein the latch ring is rotatable to a position in which the user engagement feature is circumferentially offset from each of the first and second needle ports by at least 90 degrees.

Example 5

The surgical access device of Example 4, wherein the first and second needle ports are diametrically opposed from one another, wherein the latch ring is rotatable to a position in which the user engagement feature is circumferentially offset from each of the first and second needle ports by 90 degrees.

Example 6

The surgical access device of any one or more of the preceding Examples, further comprising an insufflation port configured to direct insufflation fluid into the working channel, wherein the latch ring is rotatable to a position in which the user engagement feature is diametrically opposed from the insufflation port.

Example 7

The surgical access device of Example 6, wherein when the user engagement feature is positioned in diametric opposition to the insufflation port, the user engagement feature is spaced circumferentially equidistantly between the first and second needle ports.

Example 8

The surgical access device of Example 7, wherein when the user engagement feature is positioned in diametric opposition to the insufflation port, the user engagement feature is circumferentially offset from each of the first and second needle ports by 90 degrees.

Example 9

The surgical access device of any one or more of the preceding Examples, wherein the user engagement feature comprises an outwardly projecting knob.

Example 10

The surgical access device of any one or more of the preceding Examples, wherein the cannula includes a proximal hub having a larger diameter than medial and distal portions of the cannula, wherein the first and second needle ports extend through the proximal hub.

Example 11

The surgical access device of any one or more of the preceding Examples, wherein the first needle port comprises a first needle entrance port and the second needle port comprises a second needle entrance port, wherein the surgical access device further comprises a first needle exit port arranged distally of the first needle entrance port, and a second needle exit port arranged distally of the second needle entrance port, wherein the first needle entrance port and the first needle exit port together define a first suture path extending obliquely across the central axis of the surgical access device, wherein the second needle entrance port and the second needle exit port together define a second suture path extending obliquely across the central axis of the surgical access device.

Example 12

The surgical access device of Example 11, wherein the first and second needle entrance ports and the first and second needle exit ports are arranged such that the first and second suture paths extend through the central axis of the surgical access device.

Example 13

The surgical access device of any one or more of Examples 11 through 12, further comprising a first needle guide structure configured to guide a suture passer needle along the first suture path, and a second needle guide structure configured to guide a suture passer needle along the second suture path.

Example 14

The surgical access device of any one or more of the Examples 11 through 13, wherein each of the first and second needle entrance ports and each of the first and second needle exit ports is provided with a pierceable seal.

Example 15

The surgical access device of Example 14, further comprising a sleeve that encircles at least a portion of the cannula, wherein the sleeve defines the pierceable seals for the first and second needle exit ports.

Example 16

A surgical access device, comprising: (a) a cannula having a proximal end, a distal end, and a cannula lumen extending therebetween; (b) a housing assembly coupled to the proximal end of the cannula, wherein the housing assembly comprises: (i) a proximal housing, and (ii) a latch ring arranged distally of the proximal housing and having a user engagement feature, wherein the latch ring is movable by the user engagement feature to selectively couple and decouple the proximal housing with the cannula, wherein an interior of the housing assembly communicates with the cannula lumen to define a working channel extending from a proximal end of the surgical access device to a distal end of the surgical access device along a central axis thereof, wherein the working channel is configured to receive a surgical instrument therethrough; (c) a first needle port that opens to the working channel through a first side portion of the surgical access device; and (d) a second needle port that opens to the working channel through a second side portion of the surgical access device; wherein each of the first and second needle ports is configured to direct a suture passer needle through the surgical access device, across the working channel, at an oblique angle relative to the central axis of the surgical access device, wherein the user engagement feature of the latch ring is circumferentially offset from each of the first and second needle ports by at least 90 degrees.

Example 17

The surgical access device of Example 16, wherein the user engagement feature is movable to a position in which the user engagement feature is spaced circumferentially equidistantly between the first and second needle ports.

Example 18

The surgical access device of any one or more of Examples 16 through 17, wherein the user engagement feature comprises an outwardly projecting knob.

Example 19

A surgical access device, comprising: (a) a cannula having a proximal end, a distal end, and a cannula lumen extending therebetween; (b) a housing assembly coupled to the proximal end of the cannula, wherein the housing assembly comprises: (i) a proximal housing, and (ii) a latch ring arranged distally of the proximal housing and having an outwardly projecting knob, wherein the latch ring is movable by the outwardly projecting knob to selectively couple and decouple the proximal housing with the cannula, wherein an interior of the housing assembly communicates with the cannula lumen to define a working channel extending from a proximal end of the surgical access device to a distal end of the surgical access device along a central axis thereof, wherein the working channel is configured to receive a surgical instrument therethrough; (c) an insufflation port configured to direct insufflation fluid into the working channel; (d) a first needle port that opens to the working channel through a first side portion of the surgical access device; and (e) a second needle port that opens to the working channel through a second side portion of the surgical access device; wherein each of the first and second needle ports is configured to direct a suture passer needle through the surgical access device, across the working channel, at an oblique angle relative to the central axis of the surgical access device, wherein the outwardly projecting knob of the latch ring is circumferentially offset from each of the first needle port, the second needle port, and the insufflation port.

Example 20

The surgical access device of Example 19, wherein the user engagement feature is movable to a position in which the user engagement feature is diametrically opposed from the insufflation port and is circumferentially offset from at least one of the first or second needle ports by at least 90 degrees.

Example 21

A surgical access device, comprising: (a) a cannula having a proximal end, a distal end, and a cannula lumen extending therebetween; (b) a housing coupled to the proximal end of the cannula, wherein the housing defines a housing interior in communication with the cannula lumen; (c) a working channel extending between proximal and distal ends of the surgical access device along a central axis thereof, wherein the working channel is defined by the cannula lumen and the housing interior, wherein the working channel is configured to receive a surgical instrument therethrough; (d) a needle entrance port arranged on a first side portion of the surgical access device, wherein the needle entrance port opens to the working channel; (e) a needle exit port arranged distally of the needle entrance port on a second side portion of the surgical access device, wherein the needle exit port communicates with the needle entrance port to define a suture path extending through the surgical access device at an oblique angle relative to the central axis; and (f) a suture passer guide tube extending through the needle entrance and exit ports, wherein the suture passer guide tube includes a distal tube end positioned outwardly of the cannula at a predetermined radial distance from the central axis, wherein the suture passer guide tube is configured to guide a suture passer device distally through the surgical access device along the suture path.

Example 22

The surgical access device of Example 21, wherein the suture passer guide tube comprises a proximal tube portion defining a proximal tube end, and a distal tube portion defining the distal tube end, wherein the distal tube portion is angled relative to the proximal tube portion.

Example 23

The surgical access device of Example 22, in combination with a suture passer device having a flexible needle, wherein the suture passer guide tube is configured to receive the flexible needle, wherein the flexible needle is configured to resiliently flex as the flexible needle passes between the proximal tube portion and the distal tube portion.

Example 24

The surgical access device of any or more of Examples 22 through 23, wherein the distal tube portion is angled relative to the proximal tube portion in a direction toward the central axis.

Example 25

The surgical access device of any or more of Examples 22 through 24, wherein the distal tube portion extends along an axis parallel to the central axis.

Example 26

The surgical access device of any or more of Examples 22 through 25, wherein the suture passer guide tube includes a curved medial portion arranged between the proximal and distal tube portions, wherein the curved medial portion is positioned distally of the needle exit port.

Example 27

The surgical access device of any one or more of Examples 21 through 26, wherein the needle exit port is arranged on the cannula.

Example 28

The surgical access device of Examples 21 through 27, wherein the cannula includes a sleeve, wherein the suture path extends through the sleeve.

Example 29

The surgical access device of any one or more of Examples 21-28, wherein the needle entrance port and the needle exit port define a first pair of needle ports defining a first suture path, wherein the surgical access device further comprises a second pair of needle ports defining a second suture path, wherein the second pair of needle ports includes a second needle entrance port and a second needle exit port.

Example 30

The surgical access device of Example 29, wherein the second suture path intersects the first suture path.

Example 31

The surgical access device of any one or more of Examples 29 through 30, wherein the second needle entrance port is diametrically opposed from the first needle entrance port, wherein the second needle exit port is diametrically opposed from the first needle exit port.

Example 32

The surgical access device of any one or more of Examples 21 through 31, further comprising an insufflation port configured to direct insufflation fluid into the working channel.

Example 33

The surgical access device of any one or more of Examples 21 through 32, wherein the housing includes a proximal housing portion and a user engagement feature, wherein the user engagement feature is actuatable to selectively detach the proximal housing portion from the cannula.

Example 34

The surgical access device of Example 33, wherein the housing further includes a distal housing portion, wherein the distal housing portion is secured to the cannula and supports the user engagement feature, wherein the proximal housing portion is selectively detachable from the distal housing portion.

Example 35

The surgical access device of any one or more of Examples 33 through 34, further comprising a seal positioned to provide communication between the housing interior and the cannula lumen, wherein the proximal housing portion is removable from the cannula to expose the seal.

Example 36

A surgical access device, comprising: (a) a cannula having a proximal end, a distal end, and a cannula lumen extending therebetween; (b) a housing coupled to the proximal end of the cannula, wherein the housing defines a housing interior in communication with the cannula lumen; (c) a working channel extending between proximal and distal ends of the surgical access device along a central axis thereof, wherein the working channel is defined by the cannula lumen and the housing interior, wherein the working channel is configured to receive a surgical instrument therethrough; (d) a first pair of opposed needle ports that open to the working channel and communicate with one another to define a first suture path extending through the surgical access device at an oblique angle relative to the central axis; (e) a second pair of opposed needle ports that open to the working channel and communicate with one another to define a second suture path extending through the surgical access device at an oblique angle relative to the central axis; and (f) a suture passer guide tube, wherein the suture passer guide tube is configured to be removably received along each of the first and second suture paths independently to guide a suture passer needle distally through the surgical access device along the suture paths.

Example 37

The surgical access device of Example 36, wherein the suture passer guide tube includes a proximal tube portion configured to extend across the working channel, and a distal tube portion extending angularly relative to the proximal tube portion.

Example 38

The surgical access device of any one or more of Examples 36 through 37, further comprising an insufflation port configured to direct insufflation fluid into the working channel.

Example 39

A surgical assembly, comprising: (a) a suture passer device having a flexible needle; and (b) a surgical access device configured to guide the flexible needle through tissue for suturing a wound, wherein the surgical access device comprises: (i) a cannula having a proximal end, a distal end, and a cannula lumen extending therebetween, (ii) a housing coupled to the proximal end of the cannula, wherein the housing assembly defines a housing interior in communication with the cannula lumen, (iii) a working channel extending between proximal and distal ends of the surgical access device along a central axis thereof, wherein the working channel is defined by the cannula lumen and the housing interior, wherein the working channel is configured to receive a surgical instrument therethrough, (iv) a needle entrance port arranged on a first side portion of the surgical access device, wherein the needle entrance port opens to the working channel, (v) a needle exit port arranged distally of the needle entrance port on a second side portion of the surgical access device, wherein the needle exit port communicates with the needle entrance port to define a suture path extending through the surgical access device at an oblique angle relative to the central axis, and (vi) a suture passer guide tube extending through the needle entrance and exit ports, wherein the suture passer guide tube is configured to guide the flexible needle distally through the surgical access device along the suture path.

Example 40

The surgical access device of Example 39, wherein the suture passer guide tube includes a distal tube end arranged outwardly of the cannula at a predetermined radial distance from the central axis.

Example 41

A surgical access device, comprising: (a) a cannula having a proximal end, a distal end, and a cannula lumen extending therebetween; (b) a housing coupled to the proximal end of the cannula, wherein the housing defines a housing interior in communication with the cannula lumen; (c) a working channel extending between proximal and distal ends of the surgical access device along a central axis thereof, wherein the working channel is defined by the cannula lumen and the housing interior, wherein the working channel is configured to receive a surgical instrument therethrough; (d) a needle entrance port arranged on a side portion of the housing, wherein the needle entrance port opens to the working channel; and (e) a needle exit port arranged distally of the needle entrance port on a side portion of the cannula, wherein the needle exit port communicates with the needle entrance port to define a suture path extending through the surgical access device at an oblique angle relative to the central axis, wherein when the cannula is positioned within a first tissue of a first thickness, the needle entrance and exit ports are configured to guide a suture passer device through the surgical access device and the first tissue to define a tissue bite distance in the first tissue, and wherein when the cannula is positioned within a second tissue of a second thickness different than the first thickness, the needle entrance and exit ports are configured to guide the suture passer device through the surgical access device and the second tissue to define the same tissue bite distance in the second tissue.

Example 42

The surgical access device of Example 41, wherein the needle entrance port and the needle exit port define a first pair of needle ports defining a first suture path through the surgical access device, wherein the surgical access device further comprises a second pair of needle ports defining a second suture path through the surgical access device, wherein the second pair of needle ports includes a second needle entrance port arranged on a side portion of the housing and a second needle exit port arranged distally of the second needle entrance port on a side portion of the cannula.

Example 43

The surgical access device of Example 42, wherein the second suture path intersects the first suture path.

Example 44

The surgical access device of any one or more of Examples 41 through 43, further comprising a suture passer guide tube extending through the needle entrance and exit ports, wherein the suture passer guide tube includes a distal tube end positioned outwardly of the cannula at a predetermined radial distance from the central axis, wherein the suture passer guide tube is configured to guide a suture passer device distally through the surgical access device and the first and second tissues.

Example 45

The surgical access device of Example 44, wherein the suture passer guide tube comprises a proximal tube portion defining a proximal tube end, and a distal tube portion defining the distal tube end, wherein the distal tube portion is angled relative to the proximal tube portion.

Example 46

The surgical access device of Example 45, in combination with a suture passer device having a flexible needle, wherein the suture passer guide tube is configured to receive the flexible needle, wherein the flexible needle is configured to resiliently flex as the flexible needle passes between the proximal tube portion and the distal tube portion.

Example 47

The surgical access device of any one or more of Examples 45 through 46, wherein the distal tube portion is angled relative to the proximal tube portion in a direction toward the central axis.

Example 48

The surgical access device of any one or more of Examples 45 through 47, wherein the distal tube portion extends along an axis parallel to the central axis.

Example 49

The surgical access device of any one or more of Examples 45 through 48, wherein the suture passer guide tube includes a curved medial portion arranged between the proximal and distal tube portions, wherein the curved medial portion is positioned distally of the needle exit port.

Example 50

The surgical access device of any one or more of Examples 41 through 49, wherein the housing is coupled to the proximal end of the cannula with a movable joint, wherein the movable joint is configured to enable the housing to deflect relative to the cannula.

Example 51

The surgical access device of Example 50, wherein the movable joint comprises a flexible material.

Example 52

The surgical access device of Example 51, wherein the movable joint comprises a bellow.

Example 53

The surgical access device of Example 50, wherein the movable joint comprises a ball-and-socket joint.

Example 54

The surgical access device of any of the preceding Examples, in combination with a suture passer device having a housing and a needle slidably disposed within the housing, wherein the needle is movable relative to the housing between a proximal position for grasping a suture thread and a distal position for releasing the suture thread, wherein the housing includes a handle portion and elongate tube extending distally from the handle portion, wherein the elongate tube has a sidewall that tapers distally.

Example 55

The surgical access device of Example 44, wherein the needle includes an angled grasping surface arranged proximal to a distal tip of the needle, wherein the angled grasping surface is configured to grasp a suture thread when the needle is in the proximal position.

Example 56

A surgical access device, comprising: (a) a cannula having a proximal end, a distal end, and a cannula lumen extending therebetween; (b) a housing having a housing interior in communication with the cannula lumen; (c) a movable joint that couples the housing with the proximal end of the cannula, wherein the movable joint is configured to enable the housing to deflect relative to the cannula between a straight configuration in which a central axis of the housing aligns coaxially with a central axis of the cannula, and an angled configuration in which the central axis of the housing is angled relative to the central axis of the cannula; (d) a working channel extending between proximal and distal ends of the surgical access device, wherein the working channel is defined by the cannula lumen, the housing interior, and an interior of the movable joint, wherein the working channel is configured to receive a surgical instrument therethrough when the housing is in the straight configuration; (e) a needle entrance port arranged on a first side portion of the surgical access device, wherein the needle entrance port opens to the working channel; and (f) a needle exit port arranged distally of the needle entrance port on a second side portion of the surgical access device, wherein the needle exit port communicates with the needle entrance port to define a suture path extending through the surgical access device at an oblique angle relative to the central axis of the cannula.

Example 57

The surgical access device of Example 56, wherein the movable joint comprises a flexible bellow.

Example 58

The surgical access device of Example 56, wherein the movable joint comprises a ball-and-socket joint.

Example 59

A suture passer device configured to direct a suture thread through a surgical access device, comprising: (a) a housing, wherein the housing includes: (i) a handle portion, and (ii) an elongate tube extending distally from the handle portion, wherein the handle portion and the elongate tube define a monolithic structure; and (b) a needle slidably disposed within the housing, wherein the needle includes: (i) a proximal end, (ii) a tapered distal tip, and (iii) an angled grasping surface arranged proximal to the tapered distal tip, wherein the needle is movable relative to the housing between a proximal position for grasping a suture thread with the angled grasping surface, and a distal position for releasing the suture thread.

Example 60

The suture passer device of Example 59, wherein at least one of: (a) the elongate tube has a sidewall that tapers distally, or (b) the angled grasping surface defines an angle of 75 degrees relative to a longitudinal axis of the needle.

Example 61

The suture passer device of any one or more of Examples 59 through 60, wherein the elongate tube has a sidewall that tapers distally.

Example 62

The suture passer device of any one or more of Examples 59 through 61, wherein the needle is flexible.

Example 63

The suture passer device of any one or more of Examples 59 through 62, in combination with any of the surgical access devices disclosed herein.

XII. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical access assembly, comprising:
   (a) a trocar including:
      (i) a cannula having a proximal end, a distal end, and a cannula lumen extending therebetween and defining a central axis,
      (ii) a housing having a housing interior in communication with the cannula lumen,
      (iii) a working channel extending between proximal and distal ends of the trocar, wherein the working channel is defined by the cannula lumen and the housing interior, wherein the working channel is configured to receive a surgical instrument therethrough,
      (iv) an entrance port arranged on a first side portion of the trocar, wherein the entrance port opens to the working channel, and
      (v) an exit port arranged distally of the entrance port on a second side portion of the trocar, wherein the exit port communicates with the entrance port to define a suture path extending through the trocar at an oblique angle relative to the central axis;
   (b) a suture passer guide tube having a proximal tube portion and a distal tube portion angled relative to the proximal tube portion, wherein the suture passer guide tube is configured to be passed distally through the entrance port, across the working channel, and through the exit port such that a portion of the proximal tube portion resides within the working channel and an entirety of the distal tube portion resides externally of the working channel, wherein the suture passer guide tube is configured to guide a suture distally through the trocar and tissue adjacent to the cannula; and
   (c) a suture passer device configured to pass through the suture passer guide tube and capture an end of a suture thread.

2. The surgical access assembly of claim 1, wherein the suture passer guide tube further includes a curved medial portion between the proximal tube portion and the distal tube portion, wherein the distal tube portion is generally straight such that the distal tube portion is configured to extend parallel to the central axis when the suture passer guide tube is coupled with the trocar.

3. The surgical access assembly of claim 2, wherein the distal tube portion is configured to position a suture thread at a predetermined radial distance from the central axis.

4. A surgical access assembly, comprising:
   (a) a cannula having a proximal end, a distal end, and a cannula lumen extending therebetween;
   (b) a housing coupled to the proximal end of the cannula, wherein the housing includes a housing interior in communication with the cannula lumen;
   (c) a working channel extending between proximal and distal ends of the surgical access assembly along a central axis thereof, wherein the working channel is defined by the cannula lumen and the housing interior, wherein the working channel is configured to receive a surgical instrument therethrough along the central axis;
   (d) a guide passage extending obliquely relative to the central axis; and
   (e) a suture passer guide tube configured to slidably receive a suture passer device therethrough,
   wherein the guide passage is configured to guide the suture passer guide tube distally through the surgical access assembly and across the working channel at an oblique angle relative to the central axis,
   wherein at least a portion of the suture passer guide tube is configured to assume a resiliently deflected state while passing distally across the working channel from a first side of the working channel to a second side of the working channel and then resume a non-deflected state after emerging distally from the surgical access assembly.

5. The surgical access assembly of claim 4, wherein at least a portion of the guide passage extends external to the housing.

6. The surgical access assembly of claim 4, wherein the guide passage includes a first guide passage having a first entrance port, wherein the first entrance port is in communication with a first passage lumen and the first entrance port is configured to guide the suture passer guide tube into the first guide passage.

7. The surgical access assembly of claim 6, wherein the guide passage includes a second guide passage having a second entrance port, wherein the second entrance port is in communication with a second passage lumen and the second entrance port is configured to guide the suture passer guide tube into the second guide passage.

8. The surgical access assembly of claim 7, further comprising a first exit port positioned on a side surface of the cannula and in communication with the first passage lumen, wherein the first entrance port, the first exit port, and the first passage lumen define a first suture path through the surgical access assembly.

9. The surgical access assembly of claim 8, further comprising a second exit port positioned on the side surface of the cannula and in communication with a second passage lumen, wherein the second entrance port, the second exit port, and the second passage lumen define a second suture path through the surgical access assembly.

10. The surgical access assembly of claim 9, wherein the cannula defines a cannula axis, wherein the first entrance port is positioned on a first side of the cannula axis, wherein the first exit port is positioned on a second side of the cannula axis.

11. The surgical access assembly of claim 10, wherein the second entrance port is positioned on the second side of the cannula axis, and the second exit port is positioned on the first side of the cannula axis.

12. The surgical access assembly of claim 11, wherein each of the first and second exit ports includes a vertical slit on the side surface of the cannula.

13. The surgical access assembly of claim 4, wherein the suture passer guide tube includes a straight first portion, a curved second portion extending distally from the straight first portion, and a straight third portion extending distally from the curved second portion, at a predetermined angle relative to the straight first portion.

14. The surgical access assembly of claim 13, wherein the suture passer guide tube is configured to assume a bent configuration when in a relaxed state, wherein the suture passer guide tube is configured to resiliently deflect into a straightened configuration when passing through the guide passage and subsequently reassumes the bent configuration once fully seated within the surgical access assembly.

15. The surgical access assembly of claim 14, wherein the suture passer guide tube is configured to be temporarily straightened from the bent configuration while traversing the guide passage.

16. The surgical access assembly of claim 15, wherein the suture passer guide tube is configured to resume the bent configuration after passing through the surgical access assembly.

17. The surgical access assembly of claim 4, wherein the suture passer guide tube includes a straight proximal portion, a bent medial portion, and a straight distal portion, wherein the straight proximal portion is configured to be positioned within the guide passage and extend across the working channel obliquely relative to the central axis while the straight distal portion is positioned external to the cannula and extends parallel to the central axis.

18. A surgical access assembly, comprising:
(a) a cannula having a proximal end, a distal end, and a cannula lumen extending therebetween;
(b) a housing coupled to the proximal end of the cannula, wherein the housing includes a housing interior in communication with the cannula lumen;
(c) a working channel extending between proximal and distal ends of the surgical access assembly along a central axis thereof, wherein the working channel is defined by the cannula lumen and the housing interior, wherein the working channel is configured to receive a surgical instrument therethrough along the central axis;
(d) a guide tube extending slantwise relative to the working channel, wherein a portion of the guide tube is positioned on an external surface of the housing; and
(e) a suture passer tube sized and configured to pass through the guide tube at an oblique angle relative to the central axis, wherein the suture passer tube includes a straight first portion, a curved second portion extending distally from the straight first portion, and a straight third portion extending distally from the curved second portion at a predetermined angle relative to the straight first portion when fully seated within the surgical access assembly.

* * * * *